US012653991B2

(12) United States Patent
Malek et al.

(10) Patent No.: US 12,653,991 B2
(45) Date of Patent: Jun. 16, 2026

(54) CATHETER SYSTEMS AND METHODS FOR MEDICAL PROCEDURES USING CATHETERS

(71) Applicant: CEREVASC, INC., Auburndale, MA (US)

(72) Inventors: Adel M. Malek, Weston, MA (US); Carl Heilman, Wayland, MA (US)

(73) Assignee: CereVasc, Inc., Auburndale, MA (US)

( * ) Notice: Subject to any disclaimer, the term of this patent is extended or adjusted under 35 U.S.C. 154(b) by 518 days.

(21) Appl. No.: 18/190,902

(22) Filed: Mar. 27, 2023

(65) Prior Publication Data

US 2023/0233819 A1    Jul. 27, 2023

Related U.S. Application Data

(63) Continuation of application No. PCT/US2021/056194, filed on Oct. 22, 2021.
(Continued)

(51) Int. Cl.
*A61M 27/00*        (2006.01)
*A61B 5/00*         (2006.01)
(Continued)

(52) U.S. Cl.
CPC ......... *A61M 27/006* (2013.01); *A61B 5/0084* (2013.01); *A61B 8/12* (2013.01);
(Continued)

(58) Field of Classification Search
CPC ................ A61M 27/006; A61M 25/04; A61M 2025/0042; A61M 2025/0076;
(Continued)

(56) References Cited

U.S. PATENT DOCUMENTS 9,204,893 B2    12/2015  Rizk et al.
11,497,552 B2   11/2022  Morales
(Continued)

FOREIGN PATENT DOCUMENTS

EP            1839602 B1    7/2009
WO    WO 2009/036039 A1    3/2009
(Continued)

OTHER PUBLICATIONS

Extended European Search Report for EP Patent Appln. No. 23197404.9 dated Jan. 16, 2024.
(Continued)

*Primary Examiner* — Kai H Weng
*Assistant Examiner* — Katherine-Ph Minh Pham
(74) *Attorney, Agent, or Firm* — Vista IP Law Group, LLP

(57)              ABSTRACT

An intracranial intervention system comprises a seeker wire and delivery catheter used to navigate and access a target location within the intracranial subarachnoid spaces (ISAS) of a patient. A microcatheter is then advanced through the delivery catheter to perform a therapeutic procedure, such as installing a shunt within the ISAS to drain cerebral-spinal fluid (CSF). The shunt may be configured to drain CSF from a first and second ISAS, and includes a distal portion which extends into the first ISAS via the second ISAS and a dural venus sinus (DVS) of the patient. The shunt has a main body portion positioned and secured within the second ISAS, a distal portion extending into the first ISAS and the main body portion in the second ISAS have CSF intake opening which allow CSF to flow into a shunt lumen and out through an outflow opening positioned in the DVS.

4 Claims, 51 Drawing Sheets

Related U.S. Application Data

(60) Provisional application No. 63/254,737, filed on Oct. 12, 2021, provisional application No. 63/246,760, filed on Sep. 21, 2021, provisional application No. 63/104,771, filed on Oct. 23, 2020.

(51) Int. Cl.

| | |
|---|---|
| *A61B 8/12* | (2006.01) |
| *A61B 17/221* | (2006.01) |
| *A61B 17/32* | (2006.01) |
| *A61M 25/00* | (2006.01) |
| *A61M 25/04* | (2006.01) |
| *A61M 25/09* | (2006.01) |
| *A61N 5/06* | (2006.01) |

(52) U.S. Cl.
CPC ..... *A61B 17/221* (2013.01); *A61B 17/320016* (2013.01); *A61M 2025/0042* (2013.01); *A61M 2025/0076* (2013.01); *A61M 25/04* (2013.01); *A61M 2025/09183* (2013.01); *A61N 2005/0612* (2013.01)

(58) Field of Classification Search
CPC ...... A61M 2025/09183; A61M 25/007; A61M 2025/0095; A61M 2025/0183; A61B 5/0084; A61B 8/12; A61B 17/221; A61B 17/320016; A61B 17/320708; A61N 2005/0612; A61N 5/067
See application file for complete search history.

(56) References Cited

U.S. PATENT DOCUMENTS

| | | | | |
|---|---|---|---|---|
| 11,806,523 | B2 | 11/2023 | Morales | |
| 2009/0125093 | A1 | 5/2009 | Hansen | |
| 2012/0130467 | A1* | 5/2012 | Selden | A61B 17/11 |
| | | | | 623/1.2 |
| 2012/0296256 | A1* | 11/2012 | Heilman | A61M 27/002 |
| | | | | 604/8 |
| 2020/0069927 | A1 | 3/2020 | Malek et al. | |

FOREIGN PATENT DOCUMENTS

| | | | | |
|---|---|---|---|---|
| WO | WO 2016/070147 | A1 | 5/2016 | |
| WO | WO 2018/017981 | | 1/2018 | |
| WO | WO 2019/173784 | | 9/2019 | |
| WO | WO-2019173784 | A1 * | 9/2019 | A61M 25/04 |
| WO | WO2021257810 | A1 | 12/2021 | |
| WO | WO 2022006317 | | 1/2022 | |

OTHER PUBLICATIONS

PCT International Search Report for PCT/US2021/056194, Applicant: Cerevasc, Inc., Form PCT/ISA/210 and 220, dated Mar. 11, 2022 (7 pages).
PCT Written Opinion of the International Search Authority for PCT/US2021/056194, Applicant: Cerevasc, Inc., Form PCT/ISA/237, dated Mar. 11, 2022 (7 pages).

* cited by examiner

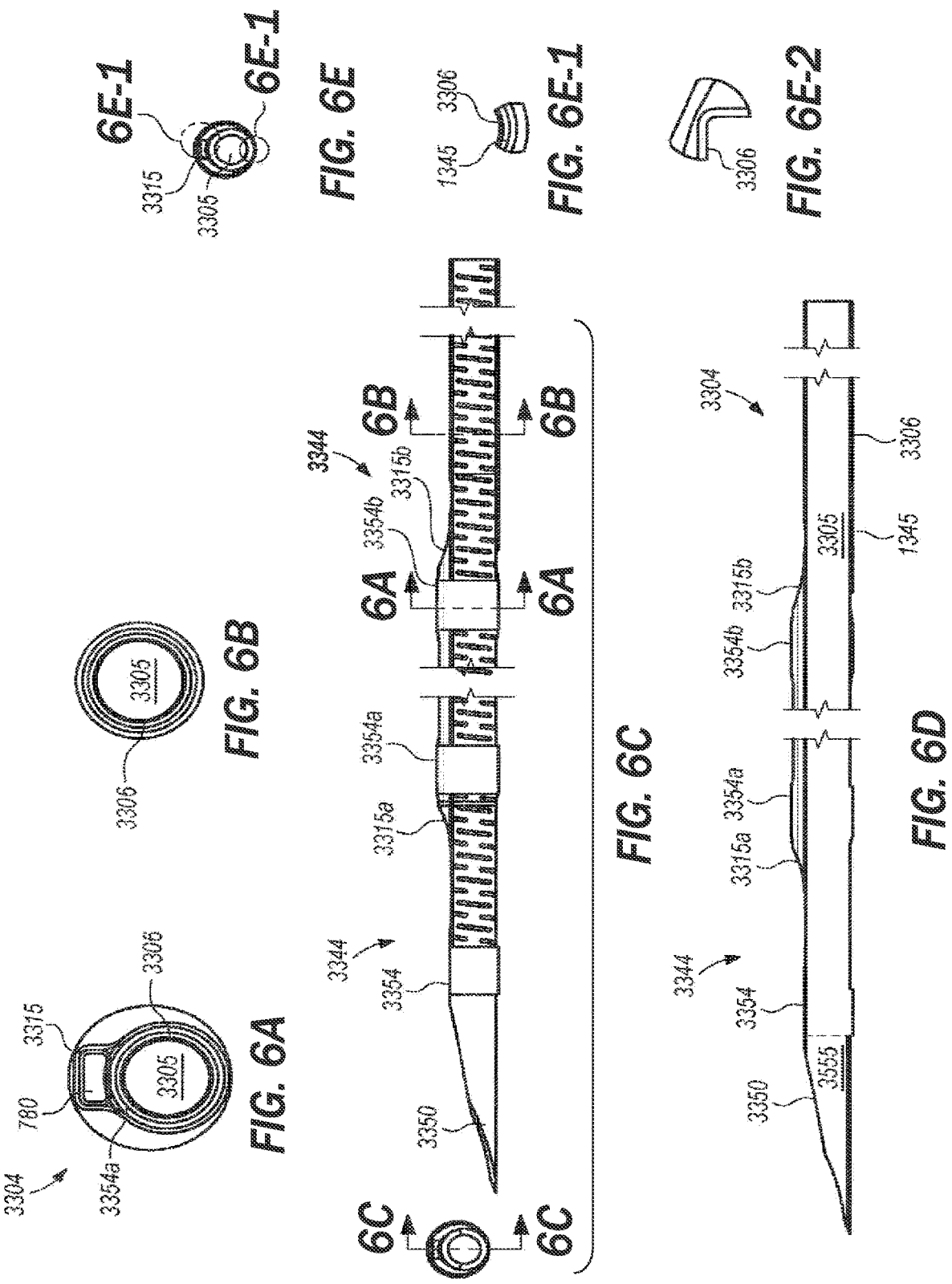

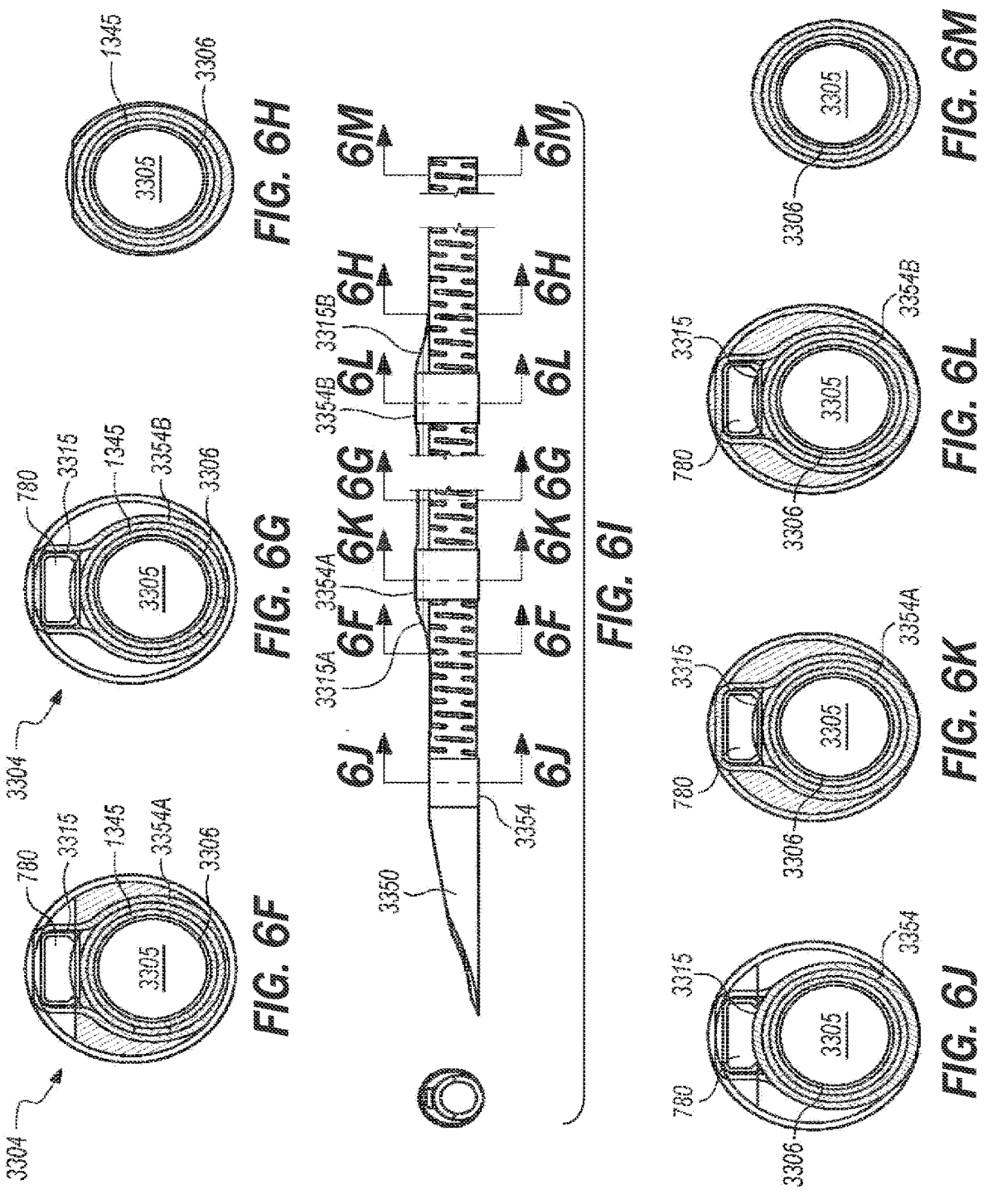

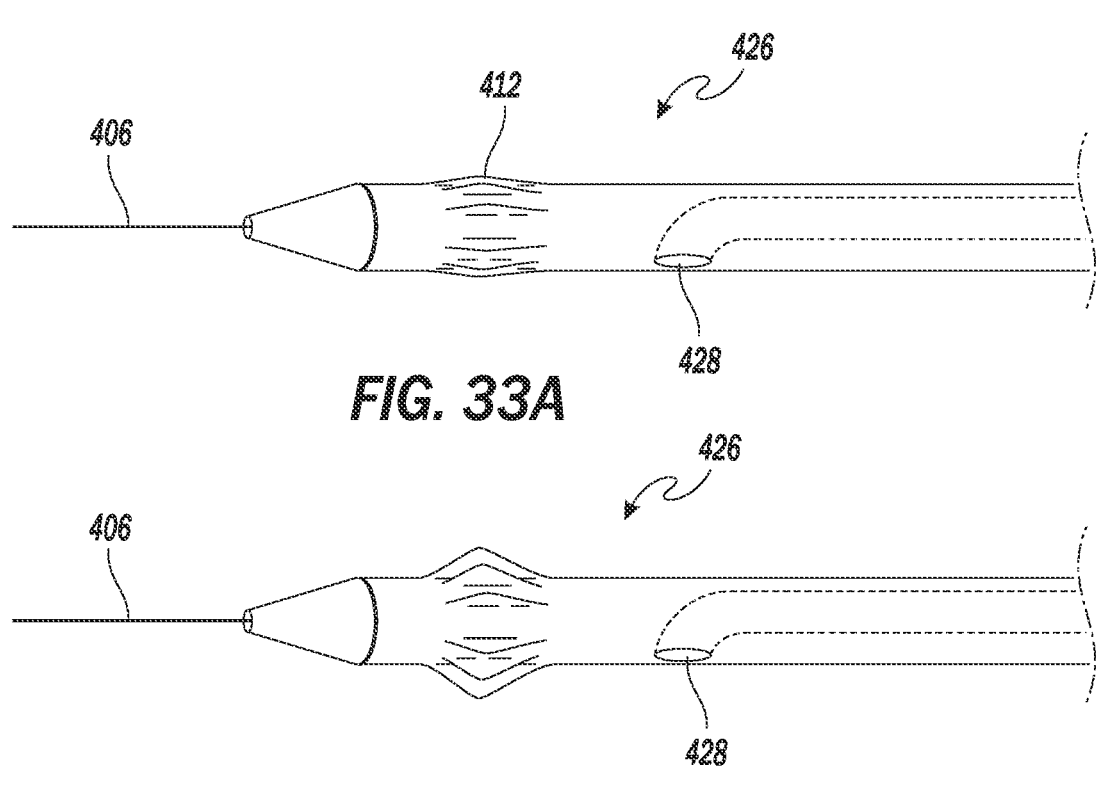
*FIG. 33A*
*FIG. 33B*
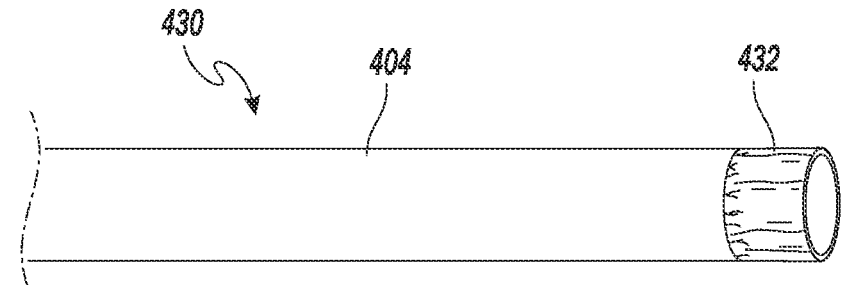
*FIG. 34A*
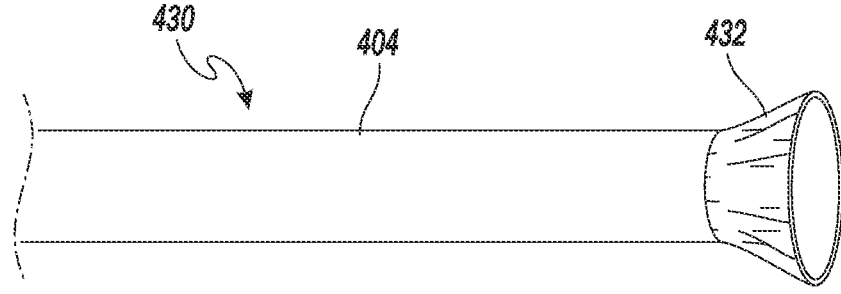
*FIG. 34B*

CATHETER SYSTEMS AND METHODS FOR MEDICAL PROCEDURES USING CATHETERS

RELATED APPLICATIONS

This application is a continuation of International Application No. PCT/US2021/056194, filed Oct. 22, 2021, which claims the benefit of U.S. Provisional Patent Application Ser. No. 63/246,760, filed on Sep. 21, 2021, entitled Catheter Systems and Methods for Medical Procedures using Catheters," U.S. Provisional Patent Application Ser. No. 63/254,737, filed on Oct. 12, 2021, entitled "Systems and Methods for Treating Hydrocephalus," and U.S. Provisional Patent Application Ser. No. 63/104,771, filed on Oct. 23, 2020, entitled "Tumor Toolbox" the contents of all of which are hereby incorporated herein by reference in their entirety.

FIELD OF THE INVENTION

The inventions disclosed herein relate to systems and methods for accessing intracranial subarachnoid spaces and/or draining cerebrospinal fluid (CSF), (e.g., to relieve elevated intracranial pressure or treat communicating and/or obstructive hydrocephalus), using an endovascular approach.

BACKGROUND

Catheters (e.g., micro catheters) are used in a variety of medical procedures for the diagnosis and treatment of conditions and diseases occurring in remote, highly tortuous vascular sites. Typically, a catheter is introduced to the vascular system of a patient at a first location and then is advanced through the patient's vessels until the distal end of the catheter reaches a desired target location.

The process of advancing the catheter often involves applying force proximal of its distal end. Hence, as some conventional catheters advance deeper into the vascular system, it can become difficult to properly maneuver (e.g., push and pull) the distal end of the micro catheter in order to access desired regions. Additionally, advancing the catheter can involve applying torque to a proximal region of the catheter, for example by rotation, to position its distal end for a desired procedure. In this respect, it may be desirable that a catheter exhibit superior hoop strength (which can provide better kink resistance), column strength (which can provide pushability), torqueability (which can provide rotational control), and flexibility (which can provide trackability). Pushability is often understood as the ability to transmit force from the proximal end of the catheter to the distal end of the catheter while limiting kinking. Torqueability can be understood as the ability of the catheter to maintain rotational alignment between the distal and proximal ends when torque is applied to one of the ends. Trackability is often understood as the ability to navigate the catheter through tortuous vasculature.

One example medical procedure in which catheters can be used is in the endovascular treatment of hydrocephalus. Hydrocephalus is one of the most common and important neurosurgical conditions affecting both, children and adults. Hydrocephalus, meaning "water on the brain," refers to the abnormal CSF accumulation in the brain. The excessive intracranial pressure resulting from hydrocephalus can lead to a number of significant symptoms ranging from headache to neurological dysfunction, coma, and death.

Cerebrospinal fluid is a clear, physiologic fluid that bathes the entire nervous system, including the brain and spinal cord. Cells of the choroid plexus present inside the brain ventricles produce CSF. In normal patients, cells within arachnoid granulations reabsorb CSF produced in the choroid plexus. Arachnoid granulations straddle the surface of the intracranial venous drainage system of the brain and reabsorb CSF present in the subarachnoid space into the venous system. Approximately 450 mL to 500 mL of CSF is produced and reabsorbed each day, enabling a steady state volume and pressure in the intracranial compartment of approximately 8-16 cm $H_2O$. This reabsorption pathway has been dubbed the "third circulation," because of its importance to the homeostasis of the central nervous system.

Hydrocephalus occurs most commonly from the impaired reabsorption of CSF, and in rare cases, from its overproduction. The condition of impaired reabsorption is referred to as communicating hydrocephalus. Hydrocephalus can also occur as a result of partial or complete occlusion of one of the CSF pathways, such as the cerebral aqueduct of Sylvius, which leads to a condition called obstructive hydrocephalus.

A positive pressure gradient between the intracranial pressure of the subarachnoid space and the blood pressure of the venous system may contribute to the natural absorption of CSF through arachnoid granulations. For example in non-hydrocephalic individuals, intracranial pressures (ICPs) can range from about 6 cm H20 to about 20 cm H20. ICP greater than 20 cm H20 is considered pathological of hydrocephalus, although ICP in some forms of the disease can be lower than 20 cm H20. Venous blood pressure in the intracranial sinuses and jugular bulb and vein can range from about 4 cm H20 to about 11 cm H20 in non-hydrocephalic patients, and can be slightly elevated in diseased patients. While posture changes in patients, e.g., from supine to upright, affect ICP and venous pressures, the positive pressure gradient between ICP and venous pressure remains relatively constant. Momentary increases in venous pressure greater than ICP, however, can temporarily disturb this gradient, for example, during episodes of coughing, straining, or valsalva.

Normal pressure hydrocephalus (NPH) is one form of communicating hydrocephalus. NPH patients typically exhibit one or more symptoms of gait disturbance, dementia, and urinary incontinence, which can lead to misdiagnosis of the disease. Unlike other forms of communicating hydrocephalus, NPH patients may exhibit little or no increase in ICP. It is believed that the CSF-filled ventricles in the brain enlarge in NPH patients to accommodate the increased volume of CSF in the subarachnoid space. For example, while non-hydrocephalic patients typically have ICPs ranging from about 6 cm H20 to about 20 cm H20, ICPs in NPH patients can range from about 6 cm H20 to about 27 cm H20. It has been suggested that NPH is typically associated with normal intracranial pressures during the day and intermittently increased intracranial pressure at night.

Other conditions characterized by elevated intracranial pressure include pseudotumor cerebri (e.g., benign intracranial hypertension). The elevated ICP of pseudotumor cerebri causes symptoms similar to, but that are not, a brain tumor. Such symptoms can include headache, tinnitus, dizziness, blurred vision or vision loss, and nausea. While most common in obese women 20 to 40 years old, pseudotumor cerebri can affect patients in all age groups.

Prior art techniques for treating communicating hydrocephalus (and in some cases, pseudotumor cerebri and intracranial hypertension) rely on ventriculoperitoneal shunts ("VPS" or "VP shunt" placement), a medical device design introduced more than 60 years ago. VPS placement involves an invasive surgical procedure performed under general anesthesia, typically resulting in hospitalization ranging from two to four days. The surgical procedure typically involves placement of a silicone catheter in the frontal horn of the lateral ventricle of the brain through a burr hole in the skull. The distal portion of the catheter leading from the lateral ventricle is then connected to a pressure or flow-regulated valve, which is placed under the scalp. A separate incision is then made through the abdomen, into the peritoneal cavity, into which the proximal portion of a tubing catheter is placed. The catheter/valve assembly is then connected to the tubing catheter, which is tunneled subcutaneously from the neck to the abdomen.

VPS placement is a very common neurosurgical procedure, with estimates of 55,000-60,000 VPS placements occurring in the U.S. each year. While the placement of a VP shunt is typically well-tolerated by patients and technically straightforward for surgeons, VP shunts are subject to a high rate of failure in treated patients. Complications from VP shunt placement are common with a one-year failure rate of approximately 40% and a two-year shunt failure rate reported as high as 50%. Common complications include catheter obstruction, infection, over-drainage of CSF, and intra-ventricular hemorrhage. Among these complications, infection is one of the most serious, since infection rates in adults are reported between 1.6% and 16.7%. These VPS failures require "shunt revision" surgeries to repair/replace a portion or the entirety of the VP shunt system, with each of these revision surgeries carrying the same risk of general anesthesia, post-operative infection, and associated cost of hospitalization as the initial VPS placement; provided, however that shunt infections can cost significantly more to treat (e.g., three to five times more) compared to initial VP shunt placement. Often these infections require additional hospital stays where the proximal portion of the VPS is externalized and long-term antibiotic therapy is instituted. The rate of failure is a constant consideration by clinicians as they assess patients who may be candidates for VPS placement. Age, existing co-morbidities and other patient-specific factors are weighed against the likelihood of VP shunt failure that is virtually assured during the first 4-5 years following initial VP shunt placement.

As noted above, hydrocephalus can be caused by a physical obstruction preventing CSF flow between the ventricles of the brain and known as obstructive hydrocephalus ("OH"). OH is typically treated through a procedure known as a third ventriculostomy. The invasive procedure requires a burr hole in the skull and use of a trocar to create an opening in the floor of the third ventricle, thereby creating a new pathway for CSF to flow in the brain. Complications include neurovascular injury, hemodynamic alterations, endocrinologic abnormalities, electrolyte imbalances, cerebrospinal fluid leakage, fever, and infection.

Despite significant advances in biomedical technology, instrumentation, and medical devices, there has been little change in the design of basic VPS hardware since its introduction in 1952. There remains a need for minimally invasive treatments in the intracranial subarachnoid space and/or for CSF diversion, for example, to treat communicating and obstructive hydrocephalus.

SUMMARY

Disclosed herein are systems and methods for accessing intracranial subarachnoid spaces and/or draining CSF (e.g., to relieve elevated intracranial pressure or treat communicating and/or obstructive hydrocephalus), or performing other therapeutic and diagnostic procedures, using an endovascular approach. The systems and methods may also include implant devices, such as a shunt, for draining the CSF.

In exemplary embodiments, the system may include an expandable anchor configured for being deployed in a dural venous sinus of the patient at a location distal to a target penetration site located on a curved portion of the IPS wall via a micro catheter, wherein the elongate guide member is coupled to, and extends proximally from, the anchor. Optionally, the system further includes a guide member pusher tool configured for translating the respective guide member and anchor relative to the respective IPS and dural venous sinus (which may be the IPS), for example, through a micro catheter. In various embodiments, the pusher tool comprises a handle having a lumen extending there through, and a tubular body portion coupled to the handle, the tubular body portion having a lumen that is contiguous with or otherwise extends through the handle lumen, the respective handle and tubular body lumens being configured to receive the guide member, wherein the handle is configured to allow selective engagement and release of a portion of the guide member extending proximally through the handle lumen for thereby pushing the guide member, and thus the anchor, distally.

In various embodiments, the guard includes a tubular guard body having a first guard body lumen or recess configured to receive the penetrating element, and a plurality of pull wires, each pull wire having a distal portion fixed within or otherwise attached to the guard body, wherein the pull wires are configured to translate the guard body proximally or distally relative to the delivery catheter so as to at least partially expose or cover, respectively, the penetrating element. The open distal end portion of the guard member preferably has a beveled or tapered portion, and wherein the inner surface feature is located on the beveled or tapered portion. In various embodiments, the inner surface feature of the guard member is formed by at least a partial bead of material applied to, or molded as part of, an inner surface of the guard member.

In various embodiments, the system further comprises an endovascular shunt device, which may also be provided separately from the system. The shunt device includes an elongate shunt body made out of a flexible unreinforced polyurethane-silicone blend or other polymer, and a distal shunt anchor coupled to a distal end of the shunt body, wherein the distal shunt anchor self-expands when advanced out of the delivery catheter lumen. The shunt device further includes one or more cerebrospinal fluid (CSF) intake openings in a distal portion of the shunt that are in fluid communication with a shunt lumen extending through the shunt body, the shunt body comprising one or more longitudinal slits configured to allow egress there through of CSF in the shunt lumen if a fluid pressure within the shunt lumen exceeds a body fluid pressure external of the one or more slits, and wherein a proximal end of the shunt body is fluidly sealed. In an exemplary embodiment, the shunt device includes a tubular connector having a proximal portion secured to a distal end of the shunt body, a distal portion secured to the distal shunt anchor, and an open distal end located within the distal shunt anchor, wherein the one or more CSF intake openings comprise a single CSF intake opening located in the distal end of the tubular connector. The tubular connector may be radiopaque or otherwise have one or more radiopaque elements coupled thereto. In some embodiments, the one or more longitudinal slits in the tubular body portion are configured and dimensioned to achieve a target flow rate of 5 ml of CSF per hour to 15 ml of CSF per hour through the CSF drainage lumen under normal differential pressure conditions between the CP angle cistern and venous system of the patient. In some embodiments, the one or more longitudinal slits in the tubular body portion are configured and dimensioned to allow CSF egress out of the CSF drainage lumen at a pressure differential between the CP angle cistern and the venous system of the patient in a range of 3 mm Hg to 5 mm Hg.

Another disclosed embodiment is directed to a shunt configured for being partially deployed in a dural venous sinus (DVS) of a patient for draining CSF from one or more intracranial subarachnoid spaces (ISAS). The ISAS shunt comprises a distal portion configured for being introduced into, and secured within, a first ISAS of the patient via the DVS and via a second ISAS, the first ISAS and second ISAS containing cerebrospinal fluid (CSF). The shunt further comprises proximal portion configured for being deployed in the venous system of the patient, and a main body portion configured for being disposed within the DVS and second ISAS. The main body portion includes a shunt lumen. The shunt lumen is in fluid communication with one or more CSF intake openings located in the distal portion of the shunt. The main body portion also has one or more CSF intake openings to allow CSF in the second ISAS to flow into the shunt lumen.

The ISAS shunt further includes a CSF outflow opening in fluid communication with the shunt lumen, such that, when the shunt is deployed in the DVS with the distal portion of the shunt disposed within the first ISAS and the main body portion of the shunt disposed within the DVS and second ISAS, CSF flows from the first ISAS and second ISAS through the respective one or more CSF intake openings in the distal shunt portion and shunt body, through the shunt lumen, and CSF outflow opening, respectively, and into the venous system of the patient.

In another aspect of the ISAS shunt, the distal portion of the shunt may be self-expandable from a collapsed delivery configuration to an expanded deployed configuration as it is deployed within the first ISAS. In still another feature of the DVS shunt, the distal portion of the shunt may include a distal anchoring mechanism configured to position the distal portion of the deployed shunt so as to maintain the one or more CSF intake openings separated, apart and/or directed away from an arachnoid layer of the first ISAS, and/or directed away from choroid plexus in the first ISAS.

In still another the aspect, the ISAS shunt may also have a one-way valve located in or coupled to the proximal portion of the shunt. In yet another feature, the shunt lumen and valve may be configured to be dimensioned to achieve a target flow rate of 5 ml of CSF per hour to 15 ml of CSF per hour through the shunt lumen under normal differential pressure conditions between the first ISAS and second ISAS, and the venous system of the patient. In another aspect, the ISAS shunt may also have one or more radiopaque markers disposed in or coupled to the shunt.

Another embodiment disclosed herein is directed to a method for performing an endovascular third ventriculostomy. The method comprises accessing a cerebrospinal fluid-filled ISAS from a DVS of a patient with a delivery catheter. The delivery catheter is configured for penetrating through a wall of the DVS. A tool is navigated through a lumen of the delivery catheter, through the ISAS, and toward a cerebrospinal fluid-filled third ventricle. A floor of the third ventricle penetrated with the tool to allow cerebrospinal fluid to flow from the third ventricle into the ISAS.

In another aspect of the method, the tool may comprise a guidewire with an expandable dissector tip on a distal end of the guidewire. Then, the method further comprises dissecting a hole through an arachnoid layer separating the third ventricle from the ISAS. In still another aspect, the method may also include expanding a circumference of the hole through the arachnoid layer. In yet another aspect, the circumference of the hole through the arachnoid layer may be expanded with an angioplasty balloon.

In another feature of the method, penetrating the floor of the third ventricle in accomplished by making a hole through an arachnoid layer separating the third ventricle from the ISAS.

In another aspect, the method may also include acquiring a 3D reconstruction of the ISAS and using the reconstruction to assist navigating the tool through the ISAS. In another feature, the 3D reconstruction may be acquired by advancing an optical coherence tomography device through the delivery catheter lumen. In addition, the 3D reconstruction may be overlaid with a live fluoroscopy imaging display of the ISAS.

In another aspect of the method, the DVS is an inferior petrosal sinus. In still another aspect of the method, the ISAS is a cerebellopontine angle cistern.

Another embodiment disclosed herein is directed to a method for treating hydrocephalus. The method includes first accessing a first cerebrospinal fluid-filled ISAS from a DVS of a patient with a delivery catheter. The delivery catheter is configured for penetrating through a wall of the DVS. The delivery catheter is navigated through the first ISAS toward a second CSF-filed ISAS. A tissue layer separating the first ISAS and the second ISAS is penetrated with the delivery catheter such that a distal end opening of the delivery catheter accesses the second ISAS. A distal portion of a shunt is then deployed from the distal end opening of the delivery catheter in the second ISAS and a proximal portion of the shunt is positioned in the first ISAS such that a body of the shunt extends through the tissue layer. The shunt includes a CSF inlet in the distal portion, a fluid lumen, and a CSF outlet in the proximal portion. The shunt CSF inlet, lumen, and CSF outlet are all in fluid communication. CSF is drained from the second ISAS through the CSF inlet, lumen, and CSF outlet of the shunt into the first ISAS thereby equalizing a CSF pressure of the second ISAS with a CSF pressure of the first ISAS.

In another aspect, the hydrocephalus method may further include expanding a distal anchoring mechanism coupled to the distal portion of the shunt to secure the shunt distal portion in the second ISAS. In still another aspect, the method may also include expanding a proximal anchoring mechanism coupled to the proximal portion of the shunt to secure the shunt proximal portion in the second ISAS.

In yet another aspect of the hydrocephalus method, the shunt may further comprises a valve at the CSF outlet, and the method further comprises draining CSF from the second ISAS through the valve into the first ISAS.

In still another aspect, the step of deploying the shunt may further comprise advancing the shunt from the distal end opening of the delivery catheter and withdrawing the delivery catheter from the second ISAS through the tissue layer into the first ISAS.

In another aspect, the DVS may be an inferior petrosal sinus. In still another feature of the method, the first ISAS may be a cerebellopontine angle cistern.

In yet another aspect, the step of deploying the distal portion of the shunt in the second ISAS may comprise deploying the shunt distal portion in a lateral ventricle in a brain. In still another aspect, the hydrocephalus method may further comprise deploying the distal portion of the shunt in a frontal horn of the ventricle.

Still another embodiment disclosed herein is a system for endovascular navigation of an ISAS. The system includes a delivery catheter configured for accessing a first cerebrospinal fluid-filled ISAS of a patient. The delivery catheter comprises a penetrating element on a distal end of the catheter, guard disposed over and translatable relative to the penetrating element, and a working lumen that extends from an opening in a proximal portion of the catheter, through a body of the catheter to a distal end opening in the penetrating element. The system also includes a seeker wire comprising an expandable dissector tip on a distal end of the wire, and a microcatheter configured for deployment through the delivery catheter working lumen. The microcatheter includes a lumen extending from an opening in a proximal portion in the catheter to an opening in a distal end of the catheter.

In another aspect of the endovascular navigation system, the delivery catheter may also include a one-way valve in or coupled to the distal end opening of the penetrating element. The valve is configured to resist CSF leaking from the ISAS into the catheter working lumen.

In another aspect, the seeker wire may also include one or more ultrasound or optical coherence tomography sensors for mapping critical anatomical structures within the ISAS. In still another aspect, the microcatheter may also include one or more ultrasound optical coherence tomography sensors for mapping critical anatomical structures within the ISAS.

Yet another embodiment disclosed herein is directed to a method for treating a patient using the endovascular navigation system. In one exemplary embodiment, the method includes advancing the delivery catheter through a venous access location in a patient to a DVS. Then, the guard is retracted and the catheter is advanced through a wall of the DVS to access a first ISAS with the distal end opening of the catheter. The seeker wire is advanced through the delivery catheter working lumen and distal end opening into the first ISAS and navigated through the first ISAS to a membrane separating the first ISAS from a second ISAS. The seeker wire is then advanced through the membrane such that a distal end of the seeker wire is located in the second ISAS of the patient. The microcatheter is advanced over the seeker wire until the distal end opening of the microcatheter is located at a target site in the second ISAS. Then a therapeutic procedure is performed in the second ISAS.

In another aspect of the method, the therapeutic procedure may be delivering a therapeutic agent from the microcatheter into the ISAS. In still another aspect, the therapeutic procedure in the second ISAS may include aspirating blood located in the second ISAS through the microcatheter and out of the patient.

In yet another aspect, the therapeutic procedure may include advancing the seeker wire into a location in the brain parenchyma and removing a portion of the parenchyma with the dissector tip. In still another feature, the method may also include removing a tumor located in the parenchyma.

In still another aspect, the method may further include dissecting into a location in the brain parenchyma with the seeker wire; advancing the microcatheter into the dissection in the parenchyma; and administering a therapeutic agent from the microcatheter into the parenchyma. In another aspect, the therapeutic agent may comprise a composition intended to have a therapeutic effective on all or a portion(s) of a central nervous system of the patient. For example, the therapeutic agent may include one or more of the following: anti-sense RNA; anti-sense oligonucleotides; anti-bodies; antibiotics; anti-vasospasm agents; biosimilars; chemotherapy agents; GABA receptor agonists; an agent for treatment of neurodegenerative diseases including Alzheimer's disease Parkinson's disease and Huntington's disease; and tissue plasminogen activator.

In another aspect, the therapeutic procedure may include administering laser interstitial therapy. Other and further aspects and features of embodiments will become apparent from the ensuing detailed description in view of the accompanying figures.

BRIEF DESCRIPTION OF THE DRAWINGS

FIGS. 6A-M are side, perspective and cross-sectional views of a delivery catheter, constructed according to alternative embodiments of the disclosed inventions;

FIGS. 9-12D are perspective and cross-sectional views of shunt delivery shuttles constructed according to embodiments of the disclosed inventions;

FIGS. 32 and 33A-B are side, perspective views of an endovascular access system having a working port and an expandable tip.

FIGS. 34A-36B are side perspective view of endovascular access systems having a variable inflow zone catheter.

DETAILED DESCRIPTION OF THE ILLUSTRATED EMBODIMENTS

Figure 1:
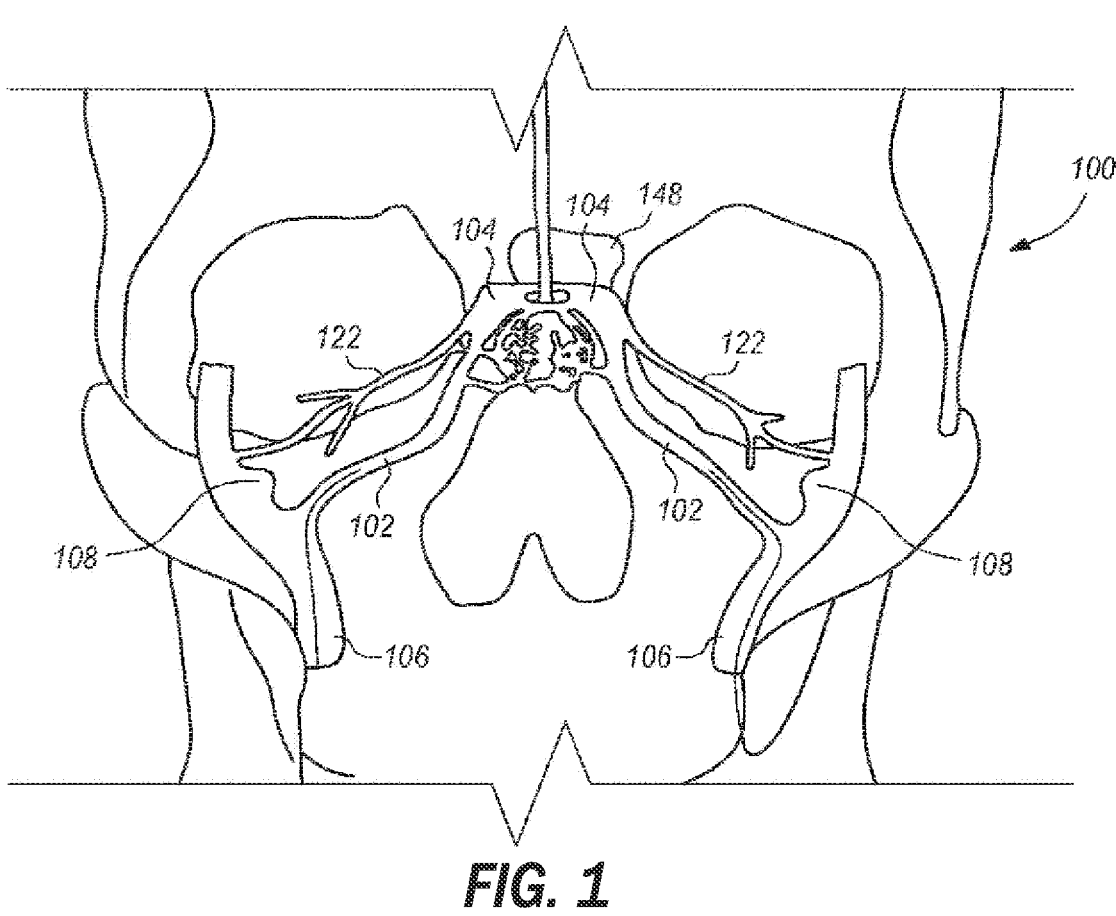
FIG. 1 is a schematic diagram of a head of a human patient.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Micro Catheter Devices

In some aspects, the micro catheters described herein can have varying structural properties along their length to exhibit different performance characteristics for carrying out any of various procedures. The varying structural properties can be defined or determined (e.g., set) by structural properties of a reinforcing member of the micro catheter. In some embodiments, a proximal region of a micro catheter (e.g., where a user handles the micro catheter) can be configured to be stronger (e.g., stiffer, higher pushability, higher torqueability, etc.) than a distal region. In some cases, the micro catheter (e.g., the reinforcing member) can include multiple structural zones, each having different structural properties, which can be set by wall perforations.

Figures 15A, 15B, 15C:
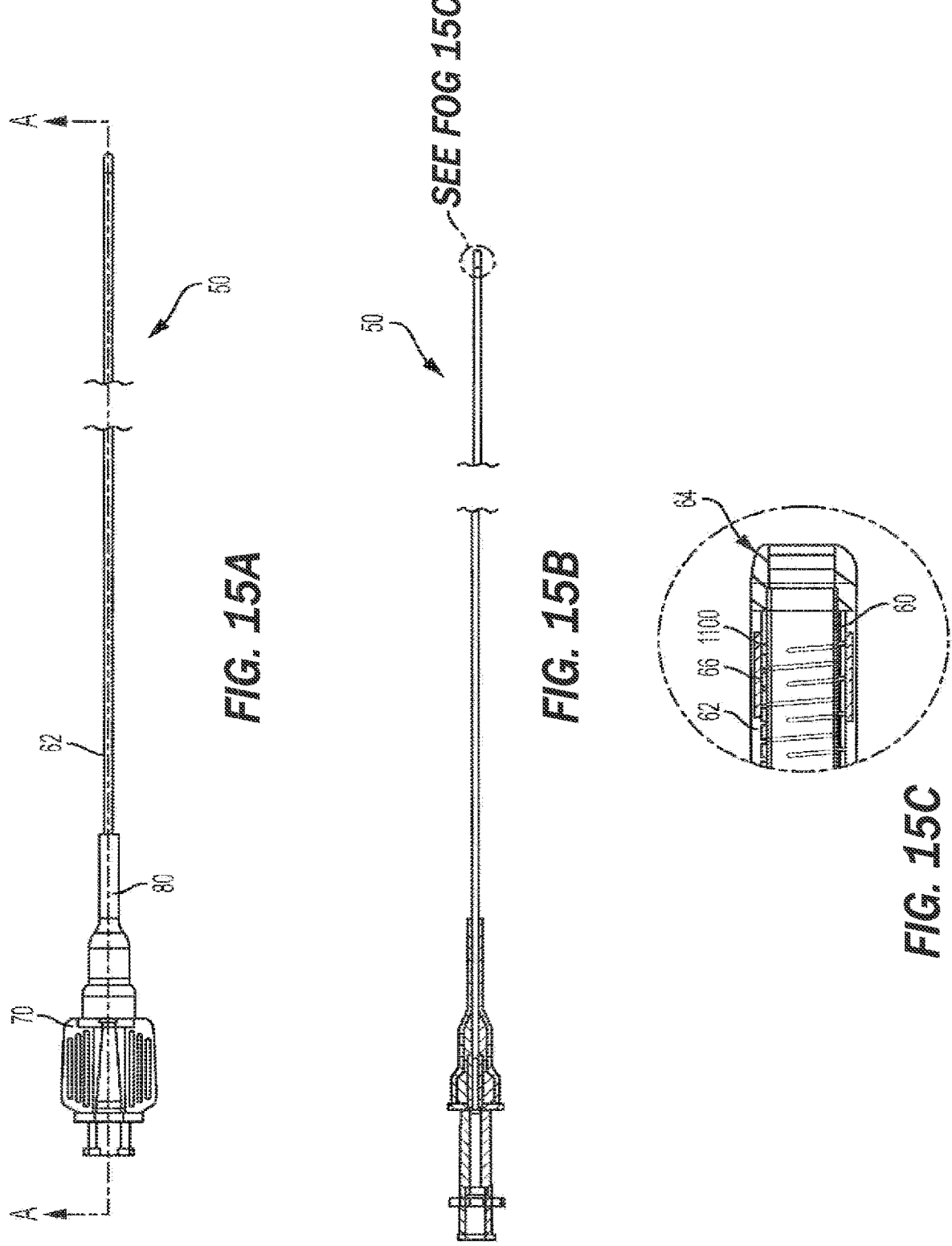
FIGS. 15A-C are side views of an example micro catheter assembly having a structural micro catheter device with different structural properties at different regions along its length.

A micro catheter assembly 50, referring to FIGS. 15A-15C can include a reinforcing structural member (e.g., a reinforcing member, a catheter tube (e.g., micro catheter tube (e.g., a micro catheter tubing core (e.g., a stainless steel or Nitinol hypo tube)))) 1100 that can be lined along its inner surface with one or more liner materials 60. In some cases, the liner material 60 can include any of various flexible and smooth materials, such as a plastic (PTFE) or other material, and can form the inner or working lumen of the catheter assembly 50. The liner 60 can increase lubricity of the assembly. In some examples, the liner material 60 can be thin, for example, having a thickness that is about 0.00075 inches. The micro catheter assembly 50 can also include a jacket material (e.g., an extruded tubing or coating) 62 around the outer surface of the structural component 1100. In some embodiments, the outer jacket 62 surrounds the reinforcing member 1100, with material along its inner surface, outer surface, and inside the cuts. The jacket material can also be a flexible and smooth material, such as PEBAX 6333 or PEBAX 3533, which can be hydrophilically coated, and can define a distal tip 64, which can be tapered. Other examples can include medical grade polymers including, but not limited to, nylon, hytrel, silicone, polyurethane, siliconepolyurethane blends, or other materials. The assembly can include an identifier (e.g., a marker (e.g., a radiopaque marker)) disposed at or near the distal end.

At a proximal end of the assembly 50, the structural component 1100 can be coupled to a hub 70 for handling or connections to other devices. For example, the hub 70 can include a Luer-type connection. In some cases, a strain relief component 80 can be used to connect the structural component 1100 to the hub 70 to limit damage of the flexible structural component 1100 where it is coupled to the substantially rigid hub 70.

Figure 16:
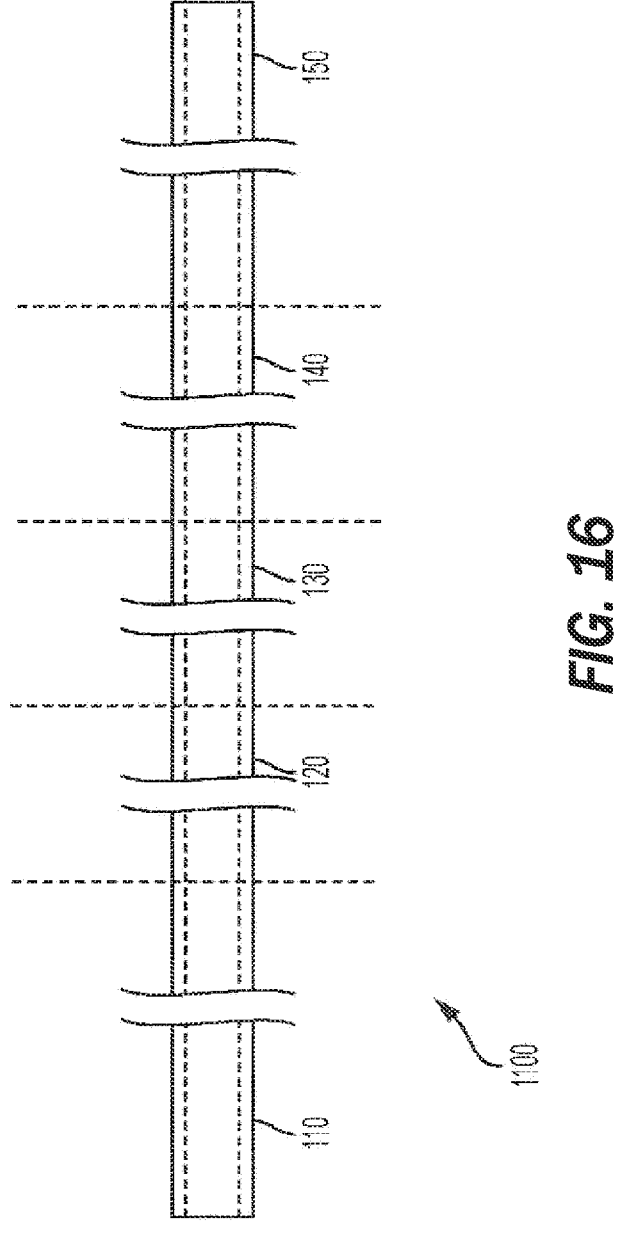
FIG. 16 is a side schematic view of an example structural micro catheter device having different structural properties at different regions along its length.

The varying structural properties of the micro catheter assembly 50 can be caused in large part by structural properties of the reinforcing member 1100. For example, referring to FIG. 16, a reinforcing structural member (e.g., a reinforcing member, a catheter tube (e.g., micro catheter tube (e.g., a micro catheter tubing core))) 1100 can include multiple structural zones 110 (e.g., at its proximal end), 120, 130, 140, 150 (e.g., at its distal end) formed along its length. In the example depicted in FIG. 16, the reinforcing member 1100 has five zones, but other configurations are possible. For example, in some embodiments, the catheter can include 2-50 zones (e.g., 2-10 zones (e.g., 4-6 zones)). The zones can be discrete zones with definite ends where the structural properties of two adjacent zones have discrete end points. However, in some embodiments, zones can be transitional where the properties of one zone transition into the properties of an adjacent zone. In some cases, the structural properties can vary (e.g., vary substantially continuously) along the length of the reinforcing member.

The various zones can be configured so that the reinforcing member 1100 has beneficial material properties for one or more medical procedures. The zones can be of various lengths with respect to the overall length of the reinforcing member. For example, the zones can have the same or different lengths. In some cases, a zone can have a length that is 50% or less (e.g., about 40% or less, about 20% or less, about 15% or less, about 10% or less, about 5% or less, about 2% or less, or about 1% or less) than the overall length of the reinforcing member. The length of the zones can vary between adjacent zones. In some embodiments, a reinforcing member 1100 can include one long zone (e.g., a single zone (e.g., a single zone along 100% of its entire length). In some cases, the reinforcing member 1100 can include a substantially continuously progressive pattern of cuts along its full length.

In some embodiments, the various lengths can be configured based upon the medical environment in which the reinforcing member 1100 and catheter will be deployed, such as having zones at or near its distal end having lengths that are configured to match or otherwise correlate to one or more parts body (e.g., particular venous or arterial locations) around which the catheter needs to be disposed. In some examples, zones closer to the distal end can be shorter than zones closer to the proximal end. In some cases, longer zones at or near the proximal end of the reinforcing member 1100 can help to increase control of the catheter where it will be handled by a user.

Additionally, having shorter zones at or near the distal end of the reinforcing member 1100 can help to create specific desired structural properties along the reinforcing member where the catheter assembly 50 is expected to be used to carry out specific procedures. For example, in some embodiments of the reinforcing member 1100, a first zone 110 can have a length that is about 5% to 50% of the overall length, a second zone 120 can have a length that is about 2% to 20% of the overall length, a third zone 130 can have a length that is about 1% to 20% of the overall length, a fourth zone 140 can have a length that is about 0.25% to 16% of the overall length, and a fifth zone 150 can have a length that is about 0.1% to 12% of the overall length. In some embodiments, a first, proximal zone can be about 36.201 inches, a second zone can be about 8.000 inches, a third zone can be about 5.000 inches, a fourth zone can be about 2.988 inches, and a fifth zone can be about 0.012 inches. In some embodiments, a first, proximal zone can be about 30.547 inches, a second zone can be about 7.874 inches, a third zone can be about 5.906 inches, a fourth zone can be about 7.862 inches, and a fifth zone can be about 0.012 inches.

In some embodiments, the reinforcing member 1100 can include an unmodified region before or after the zones. For example, in some cases, the distal most tip of the reinforcing member can include a short unmodified length. For example, the unmodified region (e.g., along the fifth zone) can include a length of about 0.012 inches of the material used to form the reinforcing member.

The reinforcing member can be made from substantially cylindrical tubing formed of any of various materials, such as metals including stainless steel or Nitinol hypotube. In some cases, the reinforcing member 1100 can also be formed of polymeric materials, such as PEEK or PET. The tubing can be formed to have various inner diameters (ID) or outer diameters (OD), for example, based on the intended size or use of the catheter assembly 50. The inner diameter of the reinforcing member 1100 can be about 0.005 inches to about 0.080 inches. In some examples, the inner diameter can be about 0.014 inches to about 0.038 inches (e.g., about 0.021 inches to about 0.027 inches). The outer diameter can be about 0.016 inches to about 0.100 inches. In some examples, the outer diameter can be about 0.022 inches to about 0.048 inches (e.g., about 0.031 inches to about 0.039 inches).

Figure 17:
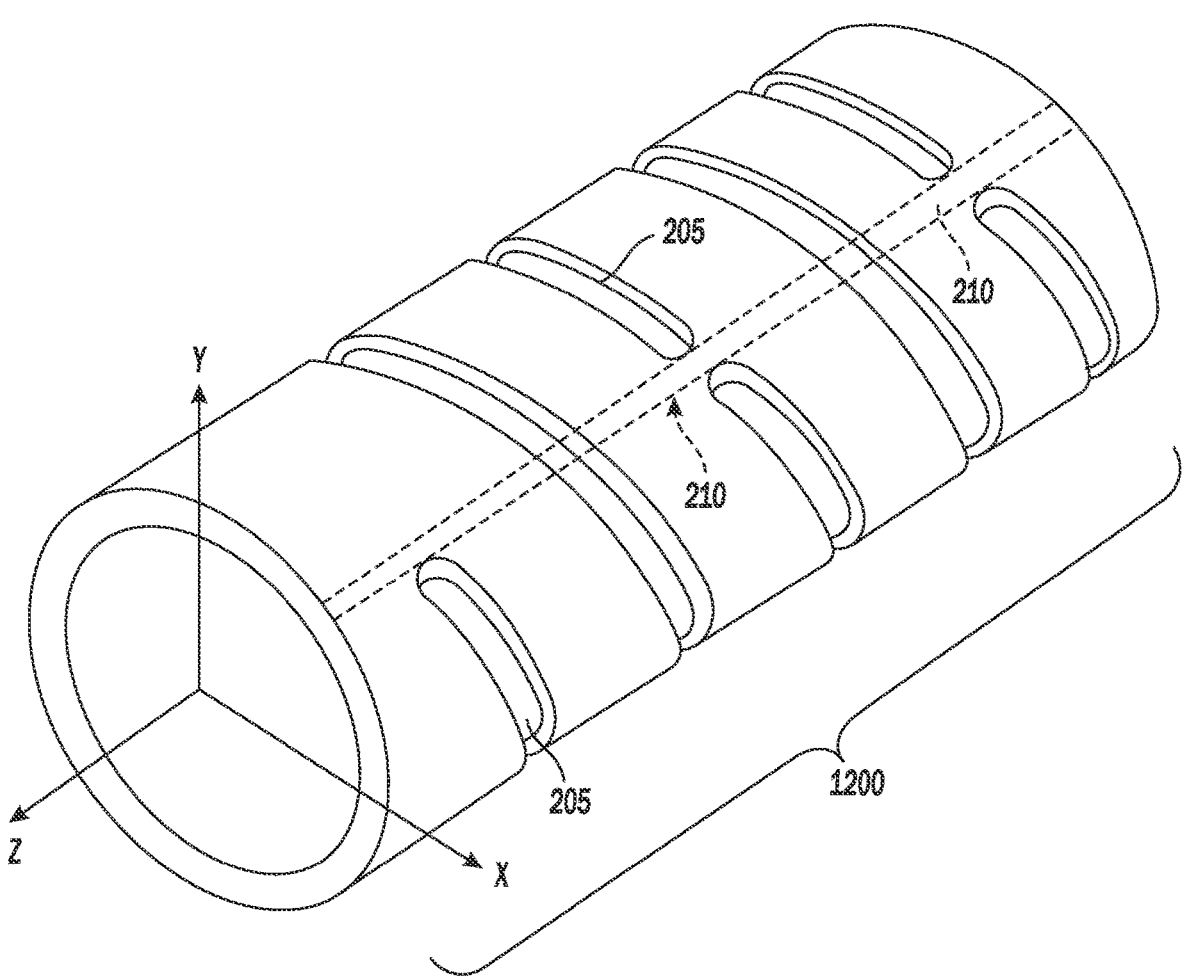
FIG. 17 is a perspective view of an example micro catheter device region having a spiral-like cut formed to alter material properties of the region.

Referring to FIG. 17, in order to set structural properties for the catheter, zones can include a series of one or more cuts (e.g., wall perforations or linear openings) 1200 through the reinforcing member 1100 to generate additional flexibility in the zone. In some examples, the cuts can include one or more spiral-like cuts along the reinforcing member's length. For example, a zone can include an interrupted cut having multiple segments 205 separated by uncut regions 210. The resulting structural properties of the zone can depend on several aspects of the cut, such as pitch of the cut, width of the cut formed, cut balance, cuts per rotation, a size of a seam of interruptions, as well as other aspects. In some embodiments, multiple zones or regions could be formed by one or more reinforcing elements disposed along the length of a catheter, for example, in examples where discrete sections of reinforcement are desired. As used herein, different regions formed of discrete reinforcing member lengths can include the various features described herein with respect to different regions. Additionally, or alternatively, in some examples, reinforcing member sections can be used along only one or more portion of a catheter length, transitioning then to unreinforced or otherwise reinforced portions of a catheter.

Uses of the Micro Catheters in Medical Procedures

FIG. 1 is a schematic diagram showing the head 100 of a human patient. Within each side of the patient's head, an inferior petrosal sinus (IPS) 102 connects a cavernous sinus (CS) 104 to a jugular vein 106 and/or a jugular bulb 108. For clarity, the acronym "IPS" is used herein to refer generally to the inferior petrosal sinus and more particularly to the interior space (or lumen) of the inferior petrosal sinus. The IPS 102 facilitates drainage of venous blood into the jugular veins 106. In some patients, the junction of the IPS 102 and the jugular vein 106 occurs within the jugular bulb 108. However, in other patients, this junction can occur at other locations in the jugular vein 106. Moreover, while the IPS 102 in FIG. 1 is a single sinus passageway, in some patients the IPS can be a plexus of separate channels that connect the CS to jugular vein 106 (not shown) and/or jugular bulb 108.

Embodiments of the disclosed inventions are described with respect to a target penetration site in the IPS 102 to access the CSF-filled subarachnoid space (e.g., CP angle cistern 138). Alternatively, other target penetration sites throughout the dural venous sinuses can be used to access the CSF-filled subarachnoid space. The delivery assemblies and CSF shunts described herein can access the target penetration site in the IPS 102 through a venous access location in the patient. The delivery assemblies and shunts described herein can penetrate the dura mater IPS wall 114 and the arachnoid layer 115 to access the CP angle cistern 138 and other locations within the ISAS (e.g., third ventricle, lateral ventricle) from within a dural venous sinus (e.g., superior petrosal sinus 122 in FIG. 1) for delivery and implantation of the shunt at the target site. The dura mater IPS wall 114 is also referred to herein as the dura IPS or sinus wall 114, or simply as the IPS wall 114. The SPS is a small diameter venous sinus that connects from the sigmoid sinus (distally located to jugular bulb 108) to the cavernous sinus 104 (1). Further, the delivery assemblies and shunts described herein can be advanced through the IPS 102 and into the cavernous sinus 104, so that an anastomosis (not shown) can be created in the upper portion or roof of the cavernous sinus 104 to access the CSP-filled suprasellar cistern 148, shown in 1, for implantation of the shunt at such target site. Whether penetration to access a target site, deployment and implantation of a shunt occurs from the lumen of the SPS or cavernous sinus to access CSF in the subarachnoid space, the embodiments of the inventions described herein provide a conduit for CSF to flow from the subarachnoid space into the jugular bulb 108, jugular vein 106, and/or the superior vena cava-right atrium junction (not shown).

Figure 2A:
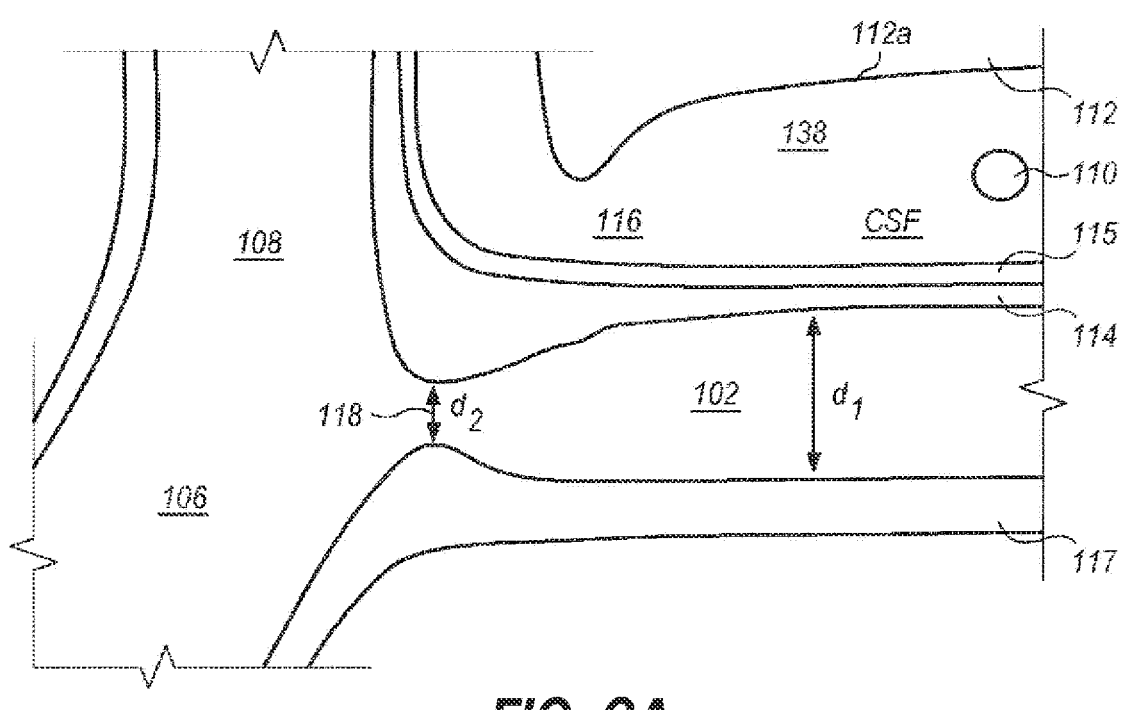
FIG. 2A-D are cross-sectional views of a portion of the head of a human patient.

FIG. 2A shows a cross-sectional view of a portion of head 100, including IPS 102, jugular vein 106, and jugular bulb 108. In addition, basilar artery 110, brain stem 112, pia 112a, and IPS wall 114 are also shown in FIG. 2A. The IPS is a relatively small diameter intracranial venous sinus that facilitates drainage of cerebral venous blood into the jugular vein; the IPS is formed by a cylindrical layer of dura mater, typically about 0.9 mm to 1.1 mm thick for the portion of IPS wall 114 shown in FIG. 2A, which creates a hollow lumen through which blood flows. In the cross-section view of FIG. 2A, the hollow lumen of the IPS resides between upper IPS wall 114 and a lower IPS wall 117, also comprised of dura mater; the IPS itself lies in a bony groove or channel in the clivus bone (not shown) beneath IPS wall 117 in FIG. 2A.

A cross-section of the IPS 102 orthogonal to the plane depicted in FIG. 2A would show that the cylindrical layer of dura mater forming IPS 102 is surrounded by bone for about 270° of its circumference with the remaining portion of the IPS circumference (i.e., IPS wall 114 in FIGS. 2A-B) covered by arachnoid matter 115 and facing CP angle cistern 138. Arachnoid mater 115 (also referred to herein as the arachnoid layer) is a delicate and avascular layer, typically about 0.05 mm to 0.15 mm thick, that lies in direct contact with the dura mater comprising the exterior of IPS wall 114; arachnoid layer 115 is separated from the pia mater surrounding brain stem 112 by the CSF-filled subarachnoid space 116 (e.g., CP angle cistern 138). The lower portion of the IPS 102, opposite to the IPS wall 114 is the IPS wall 117 formed by dura mater that sits in a channel in the clivus bone (not shown).

It should be appreciated that for the embodiments of the disclosed inventions, the methods and devices are configured to create an anastomosis via an endovascular approach by piercing or penetrating from within the hollow IPS 102 to pass through the dura of IPS wall 114, and continue penetrating through the arachnoid layer 115 until reaching the CSF-filled subarachnoid space 116 (e.g., CP angle cistern 138). For ease of illustration, it should be appreciated that the arachnoid matter 115 covering the IPS wall 114 is present, although, not shown in certain figures.

The diameter $d_1$ of IPS 102 is approximately 3 mm but can range from approximately 0.5 mm to about 6 mm. As shown in FIG. 2A, at the junction 118 between the IPS 102 and the jugular bulb 108 and/or jugular vein 106, the diameter $d_2$ of the IPS 102 can narrow. For example, $d_2$ is approximately 2 mm, but can be as small as about 0.5 mm. The length of the IPS 102 from the junction 118 with the jugular vein 106 to the cavernous sinus 104 (shown in FIG. 1) is approximately in a range between 3.5 cm to 4 cm.

Figure 2B:
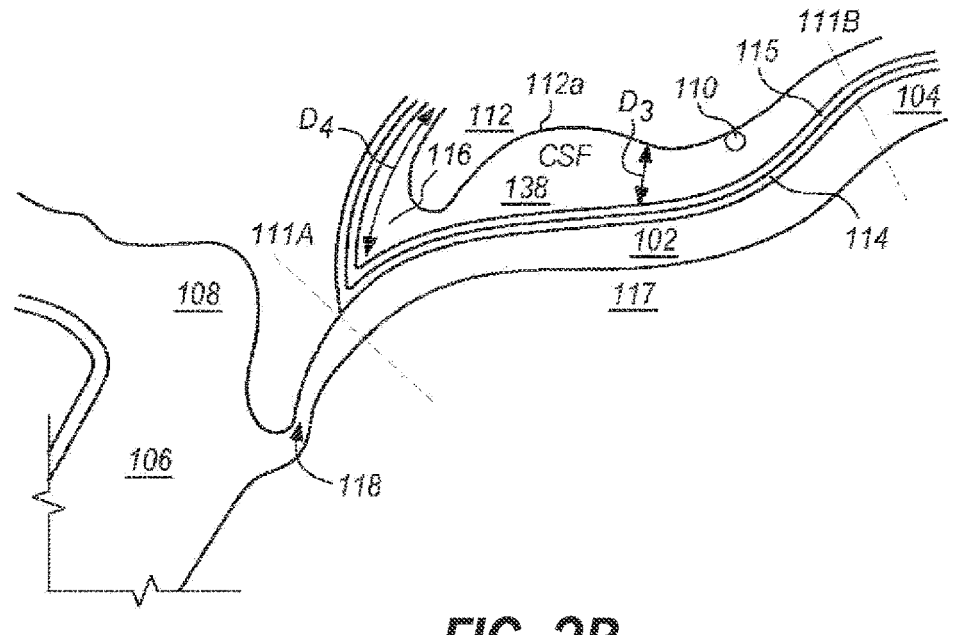

In many patients, the IPS 102 is coupled to the jugular vein 106 at a location disposed below of the jugular bulb 108, depicted as junction 118, shown in FIG. 2B. The IPS 102 extends distally from the junction 118 in the medial wall of the jugular vein 106, past the 9th cranial nerve 111A and jugular tubercle (not shown) while curving rostral-medially through a first curved portion 102A shown in FIG. 2C, and then further curving medial-superiorly through a second curved portion 102B shown in FIG. 2C before connecting at the connection point 111B with the cavernous sinus (CS) 104. The IPS 102 extends distally from the junction 118 through a curvature of approximately 45° to 100° in the first and second curved portions 102A and 102B until the IPS 102 connects with the CS 104. The CSF-filled CP angle cistern 138 lies immediately above the curved portion of the IPS 102.

Figure 2C:
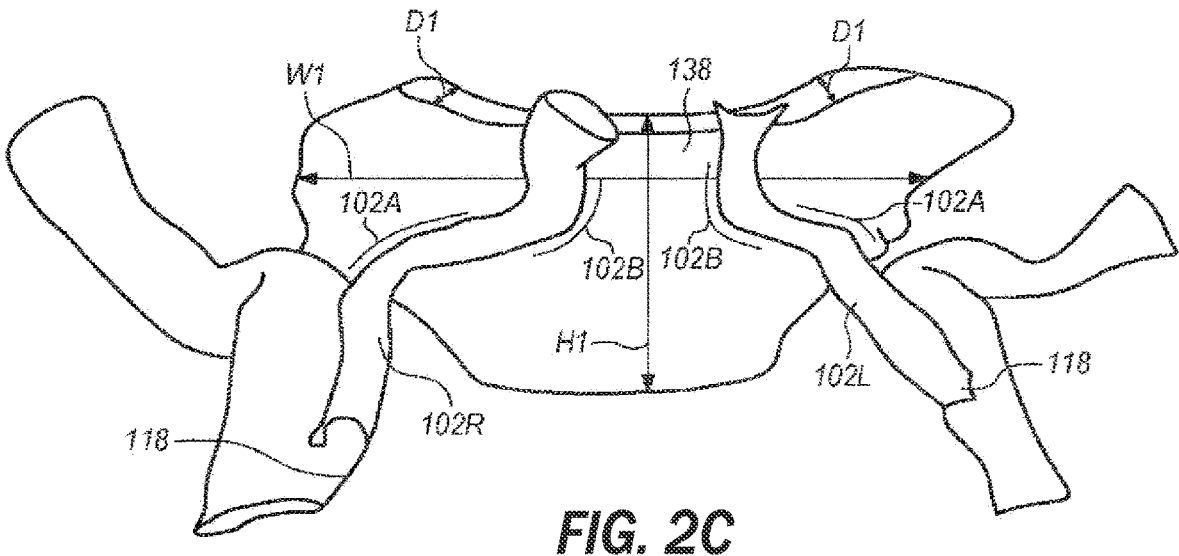
Figures 2D, 3A, 3B, 3C, 3D:
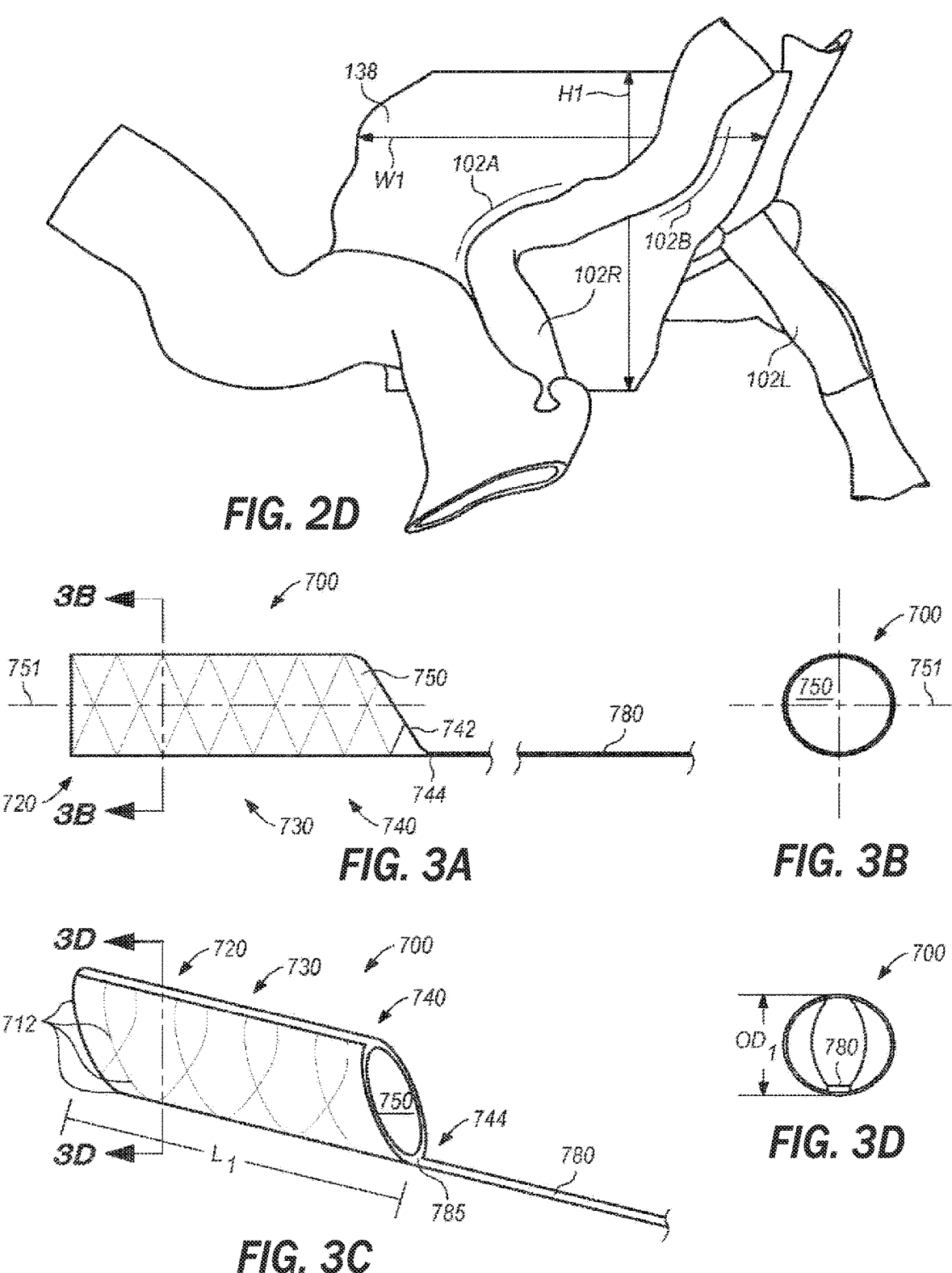
FIG. 3A-J are side, perspective and cross-sectional views of an anchor and elongate guide member, according embodiments of the disclosed inventions.

Anatomical features of CP angle cistern 138 provide a large extent of unobstructed, CSF-filled subarachnoid space to accommodate a penetrating element and shunt distal anchoring mechanism as further described herein. In addition, access to CP angle cistern 138 facilitates access to other locations in the intracranial subarachnoid space. FIG. 2C shows a portion of CP angle cistern 138 and the relative proximity of the cistern to a patient's right IPS 102R and left IPS 102L. Beyond the lateral boundaries of the cistern depicted in the figure, the CSF filled subarachnoid space continues circumferentially around the base of the skull, albeit with a lesser extent of CSF space than in CP angle cistern 138. CP angle cistern 138 comprises a depth of free CSF space labelled D1 in FIG. 2C between the skull base and brainstem (not shown, but, e.g., between the anterior portions of the occipital and sphenoid bones and the brain stem). CP angle cistern 138 also comprises a height of free CSF space labelled H1 in FIG. 2C that extends superiorly along the base of the skull (not shown, but extending superiorly from the jugular foramen). CP angle cistern 138 further comprises a width extent of free space labelled W1 in FIG. 2C (e.g., extent of free CSF space extending laterally between the right and left jugular foramina, not depicted). CP angle cistern 138 contains a relatively large volume of CSF, as defined by the exemplary depth D1, height H1, and width W1 dimensions. FIG. 2D shows an alternative view of the same patient anatomy depicted in FIG. 2C, albeit with the D1 cistern dimension portions of left IPS 102L obscured by the view.

As shown in FIGS. 1 and 2C, most patients have two IPS 102 and two jugular veins 106 (left and right). In a very small percentage of patients (e.g., less than 1%), there is no connection between one IPS and the corresponding jugular vein. It is highly unlikely, however, that any given patient will lack connections to the corresponding jugular veins on both left and right IPS.

Subarachnoid spaces are naturally occurring separations between the pia mater and the arachnoid layer where the CSF pools. Typically, the CSF is passed into a subarachnoid space over the cerebral hemispheres and then into the venous system by arachnoid granulations. The subarachnoid space 116 in FIG. 2A corresponds to a cerebellopontine (CP) angle cistern 138, which acts as a reservoir for CSF. In patients with hydrocephalus, a build-up of CSF within the CP angle cistern 138 (in addition to other cisterns and the brain ventricles) can occur, for example, if patients lack properly functioning arachnoid granulations. If the excess CSF is not removed, the resulting excess intracranial pressure can lead to symptoms such as headache, neurological dysfunction, coma, and even death.

Figure 3E:
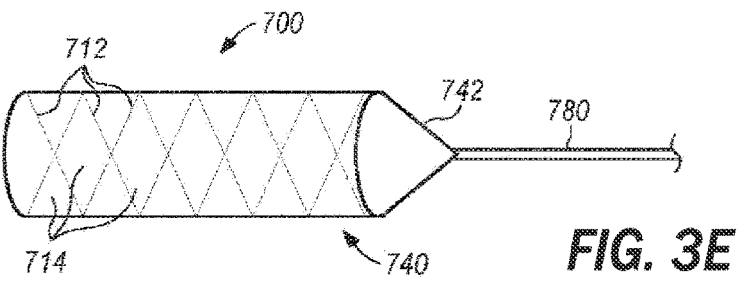
Figure 3F:
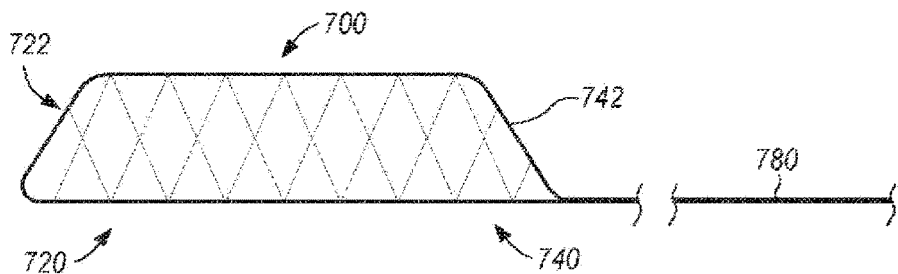
Figure 3G:
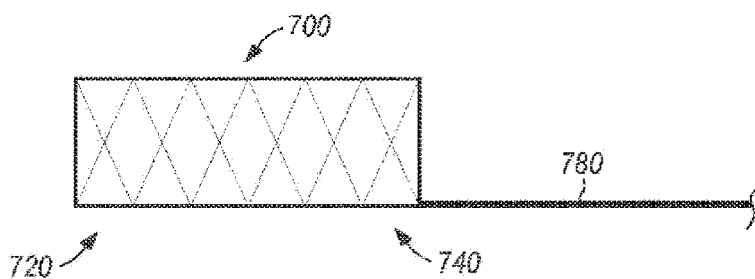
Figure 3H:
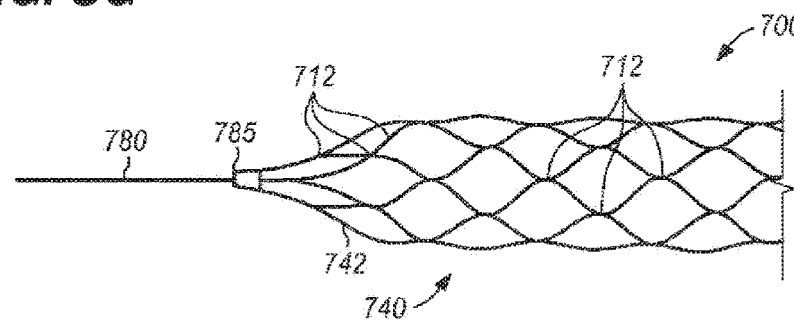
Figure 3I:
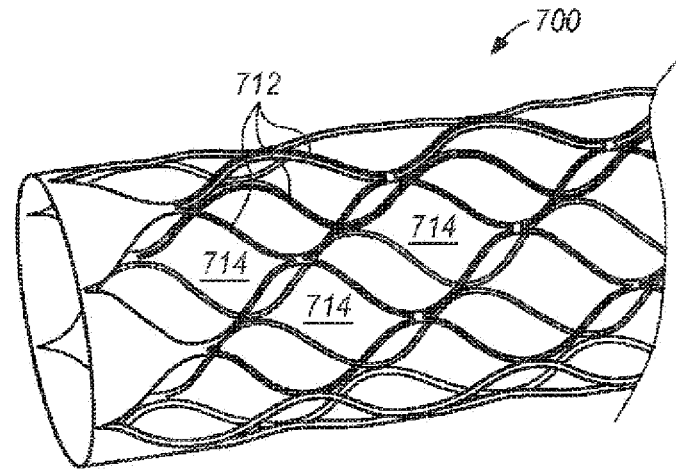
Figure 3J:
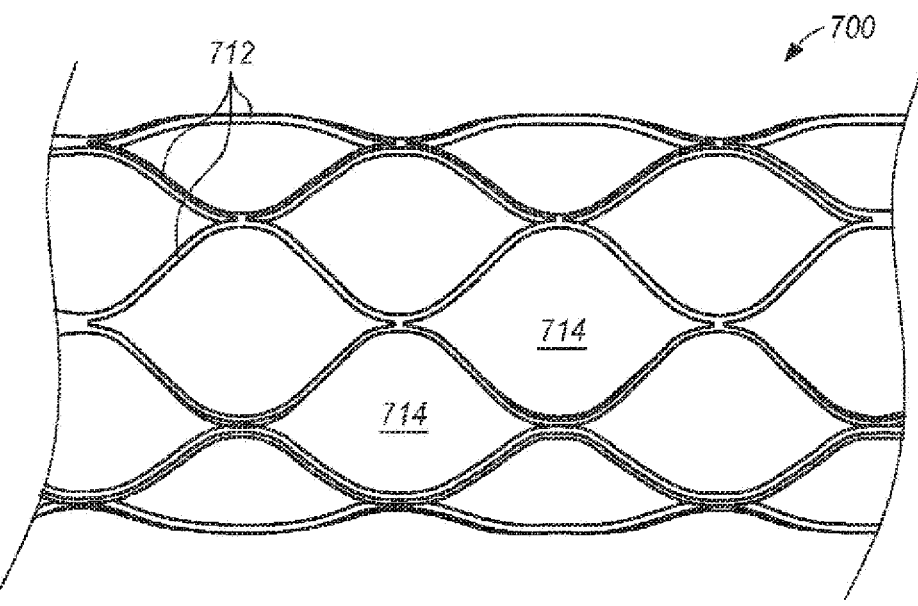

FIGS. 3A-J illustrate exemplary anchor 700, according to the embodiments of the disclosed inventions. The anchor 700 comprises a proximal portion 740, a middle or body portion 730, a distal portion 720 (FIG. 3A), and a lumen 750 extending therebetween (FIG. 3A-B). The proximal portion 740 of FIGS. 3A, 3C, 3E, 3F includes a beveled or tapered proximal section 742. The anchor 700 further comprises an elongate guide member 780 coupled to the proximal portion 740 and/or beveled/tapered proximal section 742. As shown in FIGS. 3A, 3C and 3F, the beveled/tapered proximal section 742 is offset, as the taper transitions to the bottom of proximal portion 740 and the elongate guide member 780. Alternatively, the beveled/tapered proximal section 742 may be symmetrical having the elongate guide member 780 centrally disposed, as shown in FIGS. 3E and 3H. Additionally, the distal portion 720 of the anchor 700 may include a beveled/tapered distal section 742, as shown in FIG. 3F. The proximal portion 740 and distal portion 720 of the anchor 700 may taper at a variety of suitable angles. The proximal portion 740 of the anchor 700 may comprise a strut or plurality of struts 712 directly or indirectly coupled to the elongate guide member 780 (e.g., FIG. 3E, 3H). In an alternative embodiment, the anchor 700 proximal portion 740 and distal portion 720 terminates at approximately 90° angle (i.e., without tapering), as shown in FIG. 3G.

The anchor 700 may be composed of suitable materials, such as, platinum, Nitinol®, gold or other biocompatible metal and/or polymeric materials, for example, silicon, or combinations thereof. In some embodiments, the anchor 700 may include materials that are compatible with magnetic resonance imaging and have radiopacity sufficient to allow the use of known imaging techniques. In some embodiments, the anchor 700 is composed of shape memory, self-expandable and biocompatible materials, such as Nitinol®, or other super-elastic alloys, stainless steel, or cobalt chromium, and comprises a stent-like configuration. In other embodiments, the anchor 700 may include other suitable configurations, such as tubular prosthesis, flow diverter, clot retriever, or the like. Alternatively, the anchor 700 can be composed of magnesium, zinc, or other bio-absorbable or dissolvable components.

FIGS. 4A-I depict an embodiment of a delivery assembly 300 comprising delivery catheter 3304 and penetrating element guard or guard member 4000. The guard member 4000 covers the penetrating element 3350 during navigation of the delivery catheter 3304 (FIG. 4A) through the patient's vasculature to the target penetration site on IPS wall 114 and during withdrawal of delivery catheter 3304 after shunt deployment, thereby preventing inadvertent puncture or damage to other components of delivery assembly (e.g., guide catheter) and the patient's vasculature. As will be further described below, the clinician can actuate a pull wire 4010 to retract guard 4000 proximally and expose the penetrating element 3350 to the dura of IPS wall 114 prior to the penetration step of the shunt implant procedure and, optionally, then re-cover the penetrating element 3350 after the penetration step (e.g., after distal anchoring mechanism 229 of the shunt has been deployed). Radiopaque markers located on the guard 4000 and delivery catheter 3304 provide an indication of whether the guard has been retracted and penetrating element 3350 is exposed or the guard remains in a delivery configuration, covering the penetrating element 3350 for navigation through the patient's vasculature, as will be further described below.

Figure 4A:
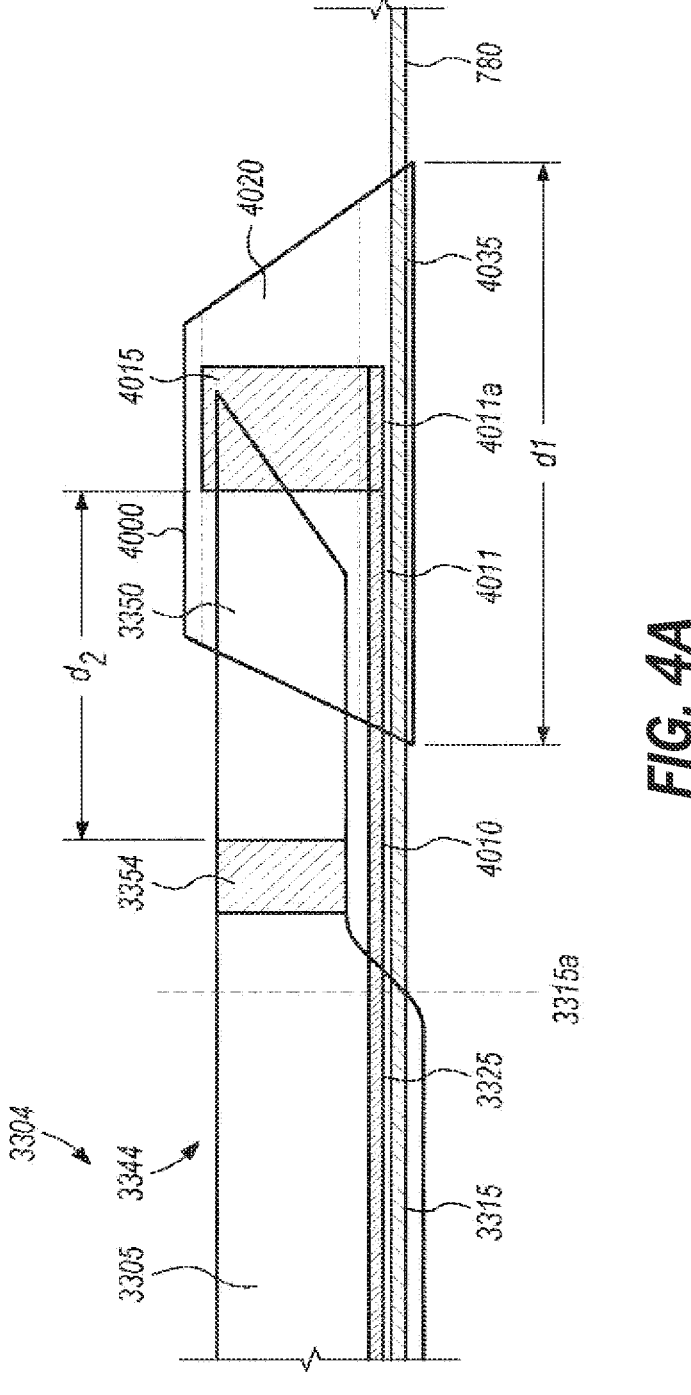
FIGS. 4A-I are perspective and cross-sectional views of a delivery assembly having a penetrating element guard, according to embodiments of the disclosed inventions.

With reference to FIG. 4A, the distal portion 3344 of delivery catheter 3304 comprises penetrating element 3350 and a radiopaque marker 3354. As previously described, delivery catheter 3304 includes a first lumen 3315 to accommodate elongate guide member 780 and a second lumen 3305 to accommodate a shunt 2200 (not shown) or smaller catheter or endovascular device (not shown). The guard member 4000 comprises a pull wire 4010, the pull wire 4010 having a distal portion 4011 attached to a guard body 4000, where the pull wire 4010 is configured to translate the guard body 4000 proximally or distally relative to the shunt delivery catheter 3304 so as to at least partially expose or cover, respectively, the penetrating element 3350. The distal portion 4011 of pull wire 4010 is embedded or encased within guard 4000 (as will be further described below) and includes an attachment point 4011a (e.g., a weld) to radiopaque marker 4015 also embedded within guard 4000 (as will be further described below). The guard 4000 further comprises a first lumen 4020 configured to receive the penetrating element 3350 and allows the guard 4000 to retract proximally (direction of left-hand arrow d2 in FIG. 4A) over the penetrating element 3350 and distal portion of 3344 of delivery catheter and distally (e.g., to re-cover penetrating element 3350, direction of right-hand arrow d2 in FIG. 4A) via pull wire 4010. The enlarged circumference in the distal portion 3344 of delivery catheter 3304 at interface point 3315a where the elongate guide member 780 enters the first lumen 3315 of the delivery catheter prevents guard 4000 from retracting further proximally over the delivery catheter. Guard 4000 can advance distally, via pull wire 4010 and as will be further described below, to re-cover penetrating element 3350. As shown in FIG. 4A, the shunt delivery catheter 3304 includes a third lumen 3325 that extends throughout the length of the delivery catheter, from the distal portion 3344 to the proximal portion 3342; third lumen 3325 accommodates pull wire 4010 of guard 4000.

Figures 4B, 4C, 4D:
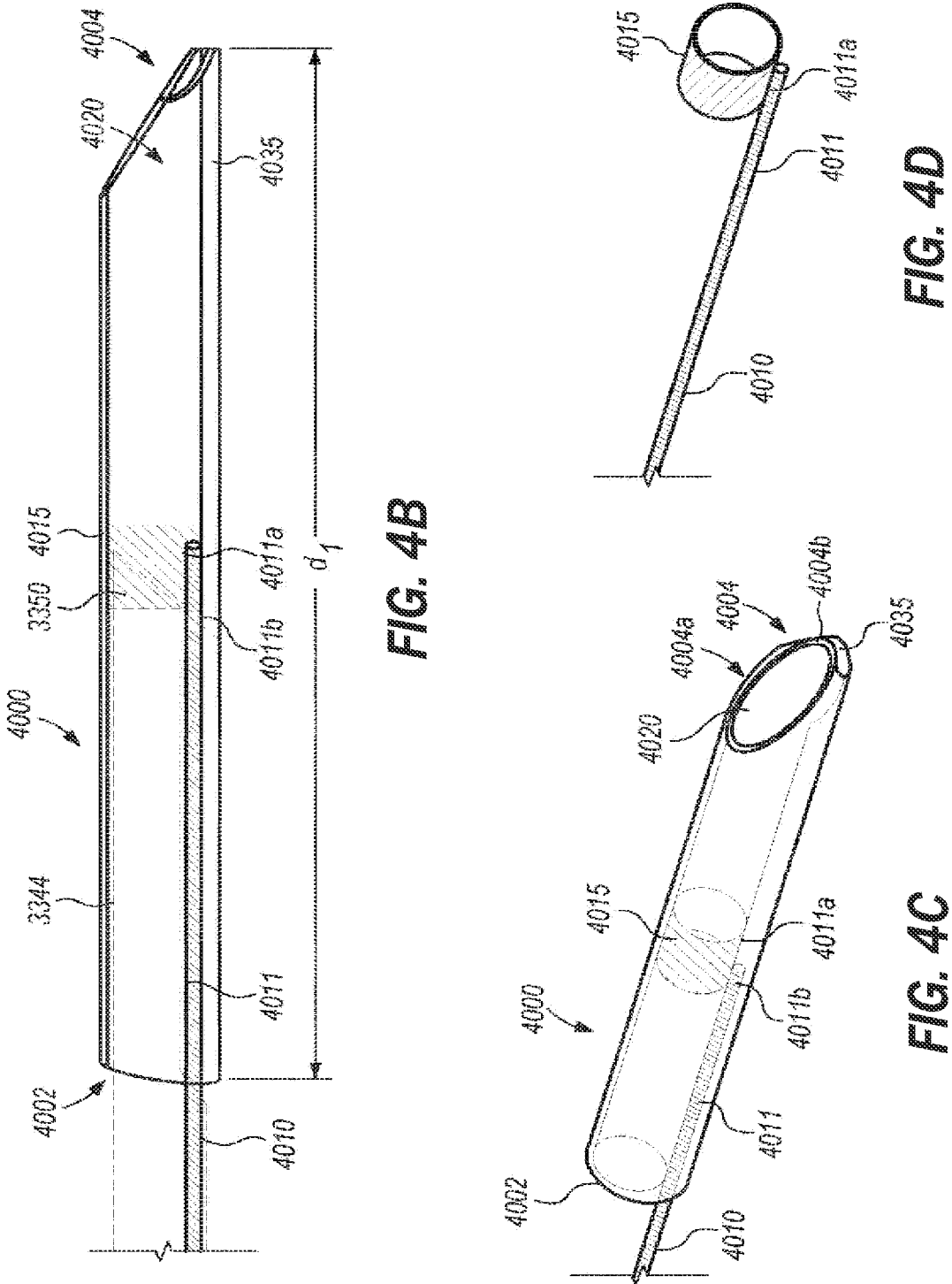

FIGS. 4B and 4C show cross section and perspective views, respectively, of penetrating element guard or guard member 4000. FIG. 4B depicts a guard member 4000 in a delivery configuration with respect to the distal portion 3344 of delivery catheter 3304 (represented by dashed lines in the figure), covering penetrating element 3350. Penetrating element 3350 is positioned within lumen 4020 of the guard 400 and inside of radiopaque marker 4015 embedded or encapsulated within the walls of guard 4000 (as will be further described below). The guard member 4000 can be approximately 0.5" (1.27 cm) long or other suitable dimensions sufficient to cover penetrating element 3350 on the distal portion 3344 of the delivery catheter. The guard lumen 4020 is sized to allow guard 4000 to retract proximally over the penetrating element 3350 and distal portion 3344 of the delivery catheter, indicated by the direction of the left-hand arrow d2 shown in FIG. 4A. For example, the inner diameter of guard lumen 4020 can be approximately 0.0385" (0.09779 cm).

Marker 4015 comprises a cylindrical profile (as can be seen in FIGS. 4B-D and 4G) such that penetrating element 3350 can reside inside of marker 4015 and the guard first lumen 4020 as depicted in FIG. 4A; the alloy material of marker 4015 shields the concentrically disposed penetrating element 3350 and can prevent the penetrating element from inadvertently puncturing through the guard 4000 when the distal portion of 3344 of delivery catheter 3304 bends as the clinician navigates the delivery assembly 300 through tortuous anatomy to the target penetration site along IPS wall 114. The distal portion 4004 of the guard 4000 has a beveled/tapered edge, as shown in FIGS. 4B and 4C. The bevel/taper facilitates access to narrow or tortuous vasculature as the clinician navigates the delivery assembly distally beyond the inferior vena cava (e.g., to access and navigate through junction 118 of jugular vein 106 and IPS 102). The guard 4000 may comprise a second lumen 4035 to accommodate elongate guide member 780 as shown in FIG. 4C. The delivery assembly 300 comprising delivery catheter 3304 and guard 4000 can advance along the elongate guide member 780 distally, toward the target penetration site; that is, the guide member 780 passes through second lumen 4035 of the guard 4000 and lumen 3315 of delivery catheter 3304 to assist delivery catheter navigation through the patient's vasculature.

FIG. 4D depicts the pull wire 4010 and radiopaque marker 4015 subassembly of guard 4000. Pull wire 4010 can comprise PFTE-coated stainless steel or other suitable materials. The diameter of pull wire 4010 can range from about 0.003" to 0.012" (0.0762 mm to 0.3048 mm). While pull wire 4010 depicted in FIG. 4B-D has a circular cross-sectional profile, other pull wire embodiments can include non-circular cross-sectional profiles (e.g., rectangular, crescent). The PTFE coating on pull wire 4010 increases the lubricity of the wire within the third lumen 3325 of delivery catheter 3304, thereby facilitating smooth proximal and distal actuation of guard 4000 to expose and re-cover penetrating element 3350 (not shown in FIG. 4D). Radiopaque marker 4015 can comprise platinum-iridium 90/10 alloy or other suitable materials that provide sufficient radiopacity and allow for a connection point 4011a between the marker and distal portion 4011 of pull wire 4010. The inner diameter of marker 4015 can be 0.0385' or other suitable dimensions compatible with a guard lumen 4020 sufficient to accommodate the distal portion of delivery catheter 3344 and penetrating element 3350. As shown in FIG. 4D, the distal portion 4011 of pull wire 4010 does not include the PTFE coating depicted on the body portion of pull wire 4010; the uncoated stainless steel distal portion 4011 of pull wire allows for a weld or other connection point 4011a to radiopaque marker.

Figure 4E:
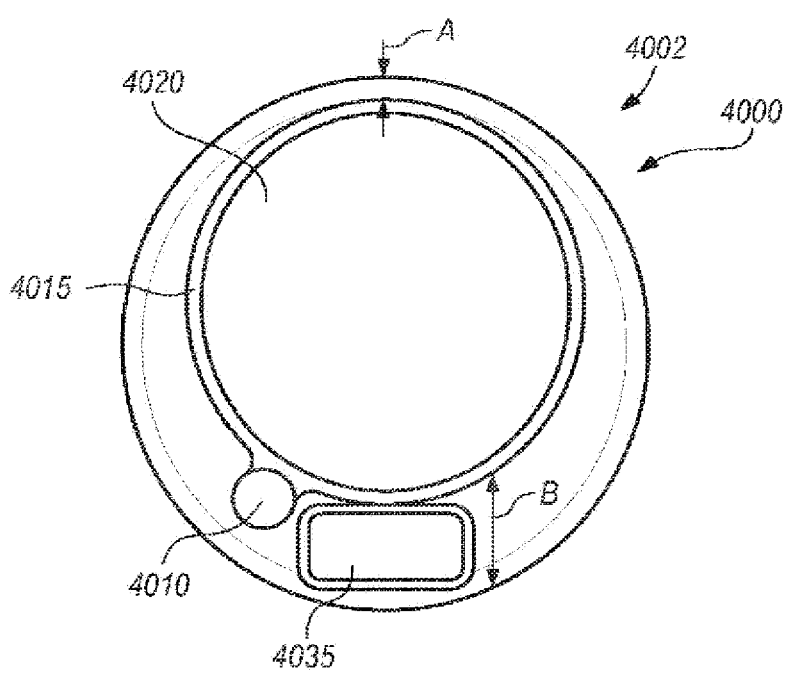
Figure 4F:
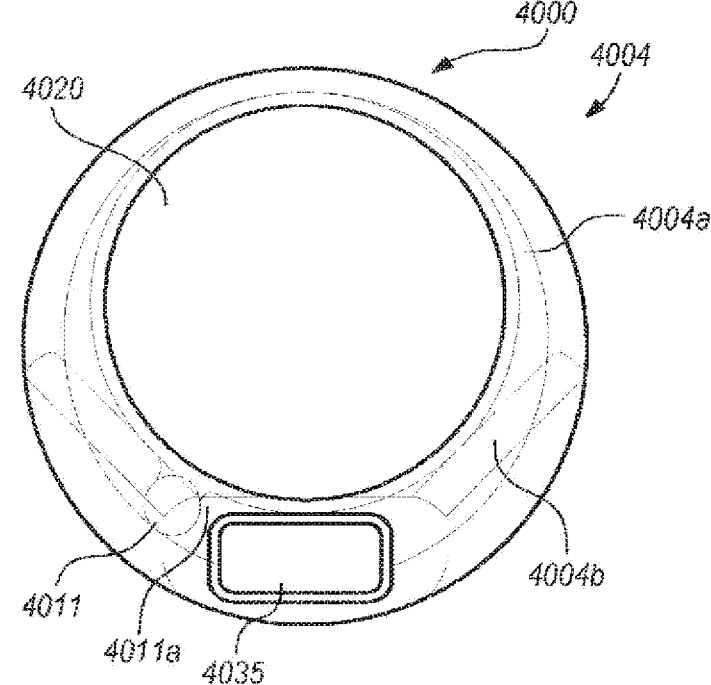

FIGS. 4E and 4F show cross section views of the proximal portion 4002 and distal portion 4004, respectively, of the guard member 4000. As depicted in FIG. 4E, marker 4015 and pull wire 4010 are embedded or encapsulated within the wall of guard 4000. Guard 4000 can comprise polymeric materials such as polyether block amide (Pebax®) available from Arkema Group), HTPE, PTFE, urethanes or the like. Pebax embodiments of guard 4000 can range from 27 D to 70 D hardness (e.g., Pebax 63D). The wall thickness of guard 4000 can vary depending on top-to-bottom orientation of the guard. The top portion of guard 4000 (represented by line A in FIG. 4E) can range from about 0.002" to 0.006" (0.0508 mm to 0.1524 mm) or larger. The bottom portion of guard 4000 (represented by line B in FIG. 4E) can range from about 0.008" to 0.014" (0.2032 mm to 0.3556 mm) or larger.

As previously disclosed and during a shunt implantation or other procedure for accessing the intracranial subarachnoid space, a clinician can deploy an anchor 700 distal to a target penetration site along IPS wall 114. Thereafter, the clinician advances a delivery assembly 300 comprising delivery catheter 3304 and penetrating element guard 4000 via elongate member 780 to the target penetration site. The radiopaque marking 3354 on the distal portion 3344 of the delivery catheter 3304 and radiopaque marking 4015 within guard 4000 provide reference points for the clinician to visualize the location of the delivery assembly and penetrating element 3350 at the target penetration site. When the clinician is prepared to penetrate IPS wall 114, the clinician can pull the proximal end of pull wire 4010 proximally, which retracts guard 4000 proximally over the distal portion 3344 of delivery catheter (indicated by the direction of the left-hand arrow d2 shown in FIG. 19A) and exposes penetrating element 3350 from the delivery assembly 300. Observing the transition of marker 4015 in guard 4000 proximally towards and/or until it abuts marker 3354 on the distal portion 3344 of the delivery catheter (e.g., in the direction of arrow d2 shown in FIG. 4A) confirms that guard 4000 actuated properly and penetrating element 3350 is exposed from the delivery assembly in the patient's vasculature. Conversely, after shunt implantation, the clinician can advance pull wire 4010 distally to re-cover penetrating element 3350 and confirm that the guard 4000 is in a delivery or withdrawal configuration (e.g., penetrating element not exposed in IPS 102 or jugular vein 106 lumens).

Figures 4G, 4H, 4I, 5:
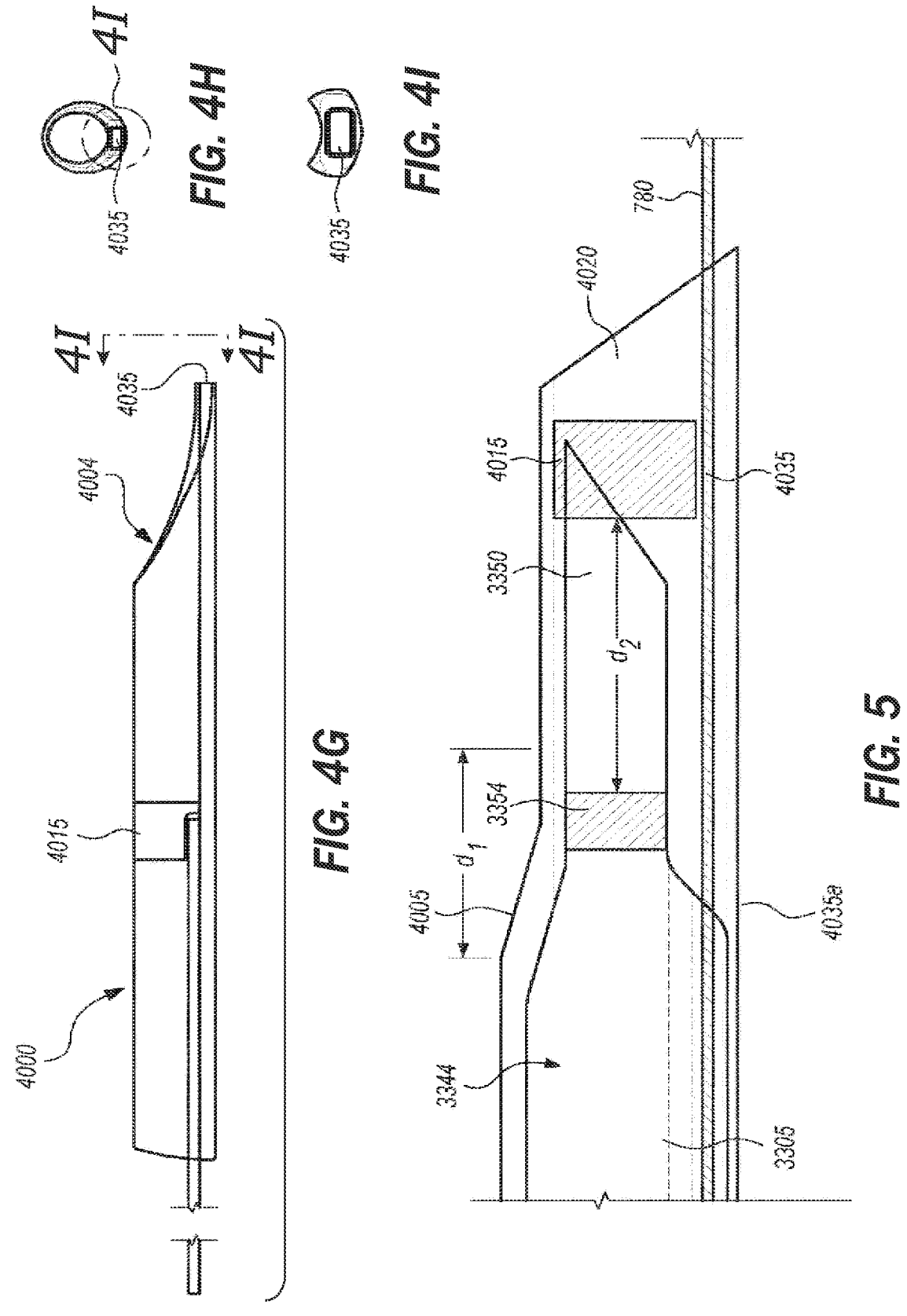
FIG. 5 is a sidecross-sectional view of a penetrating element guard, constructed according to an alternative embodiment of the disclosed inventions.

FIG. 5 depicts an alternate embodiment of penetrating element guard 4000. For ease in illustration, like features of the penetrating element guard 4000 and delivery catheter 3304 shown in FIG. 5 have been given the same reference numerals from FIGS. 4A-F. Guard 4000 comprises a guard 4000 having a full-length, "oversheath" configuration; that is, guard 4000 is a sheath that extends along the length of and over the delivery catheter 3304 disposed concentrically within guard lumen 4020. Guard 4000 can be retracted proximally (direction of left-hand arrow D2 in FIG. 5), e.g., by a clinician pulling on the proximal portion of guard 4000 to uncover and expose a protected penetrating element 3350. Optionally, guard 4000 can include a scored or weakened portion (e.g., indicated by dotted line d1 in FIG. 5) that splits or tears (e.g., along the longitudinal axis of the guard) to facilitate guard retraction.

Guard 4000 includes a second lumen 4035 that accommodates elongate guide member 780. Lumen 4035 can extend from the distal portion or end of guard 4000 and include an exit port 4035a located in the distal portion of guard 4000, as shown in FIG. 5. As compared to the guard configuration described in connection with FIGS. 4A-F, the guard configuration shown in FIG. 5 simplifies the design of the delivery assembly 300 by eliminating pull wire 4010 and a corresponding pull wire lumen 3325 in the delivery catheter 3304.

FIGS. 6A-M depict an alternate embodiment of delivery catheter 3304. FIGS. 6C and D show longitudinal side and cross section views, respectively, of delivery catheter 3304. FIGS. 6A and B show cross section views of delivery catheter 3304 at reference lines in FIG. 6C, respectively, looking from the distal portion 3344 of the catheter towards the proximal portion. FIG. 6I shows another longitudinal side view of the delivery catheter of FIGS. 6A-M. FIGS. 6F-M depict cross section views of delivery catheter 3304 at various points along the longitudinal axis corresponding to the reference line designations in FIG. 6I.

With respect to FIGS. 6C, D, and I, the depicted delivery catheter 3304 includes a beveled-needle penetrating element 3350 on the distal portion 3344 of the delivery catheter. The penetrating element 3350 can be fixed to the delivery catheter and, as depicted, is welded to reinforcing member 1345 (further described below). Delivery catheter includes three distinct radiopaque marker bands: a distal most marker 3354 located about the proximal portion of penetrating element 3350, an intermediate marker 3354*a*, and proximal most marker 3345*b*. A first lumen 3315 in the delivery catheter accommodates elongate guide member 780 and lumen 3315 can include a polymeric liner 3306 material such as PTFE (FIG. 6B) to increase the lubricity of the lumen and facilitate smooth motion of the delivery catheter 3304 over guide member 780.

As depicted, first lumen 3315 has a rapid-exchange configuration and does not span the entire longitudinal axis of deliver catheter 3304, although such a configuration is possible in other embodiments. Marker bands 3354*a* and 3354*b* reinforce the distal 3315*a* and proximal 3315*b* openings of lumen 3315, as shown in FIGS. 6A and 6K-L. FIG. 6D includes longitudinal dimensions along the length of delivery catheter 3304, measured from the proximal portion of penetrating element 3350 to the distal opening 3315*a* of first lumen 3315 (0.16"/0.4064 cm), to the distal edge of marker band 3354*a* (0.17"/0.4318 cm), to the distal edge of marker band 3354*b* (7.95"/20.193 cm), to the proximal opening 3315*b* of first lumen 3315 (8"/20.32 cm), and to the proximal portion of delivery catheter 3304 (39.37"/100 cm). Further, delivery catheter 3304 includes a second lumen 3305 to accommodate a shunt and shunt pusher delivery assembly as disclosed herein or other catheters and/or endovascular devices. Second lumen 3305 includes a polymeric liner material 3306 as indicated in FIGS. 6E, 6E-1, 6E-2 to FIG. 6M, such as PTFE.

The outer diameter of delivery catheter 3304 of FIGS. 6A-M varies along the longitudinal axis. The cross section views of FIGS. 6F-M, working from the distal most cross-section to the proximal most cross-section along the axis of delivery catheter 3304, correspond to the reference lines shown in FIG. 6I as follows: FIG. 6J at reference line E-E in FIG. 6I; FIG. 6F at reference line F-F in FIG. 6I; FIG. 6K at reference line G-G in FIG. 6I; FIG. 6G at reference line H-H in FIG. 6I; FIG. 6L at reference line I-I in FIG. 6I; FIG. 6H at reference line J-J in FIG. 6I; and FIG. 6M at reference line K-K in FIG. 6I. Each of FIGS. 6A-B and F-M specify the maximum outer diameter along the longitudinal axis of the delivery catheter 3304 at the location of the particular cross section depicted, which varies depending on the longitudinal location of the cross section along the axis of the catheter (e.g., ranging from 0.036" to 0.046"/0.09144 cm to 0.11684 cm). FIGS. 6K, 6F, and 6J depict a gradually tapering outer diameter in the distal portion of the delivery catheter 3304, moving in the distal direction along the axis of the catheter (i.e., from 0.046" to 0.036"/0.11684 to 0.09144 cm), which facilitates access to tortuous anatomy and narrowings in the vasculature (e.g., junction 118 of jugular vein 106 and IPS 102).

While FIGS. 6A-M and the foregoing description reference a two-lumen delivery catheter 3304, additional embodiments of the delivery catheter can include a third lumen (e.g., lumen 3325 of 19A, to accommodate, for example, a pull wire of a penetrating element guard 4000, as further described below) and fourth lumen (e.g., lumen of to accommodate, for example, a second pull wire of a penetrating element guard 4000, as further described below and shown in FIGS. 14D-E).

Figure 7A:
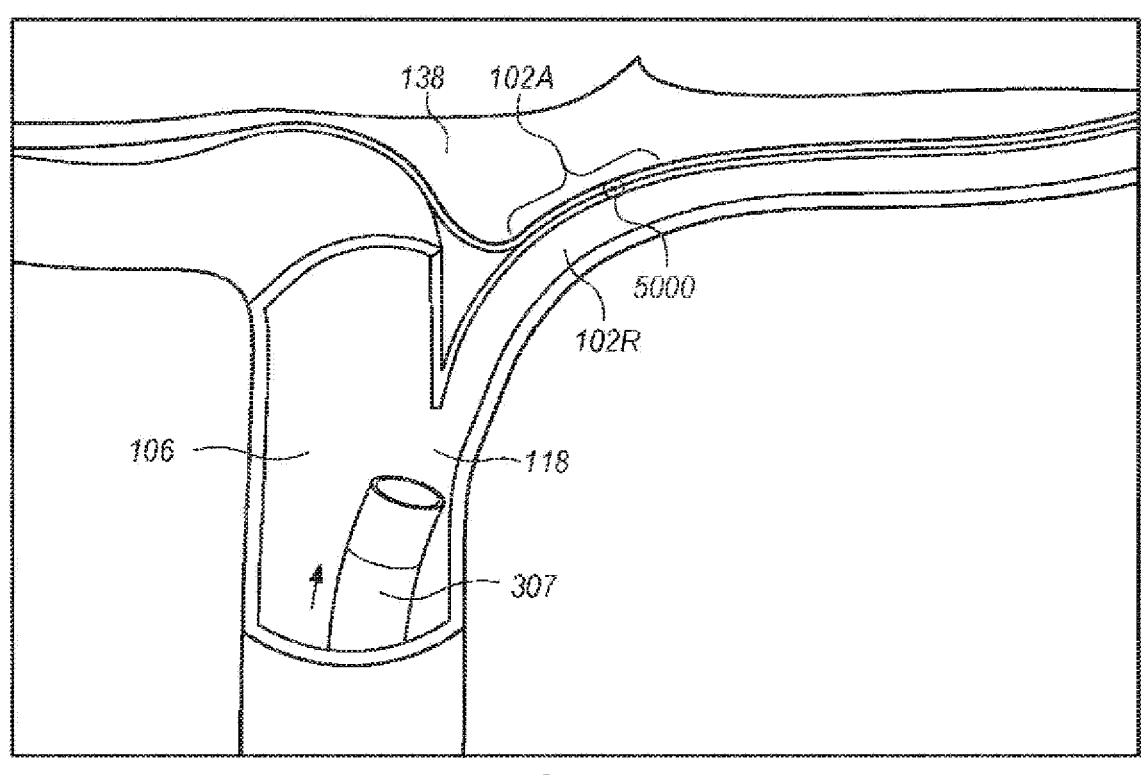
FIGS. 7A-O are perspective and cross-sectional views of exemplary methods for anchor delivery and shunt implantation procedures, according to embodiments of the disclosed inventions.

FIGS. 7A-O illustrate an exemplary shunt implant procedure in a patient suffering from elevated intracranial pressure. Any of the foregoing shunt and delivery system embodiments described herein can be used in the following exemplary procedure. The clinician can obtain CT and/or MRI imaging (e.g., coronal, T2, thin cut MRI images with gadolinium contrast) studies of the patient's intracranial anatomy to ascertain the sizing and relative proximity between the patient's right IPS 102R and left IPS 102L, CP angle cistern 138, arterial structures (e.g., basilar artery), and surrounding bony anatomy; such imaging can also be used to assess the volume of unobstructed CSF space of CP angle cistern 138 surrounding the left and right IPS channels relative to a target penetration site 5000 in an IPS 102 where an anastomosis will be made during the shunt implant procedure. The clinician can use this pre-procedure imaging to select one or more preferred shunt deployment locations along the first curved portion 102A and/or second curved portion 102B in the patient's right IPS 102R and/or left IPS 102L. To further illustrate the following exemplary procedure, the clinician selects the patient's right IPS 102R and a target penetration site 5000 along the first curve 102A of the IPS based on the pre-procedure MRI imaging study, as shown in FIG. 7A.

The clinician gains access to the patient's venous vasculature through the patient's right femoral vein using an introducer kit (e.g., Micropuncture Introducer Set from Cook Medical of Bloomington, Indiana) and the Seldinger technique. The clinician then navigates a guide wire (e.g., 0.035" guide wire such as an 0.035" GLIDEWIRE from Terumo Interventional Systems of Somerset, New Jersey) and a guide catheter 307 (e.g., 6 Fr catheter such as 6Fr ENVOY Guiding Catheter from Codman Neuro of Raynham, Massachusetts) through the femoral vein access point, distally through the vena cava and into the right jugular vein. The clinician can position the distal end of the guide catheter 307 about the JV-IPS junction 118 as shown in FIG. 7A, and in certain patient anatomies, the distal end of the guide catheter can access the proximal portion of the IPS 102. Optionally, a shuttle sheath (e.g., 7Fr Flexor Shuttle Guiding Sheath from Cook Medical of Bloomington, Indiana) may be advanced through the patient's venous vasculature, prior to advancing the guide catheter 307; the guide catheter 307 can then be advanced through the shuttle sheath lumen to the jugular vein or JV-IPS junction 118. The shuttle sheath can provide additional support to the guide catheter, other catheter and guide wire components navigated to IPS 102 during the shunt procedure.

Figure 7B:
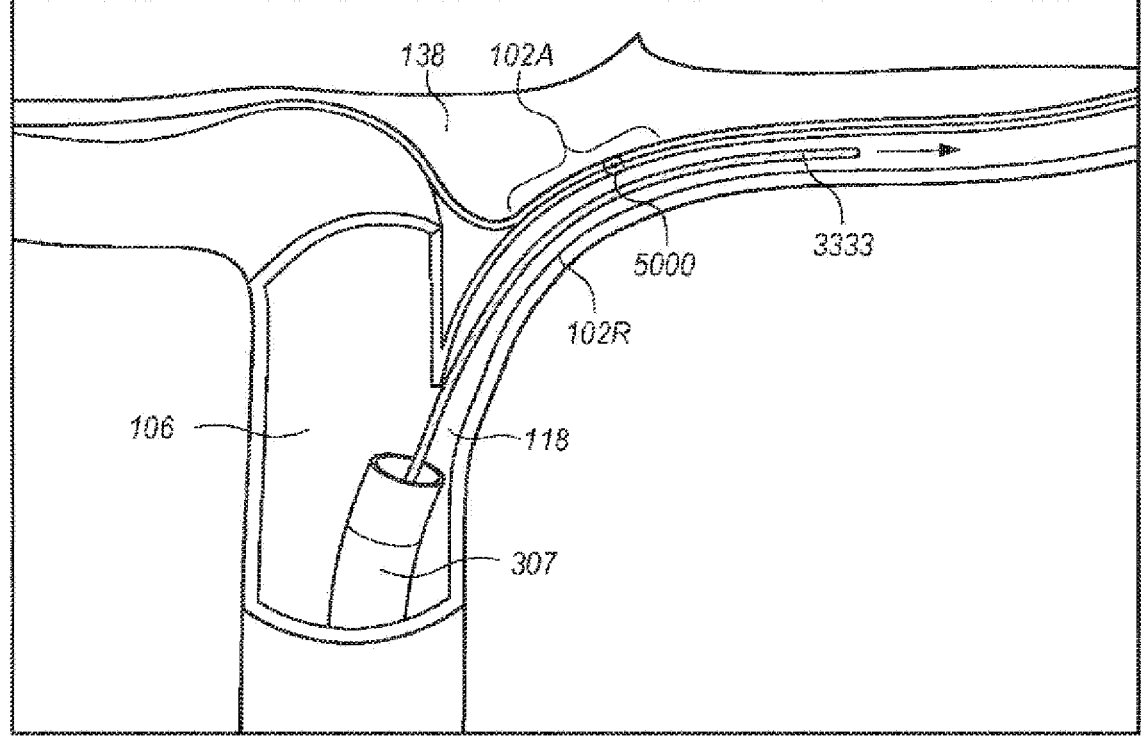
Figure 7C:
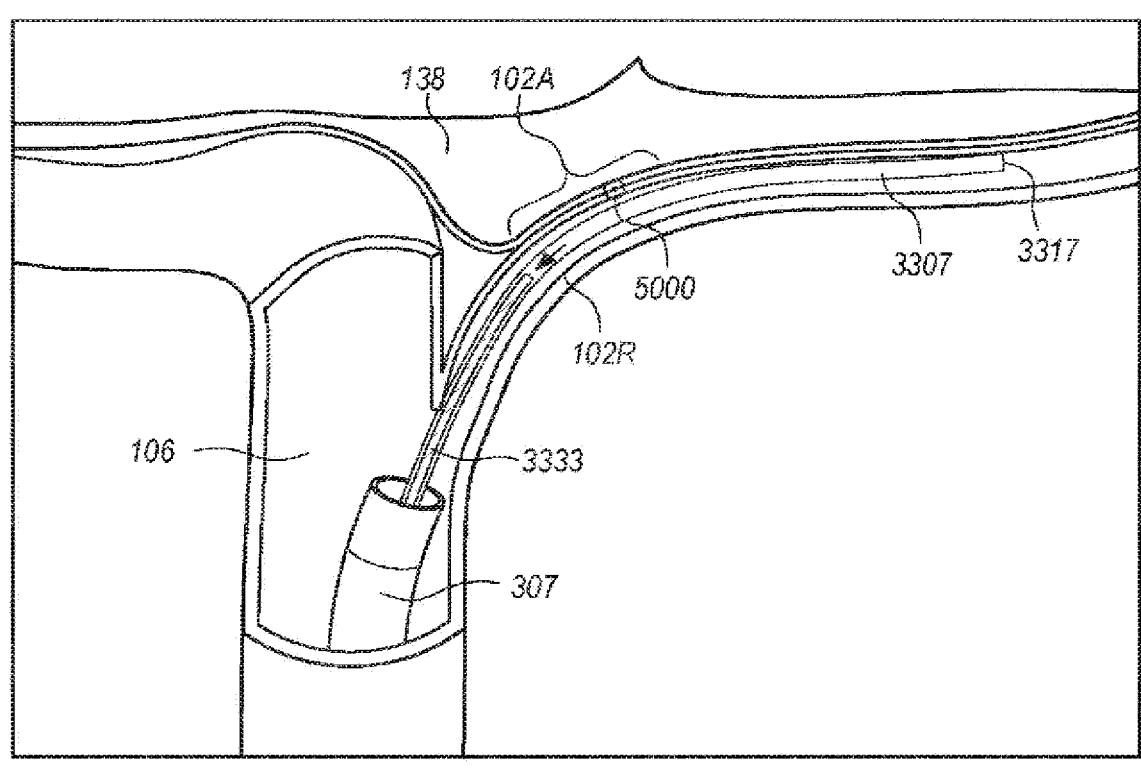
Figure 7D:
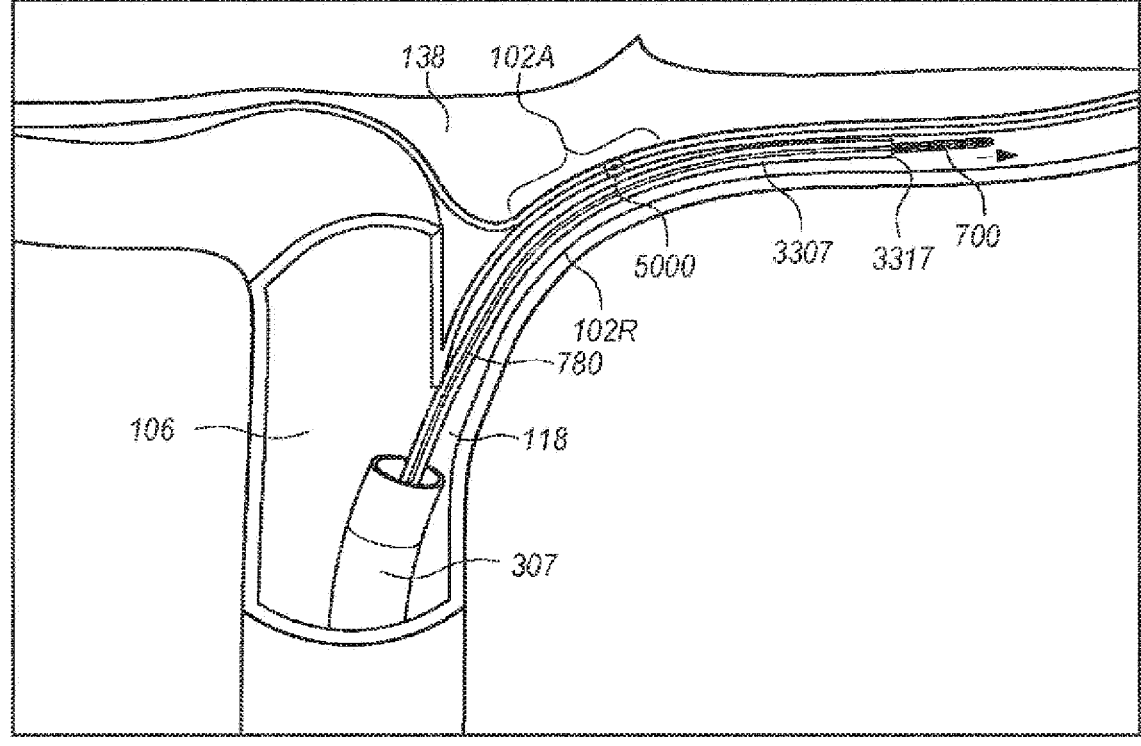

Then, the clinician accesses the right IPS 102R and/or cavernous sinus 104 with a micro catheter 3307 and micro wire 3333 (FIGS. 7B and 7C). The micro catheter is omitted from FIG. 7B for clarity of the micro wire 3333. The micro catheter 3307 described as being used in the medical procedures herein can include the micro catheter reinforcing members 1100, 1200, 1500, or 1600 described above and can include any of the various parameters or features discussed herein to achieve improved performance characteristics such as better maneuverability and reliability. The micro catheter 3307 advances through the guide catheter lumen, and the micro wire (e.g., an 0.010", 0.014", or 0.018" guide wire such as a Synchro2 Guidewire from Stryker Neurovascular of Fremont, California) can pass through the micro catheter lumen. The clinician advances the micro wire 3333 and micro catheter 3307 through the JV-IPS junction 118 into the right IPS 102R (e.g., the micro wire 3333 may be advanced distally and incrementally, followed by the micro catheter 3307 advancing distally and incrementally over the micro wire 3333, repeating the wire and catheter advancement steps in serial fashion; the micro wire may be advanced to its distal location first with the micro catheter following thereafter in two separate advancements; or the micro wire and micro catheter can be advanced distally, simultaneously through the JV-IPS junction 118 and into the right IPS 102R). The clinician can position the distal end of the micro catheter 3307 at a location distal to the target penetration site 5000 in IPS wall 114 along first curve 102A of the right IPS 102R as shown in FIG. 7C. As discussed herein, the catheter, the reinforcing member therein, can be formed to have structural features to improve maneuverability as the clinician positions the distal tip of the catheter. For example, improved column strength and better responsiveness to torque and rotational inputs can help make it easier for the clinician, for example, to access and maneuver within the IPS and other venous sinuses. The clinician withdraws the micro wire 3333 from the micro catheter 3307, leaving the distal opening 3317 of the micro catheter 3307 distal to the target penetration site 5000 in IPS wall 114 along first curve 102A of the right IPS 102R, as shown in FIG. 7C.

Figure 7E:
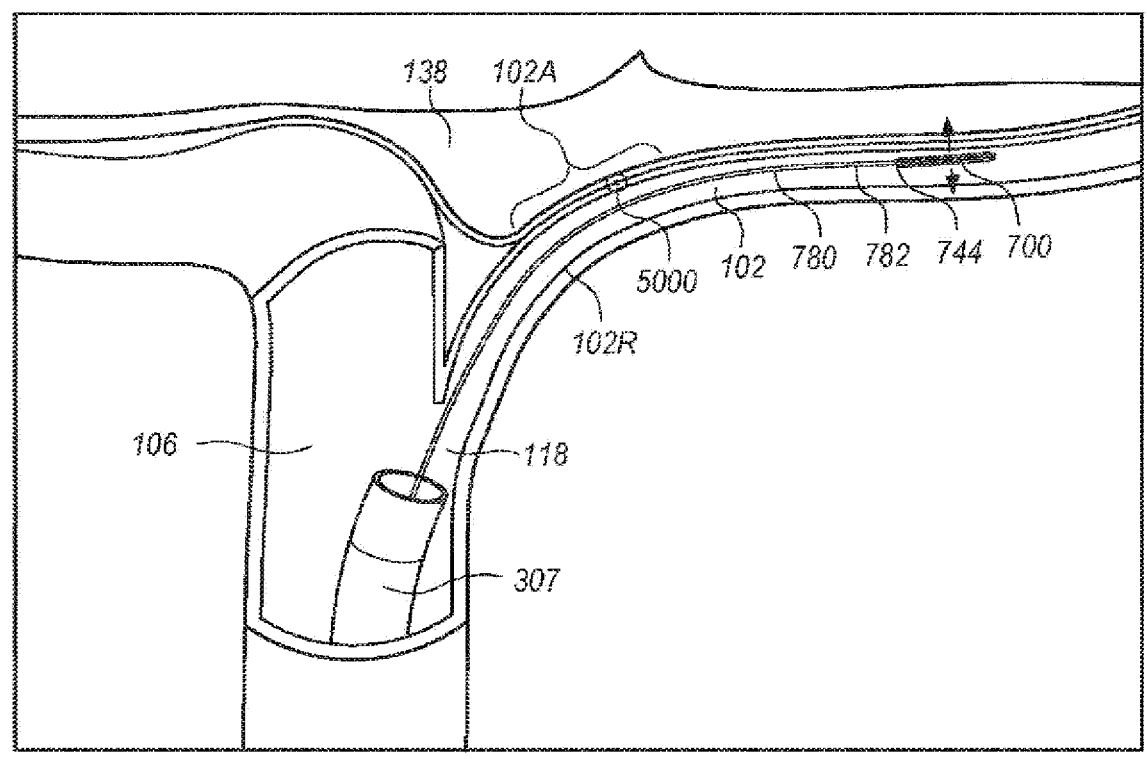

The clinician then deploys an anchor 700 and guide member 780 in the distal portion of the right IPS 102R in step 5020 of the procedure, which results in the anchor 700 secured in IPS 102R, distal to the target penetration site along IPS wall 114 of the first curved portion 102A of the right IPS 102R as shown in FIG. 7E.

The clinician then positions the distal portion of the micro catheter 3307 (i.e., with anchor 700 and guide member 780 packed inside) about the location for anchor deployment, and withdraws the micro catheter 3307 proximally while holding the anchor 700 in place using guide member 780 and/or advances anchor 700 via guide member 780 distally through the distal opening 3317 of the micro catheter 3307 while holding the micro catheter 3307 in place until the anchor 700 emerges from the catheter lumen and expands against the walls of the sinus lumen. As discussed above, the micro catheter 3307 can be formed to have improved tensile strength and force transmission due to the reinforcing members described herein. As such, the micro catheters described herein can make it easier and more precise for the clinician to move the guide member 780 and anchor 700 relative to the micro catheter 3307 without unintentionally disturbing (or limiting significant disturbance of) the position of the distal tip of the micro catheter 3307 because it is less likely to be stretched or be deflected under axial forces generated by moving the anchor 700 within the micro catheter.

At this point of the procedure, a distal portion of guide member 780 such as joint 744 coupling the guide member and anchor 700, can be disposed in the sinus lumen; the remainder of guide member 780 remains within the micro catheter lumen. If the clinician is satisfied with the anchor deployment location, he then withdraws the micro catheter from the patient, leaving behind the deployed anchor 700 with guide member 780 that extends proximally from the proximal portion of anchor 700 through the first curved portion 102A and junction 118 as shown in FIG. 7E, through the patient's venous vasculature and out of the patient via the femoral vein access point. Alternatively, he can recapture the deployed anchor 700 and guide member 780 into the micro catheter lumen and redeploy the anchor in the sinus lumen one or more times until he is satisfied with the anchor deployment location. Optionally, the clinician can use an elongated pusher (not shown) with micro catheter 3307 to facilitate anchor 700 recapture and redeployment in the sinus lumen.

Figure 7F:
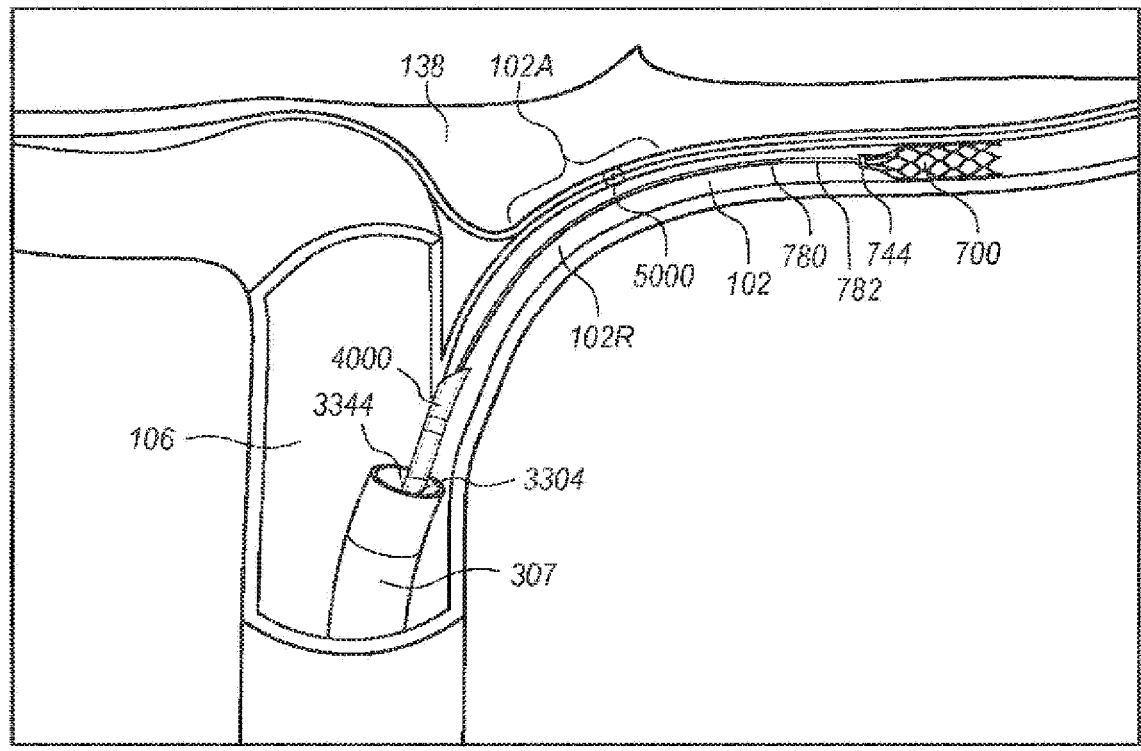
Figures 7G, 7H:
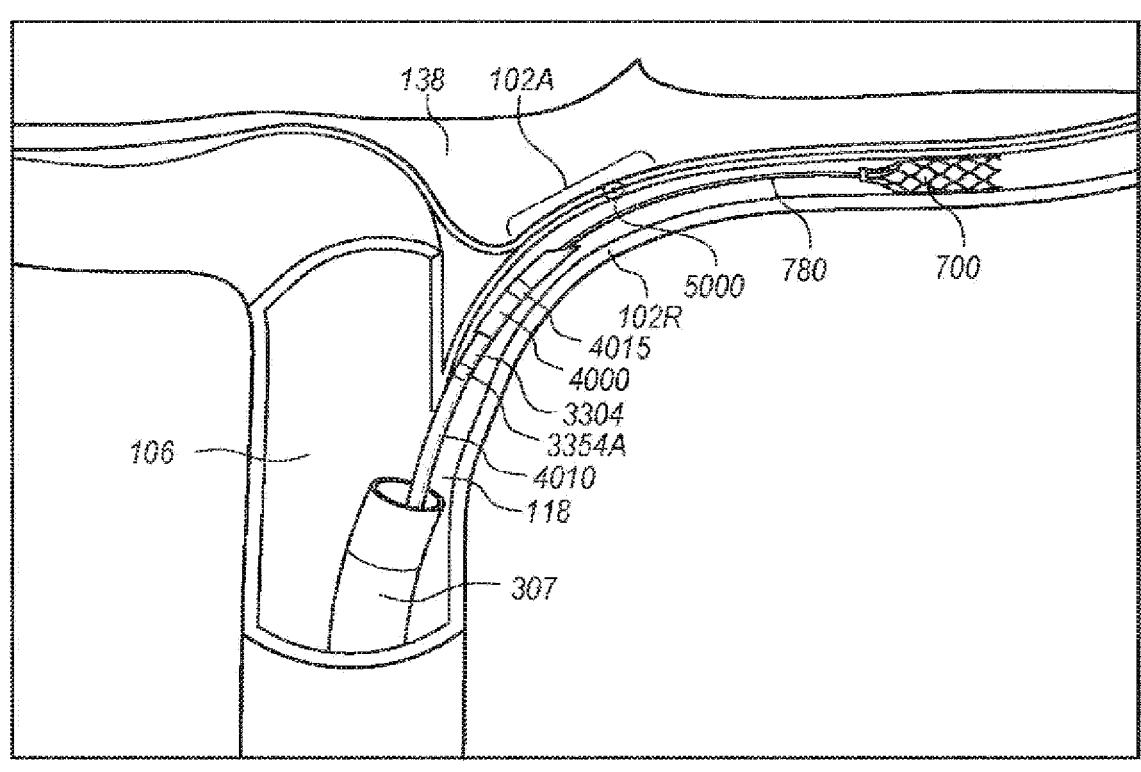

To continue the procedure, the clinician introduces delivery catheter 3304 into the patient's vasculature via the femoral vein access point and navigates the catheter 3304 distally through the JV-IPS junction 118 (as shown in FIG. 7F) to the target penetration site 5000 along IPS wall 114 of the first curved portion 102A of the right IPS 102R. The clinician can feed the proximal end of guide member 780 through the first lumen 3315 of delivery catheter 3304, via distal opening 3315a and proximal opening 3315b of the first lumen. The clinician then advances delivery catheter 3304 over guide member 780, through the femoral vein access point and tracks the delivery catheter 3304 distally, over the guide member 780 and through the patient's venous vasculature, until the distal portion 3344 of the delivery catheter 3304 is positioned about the target penetration site 5000 along IPS wall 114 of the first curved portion 102A of the right IPS 102R as shown in FIG. 7G. While tracking the delivery catheter 3304 distally, the clinician can hold the guide member 780 stationary or pull proximally on the proximal portion 784 of the guide member 780 to facilitate advancement of the delivery catheter 3304 through the patient's venous anatomy. In addition, the clinician can rotate the delivery catheter 3304 while tracking distally over the guide member 780 to overcome any resistance, e.g., resistance encountered while tracking the catheter through JV-IPS junction 118 and/or into right IPS 102R.

The clinician can confirm the orientation of the delivery catheter 3304 and the trajectory of penetrating element 3350 through IPS wall 114 into CP angle cistern 138 relative to the target penetration site 5000 using one or more of the previously disclosed imaging techniques. The clinician may use the distal 3354a and proximal 3354b markers located on the distal portion 3344 of the delivery catheter 3304 in this confirmation step. The markers will be visible under various imaging modalities used during the procedure (e.g., bi- or single-plane fluoroscopy). To the extent the clinician has created a 3D reconstruction of the patient's anatomy about the target penetration site 5000 (e.g., using 3D-rotational angiography or venography), the clinician can confirm the orientation and/or trajectory of the penetrating element 3350 by combining the fluoroscopy and 3D reconstruction using a 3D road mapping technique. Optionally, the clinician can use the 3D reconstruction data to create a window representing the target penetration site 5000; the 3D window and live fluoroscopy can be overlaid with respect to each other to provide further guidance for the clinician to penetrate IPS wall 114 at target penetration site 5000.

Then, the clinician retracts the penetrating element guard or guard member 4000 to expose penetrating element 3350 in the IPS 102 at the target penetration site along IPS wall 114 of the first curved portion 102A of the right IPS 102R as shown in FIG. 7H. The clinician retracts the guard member 4000 by pulling proximally on pull wire 4010 while holding the remainder of delivery catheter 3304 in place. While retracting guard 4000 and using the previously disclosed imaging techniques, the clinician will observe marker 4015 in guard 4000 transition proximally towards and/or until it abuts or overlaps with distal marker 3354a located on the distal portion 3344 of delivery catheter 3304. Again, the clinician can confirm the trajectory of penetrating element 3350 through the IPS wall 114 into CP angle cistern 138 using one or more of the previously disclosed imaging techniques before penetrating IPS wall 114. If the clinician is unsatisfied with the trajectory of the penetrating element 3350 or perceived penetration site 5000 on IPS wall 114, the clinician can adjust the location of the distal portion 3344 of delivery catheter 3304 until the clinician is satisfied that penetrating element 3350 will penetrate the IPS wall 114 at the target location along the first curved portion 102A of the right IPS 102R. When adjusting the location of the distal portion 3344 of delivery catheter 3304 the clinician can re-sheath penetrating element 3350 by advancing the penetrating element guard 4000 distally via pull wire 4010 and then unsheath penetrating element by retracting guard 4000 proximally before penetrating IPS wall 114; this re-sheathing step can prevent inadvertent penetration or injury to the IPS walls that could occur if the penetrating element 3350 were uncovered or unprotected while the clinician repositioned delivery catheter 3304 in the IPS 102.

Figure 7I:
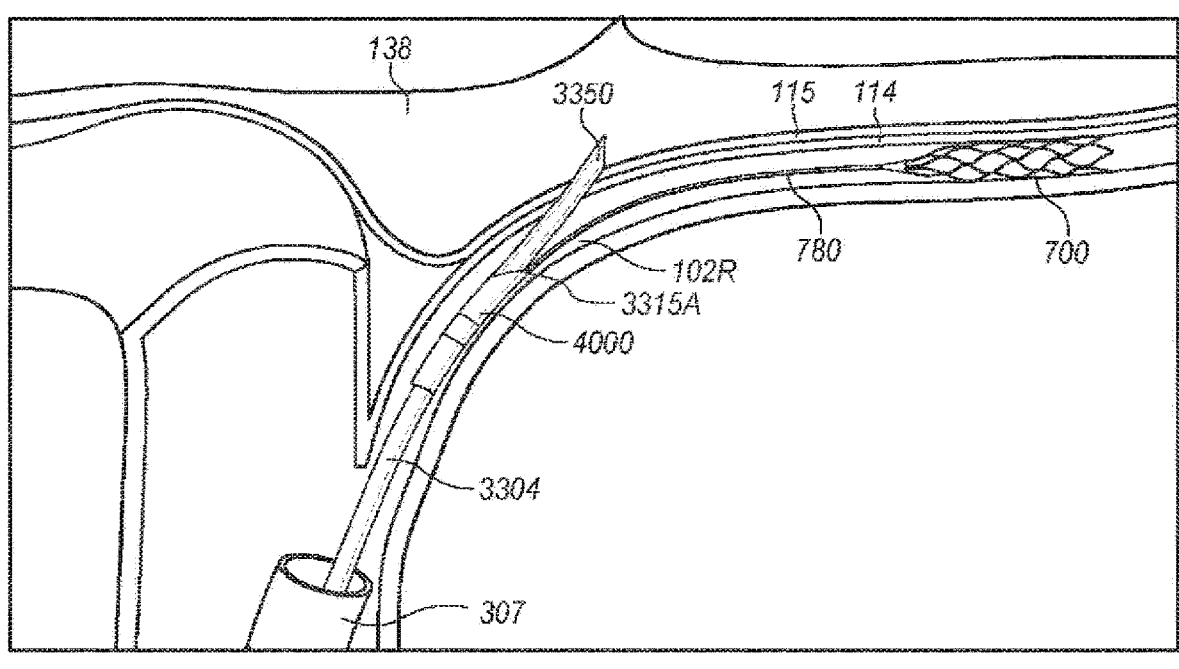

With the penetrating element 3350 oriented along a desired trajectory at the target penetration along IPS wall 114, the clinician advances delivery catheter 3304 distally so that penetrating element 3350 passes through the dura of IPS wall 114, arachnoid layer 115, and into the CSF-filled subarachnoid space of CP angle cistern 138 as shown in FIG. 7I. The clinician can pull proximally on the proximal portion of guide member 780 or hold the guide member 780 in place while advancing delivery catheter 3304 distally to cause the penetrating element 3350 to penetrate the IPS wall 114; these techniques allow the portion of delivery catheter 3304, distal of the lumen opening 3315a to track along the target trajectory and off-axis from the path of guide member 780 through the first curved portion 102A of the right IPS 102R. The clinician stops advancing delivery catheter 3304 distally when the clinician is satisfied that penetrating element 3350 and second lumen 3305 of delivery catheter 3304 have accessed CSF of the CP angle cistern 138; this can be confirmed via one or more of the previously disclosed imaging techniques, e.g., by 3D road mapping.

Figure 7J:
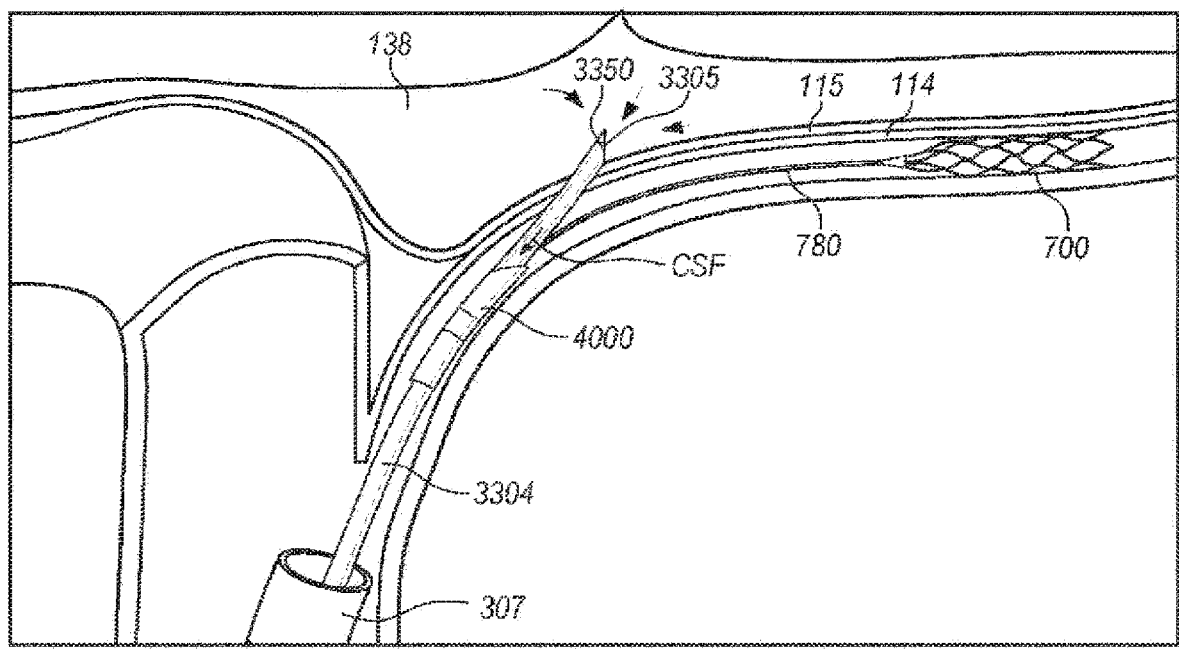

As an alternative method of confirming access to CP angle cistern 138, the clinician can aspirate CSF through the penetrating element 3350 and second lumen 3305 of delivery catheter 3304 to confirm that the penetrating element 3350 passed through IPS wall 114 and arachnoid layer 115 to access CSF within CP angle cistern 138 (e.g., aspirated CSF denoted by arrow-head lines in FIG. 7J). The clinician can use a syringe on the distal portion of handle (e.g., 10 cc syringe) to aspirate CSF proximally, through delivery catheter 3304. The presence of clear CSF in the syringe can confirm a successful penetration through the IPS into the CP angle cistern 138. If the clinician observes blood in the syringe, this can indicate that the penetrating element 3350 did not completely pass through IPS wall 114 or remained entirely within right IPS 102R. If the clinician did not penetrate IPS wall 114, the clinician can re-attempt to penetrate IPS wall 114 at the target site, attempt to penetrate IPS wall 114 at another target penetration site along the first curved portion 102A of right IPS 102R, attempt to penetrate IPS wall 114 along the second curved portion 102B of right IPS 102R as will be further described below, or abort the procedure.

Figure 7K:
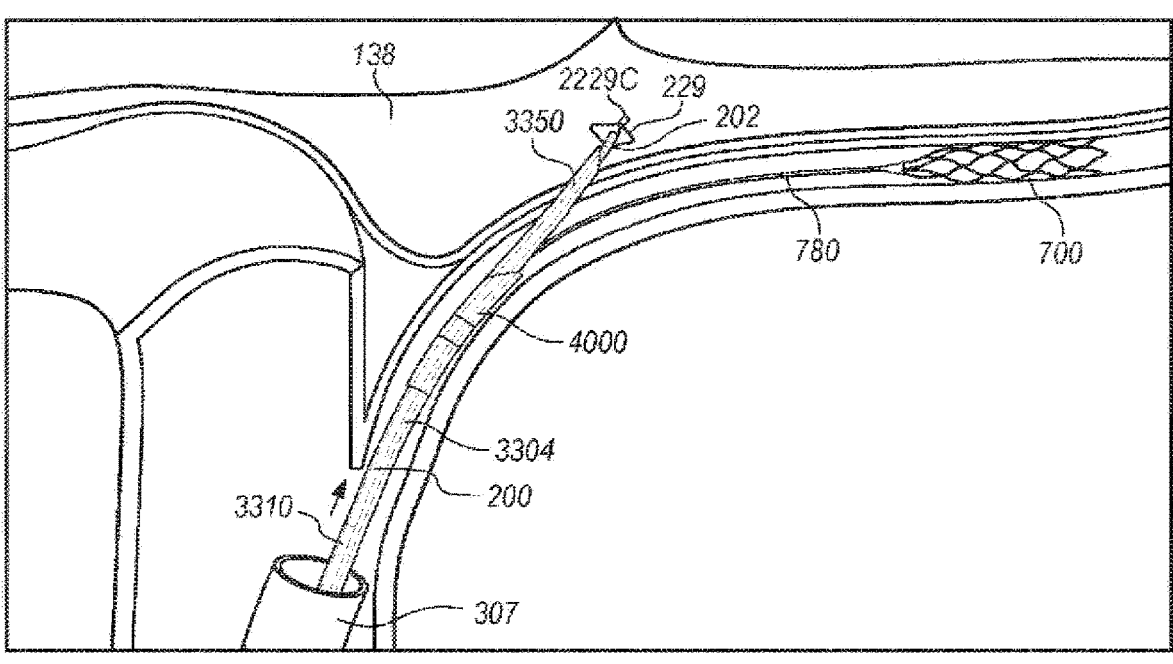

After confirming that the penetrating element 3350 passed through IPS wall 114 and arachnoid layer 115 to access CSF within CP angle cistern 138, the clinician advances pusher member 3310 distally to advance shunt 200 distally from the lumen 3305 of delivery catheter 3304 until the distal anchoring mechanism 229 of the shunt deploys in CP angle cistern 138 in step 5050 of the procedure as shown in FIG. 7K. The clinician can confirm that the distal anchoring mechanism 229 of the shunt deployed in the cistern by observing a radiopaque marking(s) on a distal portion of the shunt as it emerges from the catheter into the subarachnoid space, using one the previously disclosed imaging techniques (e.g., by using live fluoroscopy to observe the RO makings in the distal portion of the shunt transition from a delivery configuration to a deployed configuration as described in connection with FIG. 7C). By pulling shunt pusher 3310 proximally (and, optionally, simultaneously pulling delivery catheter 3304 proximally), the clinician fully expands the distal anchoring mechanism 229 against arachnoid layer 115 in CP angle cistern 138.

Figure 7L:
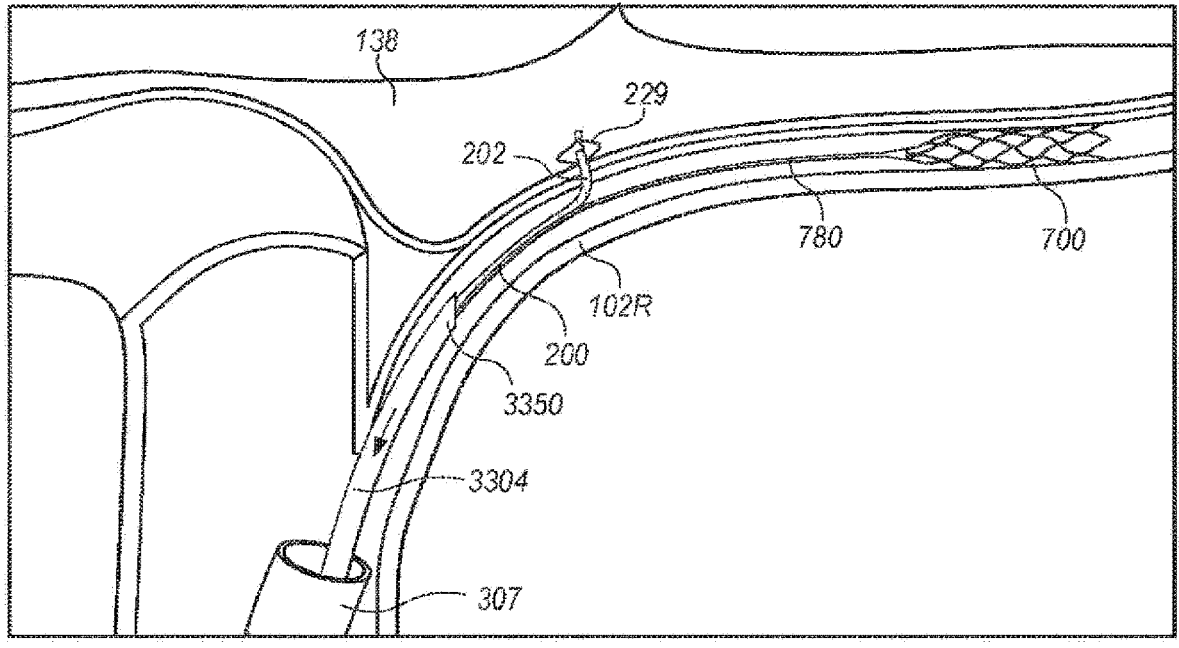

The clinician continues deploying shunt 200 across the penetration tract in IPS wall 114 and in the right IPS 102R in step 5055 of the procedure as shown in FIG. 7L. By holding shunt pusher member 3310 in place while withdrawing delivery catheter 3304 proximally, shunt 200 emerges from the delivery catheter lumen 3305 and deploys in the lumen of IPS 102R. At this point in the procedure, the proximal portion of shunt 200 and, if included on the particular embodiment of shunt 200 being deployed, proximal anchoring mechanism 227 on the shunt remain inside lumen 3305 of delivery catheter 3304; the remainder of the shunt is deployed in the CP angle cistern and right IPS 102R.

Figure 7M:
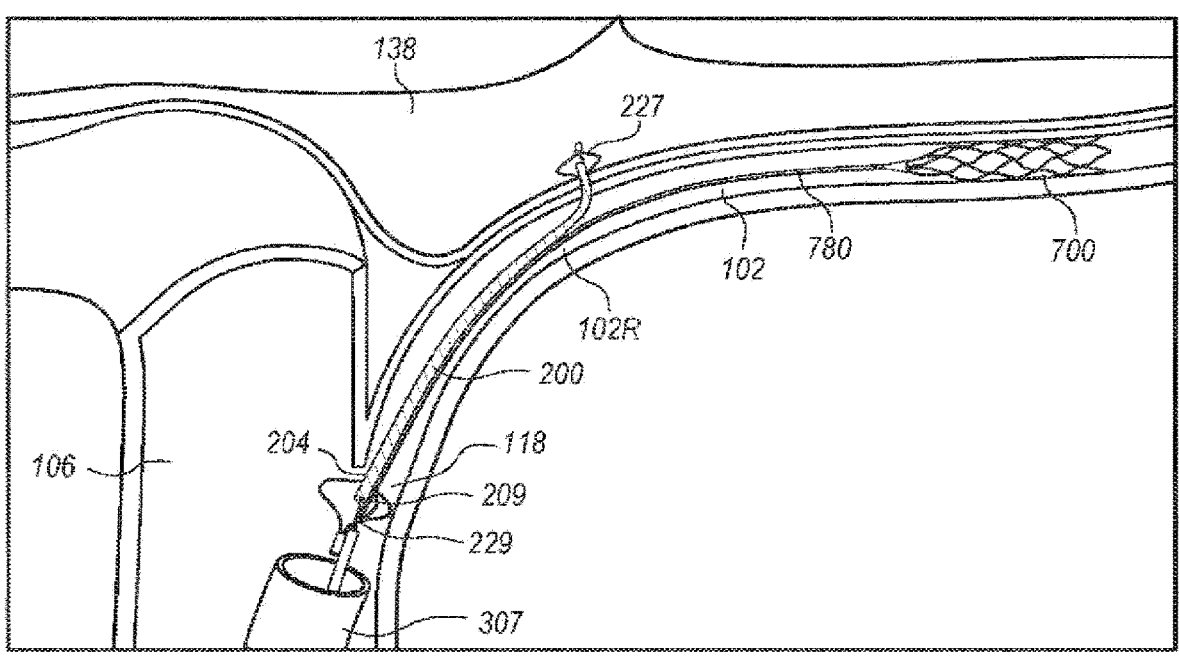

The clinician finishes deploying shunt 200 in step 5060 of the procedure by deploying proximal anchoring mechanism 227 of shunt 200 about the JV-IPS junction 118 or in jugular vein 106 as shown in FIG. 7M. Again, by holding shunt pusher member 3310 in place while withdrawing delivery catheter 3304 proximally, shunt 200 emerges from delivery catheter lumen 3305. As the proximal anchoring mechanism 227 and interlocking elements 229 on the distal portion of the shunt pusher member 3310 emerge from within the delivery catheter lumen 3305, the shunt pusher member and shunt separate or disconnect, thereby releasing shunt 200 from pusher member 3310. The clinician, optionally, can pause the shunt deployment step before the shunt completely releases from the interlock (or the self-expanding distal end portion of the shunt delivery shuttle disclosed herein) of pusher member 3310 by holding delivery catheter 3304 in place (e.g., by not withdrawing delivery catheter 3304 proximally) to confirm that he is satisfied with the shunt deployment location in the patient before completely releasing shunt 200 from delivery catheter 3304. In embodiments of shunt 200 that do not include a proximal anchoring mechanism 227, step 5060 is completed in substantially the same manner, with shunt 200 releasing from the shunt delivery shuttle 4316 and proximal portion of shunt deployed in the JV.

In the next step 5065 of the procedure, the clinician removes delivery catheter 3304 from the patient by withdrawing it proximally through the venous vasculature and out of the patient at the femoral vein access point. Optionally, the clinician holds guide member 780 in place while withdrawing delivery catheter 3304 proximally to ensure that anchor 700 does not migrate proximally through IPS 102R and interfere with deployed shunt 200.

Figure 7N:
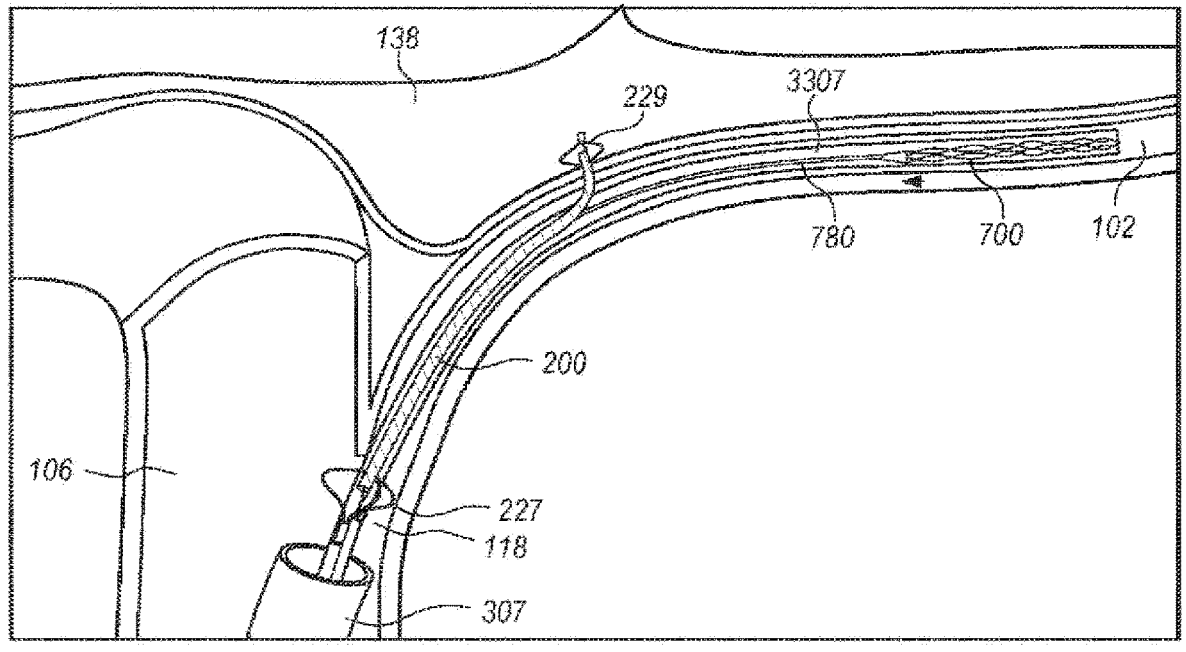

The clinician recaptures anchor 700 into the micro catheter (e.g., micro catheter 3307, which is omitted for clarity) and removes the anchor from the patient via the femoral vein access point in step 5070 of the procedure. By feeding the proximal portion of guide member 780 through the micro catheter lumen, the clinician can track the micro catheter distally over the guide member, around proximal anchoring mechanism 227 (if present) of the shunt deployed in the jugular vein 106 or JV-IPS junction 118, until the distal end of the micro catheter reaches the joint 744 between the guide member and anchor. He can then further advance the micro catheter distally and/or hold stationary or pull guide member 780 proximally to transition the anchor from its deployed or expanded configuration in the sinus lumen to its compressed configuration within the micro catheter lumen as shown in FIG. 7N. As discussed above, in some embodiments, the structural features detailed herein can improve structural characteristics of the reinforcing member of the micro catheter, for example, improved column strength and reduced likelihood of buckling. As a result, the micro catheter can, in some cases, more readily handle the user pulling the anchor 700 into the micro catheter without deforming or failing. With the anchor compressed in the micro catheter lumen, the clinician withdraws the micro catheter and anchor from the patient proximally, through the venous vasculature and out of the femoral vein access point. Thereafter, he withdraws the guide catheter from the patient.

The deployed shunt 200 (shown in FIG. 7O) and valve 2209 provide a one-way flow conduit to drain excess CSF from the patient's subarachnoid space into the jugular vein, thereby relieving the patient's elevated intracranial pressure. The arrows in FIG. 7O depict the direction of CSF flow from the CP angle cistern 138 into the shunt lumen 207, through valve 2209, and into jugular vein 106.

If in steps 5040 or 5045 of the procedure the clinician is unsuccessful at penetrating IPS wall 114 at the target penetration site along the first curved portion 102A, he can continue the procedure by attempting to penetrate IPS wall 114 along the second curved portion 102B of right IPS 102R (e.g., as shown in FIG. 2C). For example, in certain patient anatomies, an overhang of the petrous bone can prevent penetrating element 3350 from passing through IPS wall 114 into CP angle cistern 138. The presence of this bony overhang can be confirmed during the shunt implant procedure by using one or more of the previously disclosed imaging modalities. The clinician can then continue the procedure by re-sheathing penetrating element 3350 with penetrating element guard 4000, and advancing delivery catheter 3304 distally over guide member 780 until the distal portion of delivery catheter 3304 is positioned at a target penetration site along the second curved portion 102B of right IPS 102R. Optionally, the clinician can rotate delivery catheter 3304 from about 45 to 180 degrees while tracking distally from the first curved portion 102A toward the second curved portion 102B in IPS 102R; by rotating the delivery catheter, the clinician can orient penetrating element 3350 such that further distal advancement of delivery catheter 3304 will advance penetrating element 3350 through IPS wall 114 at a target penetration along the second curved portion 102B of right IPS 102R. The clinician can continue the procedure and deploy shunt 200 through IPS wall 114 along the second curved portion 102B of right IPS 102R as previously described in steps 5030-5070 of the procedure.

The shunt 200 capitalizes on a favorable pressure gradient between the subarachnoid space 116 (e.g., CP angle cistern 138) and venous system (e.g., IPS 102, jugular vein 106, and/or a jugular bulb 108) to drive CSF through the shunt 200 (i.e., inner lumen). In patients without hydrocephalus, the normal differential pressure between the intracranial pressure of the subarachnoid space 116 and blood pressure of the venous system is about 5 to 12 cm $H_2O$; this differential pressure between the subarachnoid space and venous system can be significantly higher in hydrocephalic patients. Once deployed and implanted, the shunt 200 facilitates one-way flow of CSF from the subarachnoid space 116 into the jugular the bulb 108 and/or jugular vein 106 where CSF is carried away by venous circulation, similar to the way that normally functioning arachnoid granulations drain CSF into the venous system. The shunt 200 prevents backflow of venous blood into subarachnoid space 116 via one or more one-way valves or any other flow regulating mechanisms. The shunt 200 allows for a more physiologic drainage of CSF by directing CSF into the cerebral venous system, a process that occurs naturally in people without hydrocephalus. In this manner, the pressure created by the excess CSF in the subarachnoid space 116 is relieved, and patient symptoms due to hydrocephalus can thereby be ameliorated or even eliminated. The shunt 200 of FIGS. 7M, and FIG. 7O includes a valve 209, 2209 as the flow regulating mechanism configured to regulate fluid flow through the shunt 200 into the venous system.

In embodiments of the inventions, a target flow rate of CSF (e.g., in a range of about 5 ml per hour to about 15 ml per hour) through the shunt 200 at a normal differential pressure is defined as being in a range between about 5 cm $H_2O$ to about 12 cm $H_2O$ between the subarachnoid space 116 and venous system (e.g., jugular vein 106 and/or a jugular bulb 108).

In some embodiments, a target flow rate of CSF through the shunt 200 and/or valve 209, 2209 is approximately 10 ml per hour at a range of differential pressure between the subarachnoid space 116 and venous system ("ΔP") between 3 to 5 mmHg. A maximum flow rate of CSF through the shunt 200 and/or valve 209, 2209 can exceed 20 ml per hour and typically occurs immediately after shunt implantation in a patient with elevated ICP (e.g., ICP greater than 20 cm $H_2O$). The valve 2209, as the flow regulating mechanism of the shunt 200, comprises a normal operating range (CSF flow direction) of 0.5 to 8 mmHg ΔP, having a valve opening pressure (CSF flow direction) of approximately 0.5 mmHg ΔP, and a reverse opening pressure (backflow prevention) of at least −115 mmHg ΔP. Additionally, the valve 209 may comprise an allowable CSF leakage (flow direction) of less or equal to 0.5 ml per hour, and/or an allowable blood backflow (reverse direction) of less or equal to 0.25 ml per hour.

A positive pressure gradient between the intracranial pressure (ICP) of the subarachnoid space and the blood pressure of the venous system may contribute to the natural absorption of CSF through arachnoid granulations. ICP greater than 20 cm H20 is considered pathological of hydrocephalus, although ICP in some forms of the disease can be lower than 20 cm H20. Venous blood pressure in the intracranial sinuses and jugular bulb and vein can range from about 4 cm H20 to about 11 cm H20 in non-hydrocephalic patients, and can be slightly elevated in diseased patients. While posture changes in patients, e.g., from supine to upright, affect ICP and venous pressures, the positive pressure gradient between ICP and venous pressure remains relatively constant. Momentary increases in venous pressure greater than ICP, however, can temporarily disturb this gradient, for example, during episodes of coughing, straining, or valsalva. The shunt 200 and/or the valve 209 2209 are configured to handle expected acute and chronic differential pressures between the subarachnoid space 116 and venous system ("ΔP") when implanted in a patient. A maximum, acute negative ΔP occurs, for example, between a maximum venous pressure (VP) and a minimum intracranial pressure (ICP), such as, if the patient coughs while moving from a supine to upright position. Embodiments of the valve 209 are configured to seal, shut and/or close under the negative ΔP conditions (i.e., when venous pressure exceeds intracranial pressure), preventing venous blood from flowing back through the shunt 200 into the subarachnoid space 116. A maximum, acute positive ΔP occurs, for example, between a maximum ICP and a minimum VP, such as the acute positive ΔP caused by coughing when the patient transitions from an upright to supine position. Additionally, the shunt 200 and/or the valve 209, 2209 are configured to handle chronic elevated, positive ΔP conditions (e.g., approximately two or more minutes of elevated positive ΔP, such as between maximum hydrocephalus ICP and normal VP [e.g., hydrocephalus with low expected VP]); and to handle chronic, elevated negative ΔP conditions (e.g., approximately two or more minutes of negative ΔP, such as between minimum ICP and maximum VP [e.g., supine→upright posture change with minimal VP adjustment]).

FIGS. 8A-E illustrate another embodiment of a shunt 2200. Shunt 2200 includes a distal anchoring mechanism 2229 (i.e., malelcot), as well as a retaining element 2230 comprising a radiopaque material, which element will be further described below. Distal anchoring mechanism 2229 includes arms or tines 2229a comprising a hinge, living joint, or the like 2229b, as previously described herein. The shunt 2200 further comprises a shunt body 2203, CSF lumen 2207, and a one-way valve 2209 located in the proximal portion 2204 of the shunt.

Figure 8A:
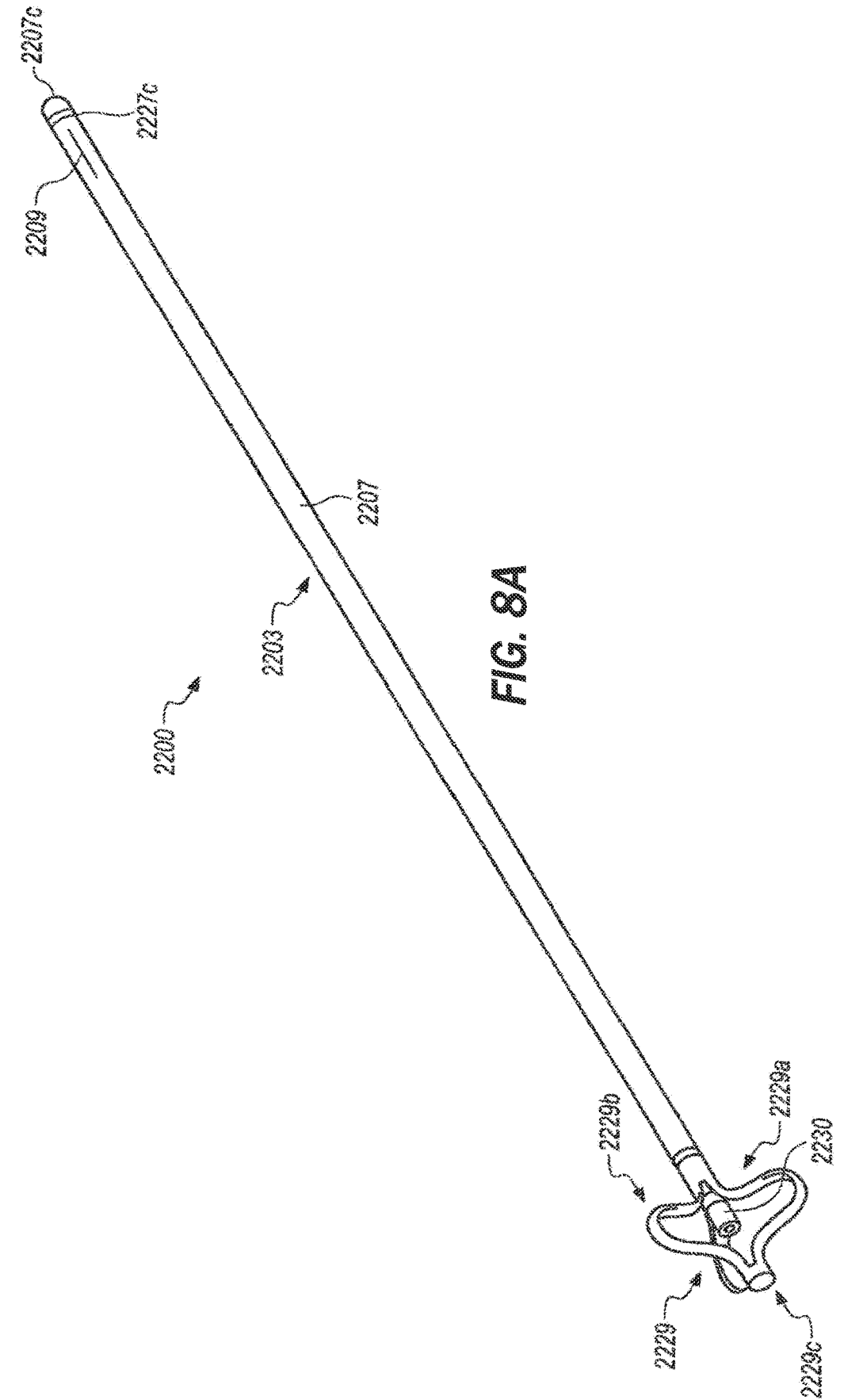
FIGS. 8A-E are perspective, side and cross-sectional views of shunts constructed according to alternative embodiments of the disclosed inventions.

The shunt body 2203 can have an elongate cylindrical configuration as depicted in FIG. 8A and extend between the distal 2202 and proximal 2204 portions of the shunt. Shunt body comprises CSF lumen 2207, e.g., as illustrated in the cross-section views of FIGS. 8C-D. Shunt body 2203 can include an elastomeric polymer(s) suitable for implant applications including, but not limited to, silicone, polyurethane, polycarbonate urethane, thermoplastic polyurethane, aromatic or aliphatic polycarbonate thermoplastic polyurethane, silicone/polyurethane blends (e.g., thermoplastic silicone polycarbonate polyurethane comprising 20% silicone copolymer), or polyurethane silicone blends (e.g., polyurethane silicone copolymer). The durometer of the elastomer shunt body 2203 can range from about 15 A to about 80 A; for a silicone-based shunt body, the durometer can range from about 15 A to about 80 A, and for a urethane-based shunt body, the durometer can range from about 55 A to about 80 A. A shunt body 2203 comprised of an elastomeric polymer(s) advantageously resists thrombus formation on the portions of the implanted shunt in the blood flow of the IPS and jugular vein. Optionally, shunt 2200 can include an anti-thrombotic coating to prevent thrombus formation including, but not limited to, heparin-based or phosphorylcholine-based anti-thrombotic coatings. To further prevent thrombus formation, the length of shunt body 2203 can be configured such that the proximal portion 2204 and valve 2209 are located proximal to the IPS-JV junction 118 (e.g., by 0.25" or more) when implanted in the patient's vasculature; junction 118, a location where the IPS and JV blood flows intersect, can experience more turbulent blood flow and have a higher risk for thrombus formation on an implant and valve portion placed in the junction as compared to a location where the proximal portion of the shunt and valve are placed more proximally in the jugular vein, away from junction 118.

Figures 8B, 8C:
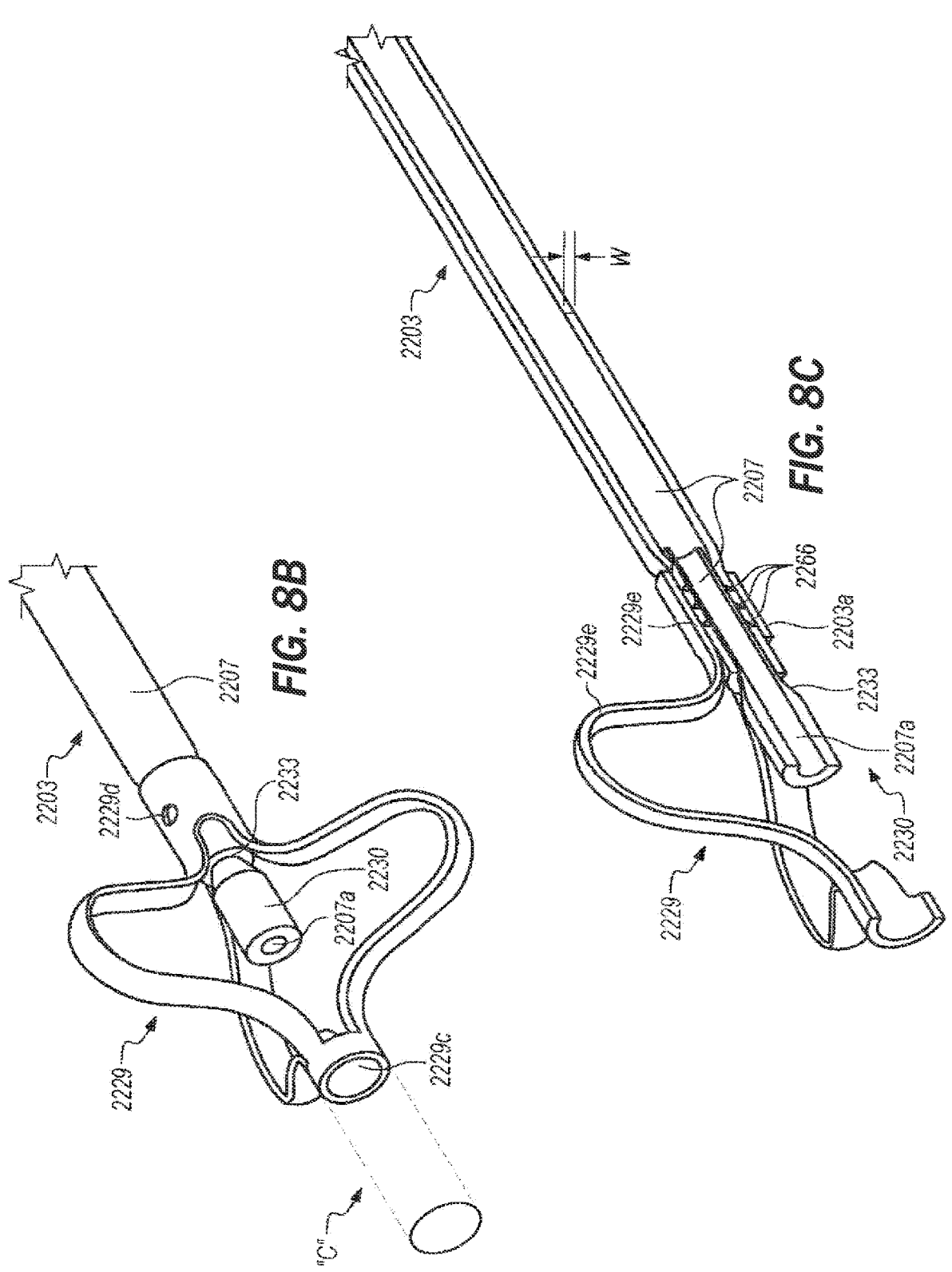

FIG. 8C illustrates a cross section of shunt 2200. The cross section of shunt body 2203 includes a shunt body wall thickness "W" in FIG. 8C. The wall thickness of an elastomer shunt body 2203 can range from about 0.001 inch to about 0.010 inch. The diameter of the CSF lumen 2207 of shunt 2200 can range from about 0.010 inch to about 0.020 inch. The outer diameter of shunt body 2203 can range from about 0.006 inch to about 0.040 inch. The length of shunt body 2203 can range from about 0.25" to 3.0" (6.35 mm 76.2 mm) to or more.

Figures 8D, 8E:
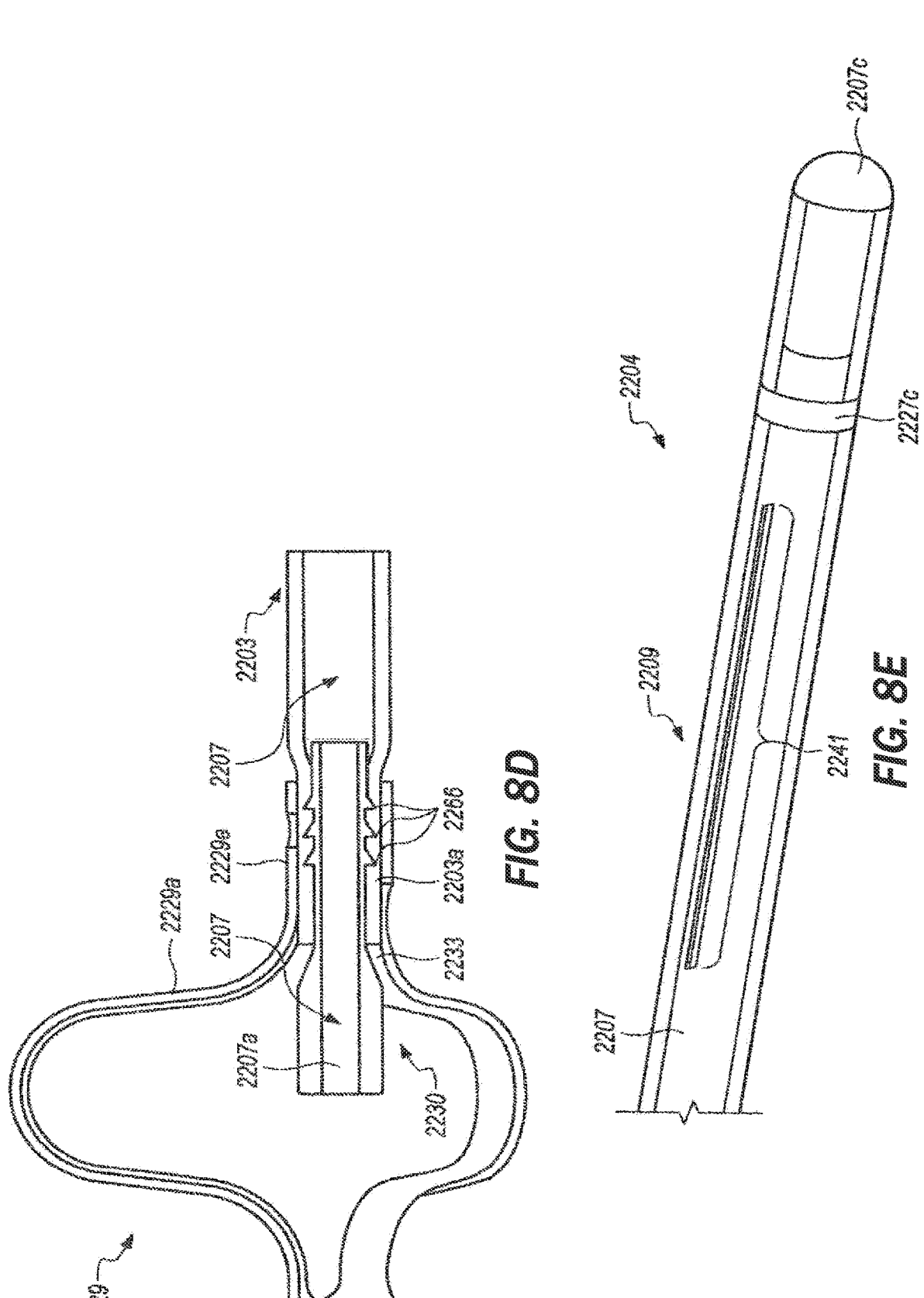

FIGS. 8B-D illustrate distal portion 2202 of shunt 2200. With reference to FIG. 8B, retaining element 2230 comprises a radiopaque material (e.g., gold or other radiopaque material disclosed herein) and the distal portion 2207a of CSF lumen 2207 (further described herein). Anchoring mechanism 2229 can include a radiopaque marker located in the distal collar 2229c. When shunt 2200 is deployed from a shunt delivery catheter, anchoring mechanism 2229 transitions (e.g., self-expands) from a compressed configuration within the delivery catheter (e.g., denoted by the dotted line portion "C" marked on FIG. 8B) to its open or deployed configuration shown in FIG. 8B; during deployment, the clinician can observe the marker of distal collar 2229c move toward the radiopaque retaining element 2230 to confirm that the distal anchoring mechanism 2229 has properly transitioned to its deployed state in CP angle cistern 138.

FIGS. 8C-D illustrate cross sections of the distal portion 2202 of shunt 2200 and the connection between distal anchoring mechanism 2229 and shunt body 2203 using one embodiment of a retaining element 2230. Retaining element 2230 includes a lumen that forms the distal or CSF inflow portion 2207a of CSF lumen 2207 of the shunt and embodiments can have the same range of internal diameters as described above for CSF lumen 2207 of shunt body 2203. Retaining element 2230 further includes a tapered portion 2233 to accommodate a curved portion of distal anchoring mechanism arms 2229a when the distal anchoring mechanism 2229 is in a compressed or delivery configuration; tapered portion 2233 also prevents retaining element 2230 from slipping proximally through the proximal portion 2229e of distal anchoring mechanism 2229 (e.g., during assembly).

Figures 10A, 10B, 10C, 10D:
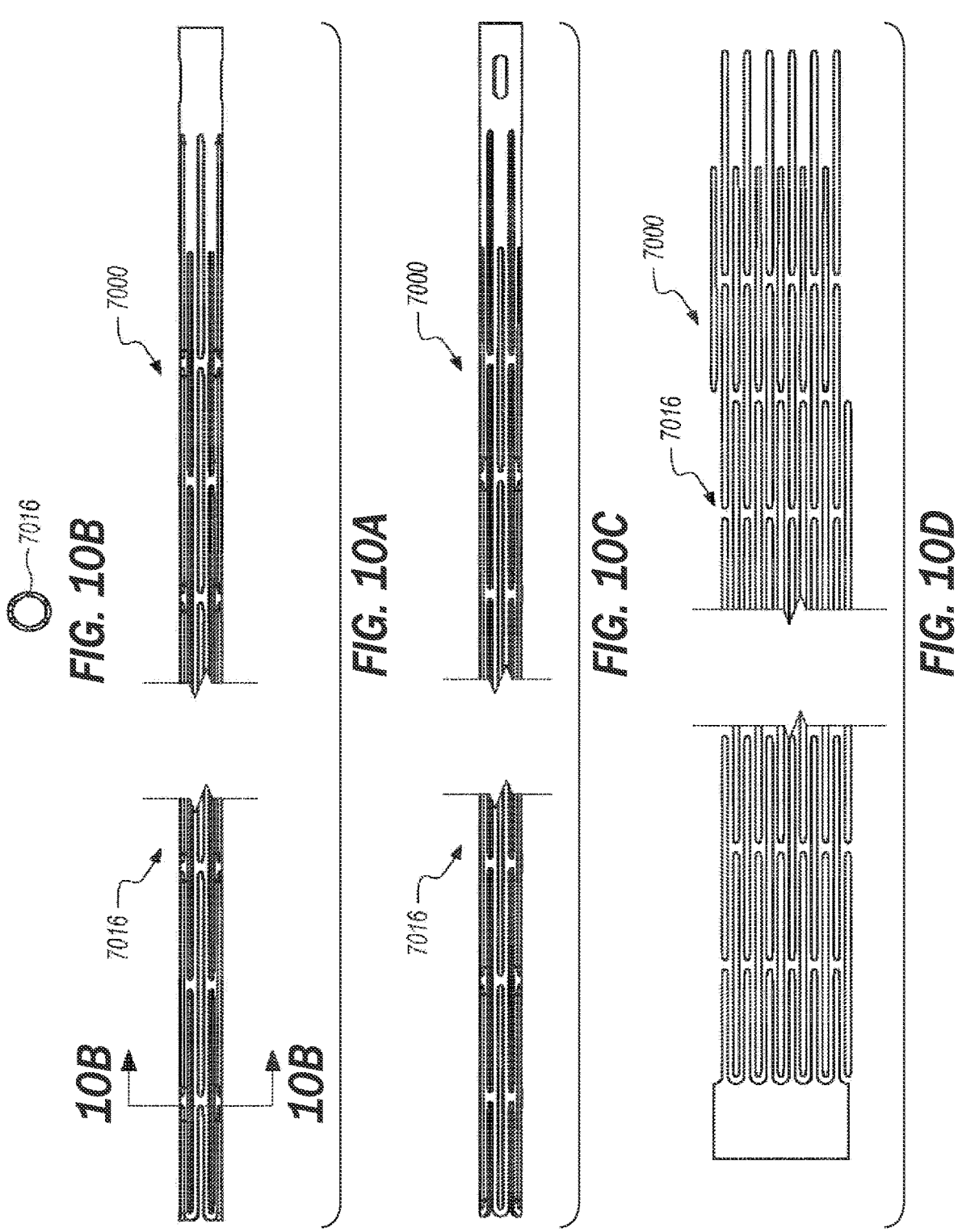
Figures 11A, 11B, 11C:
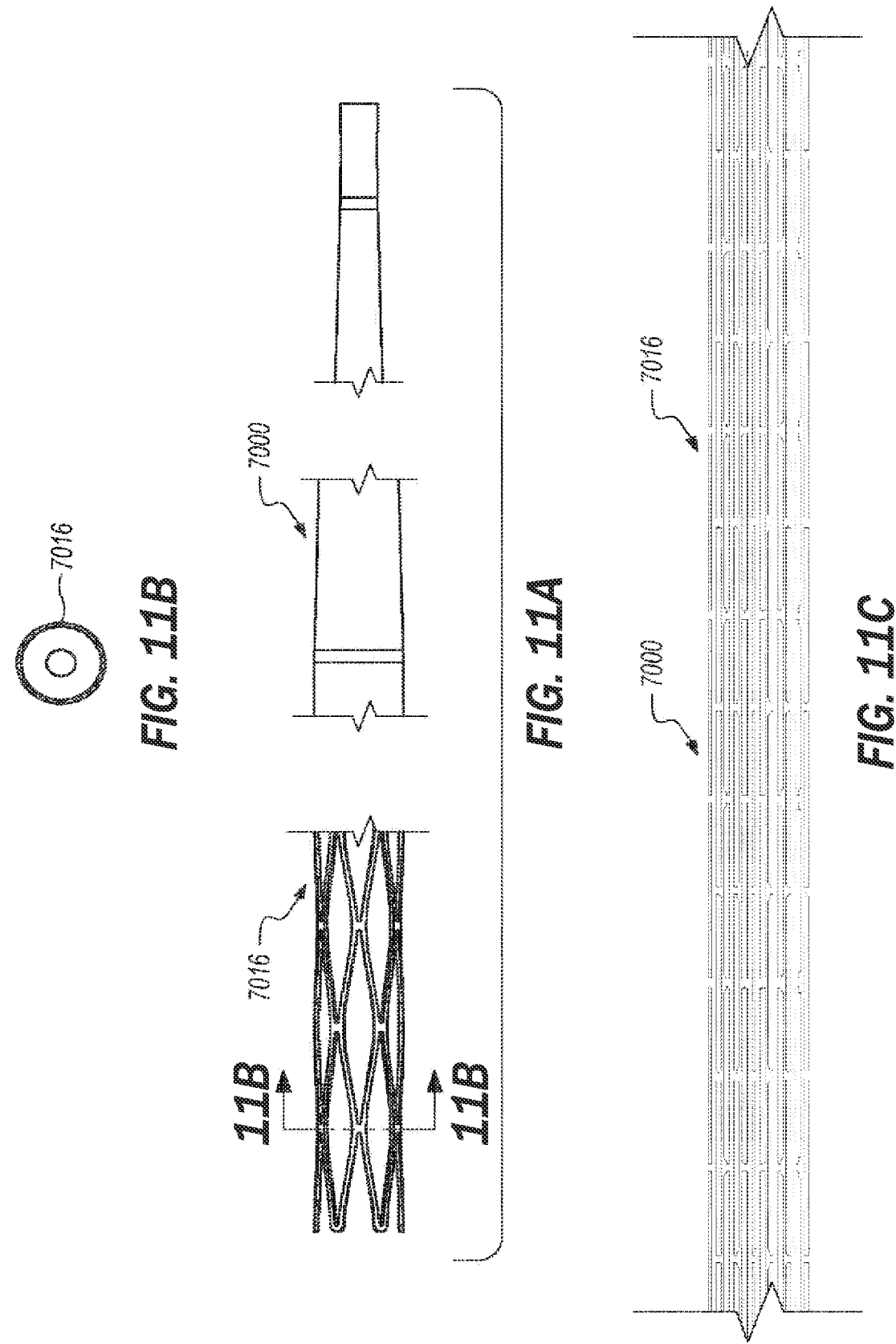
Figures 12A, 12B, 12C, 12D:
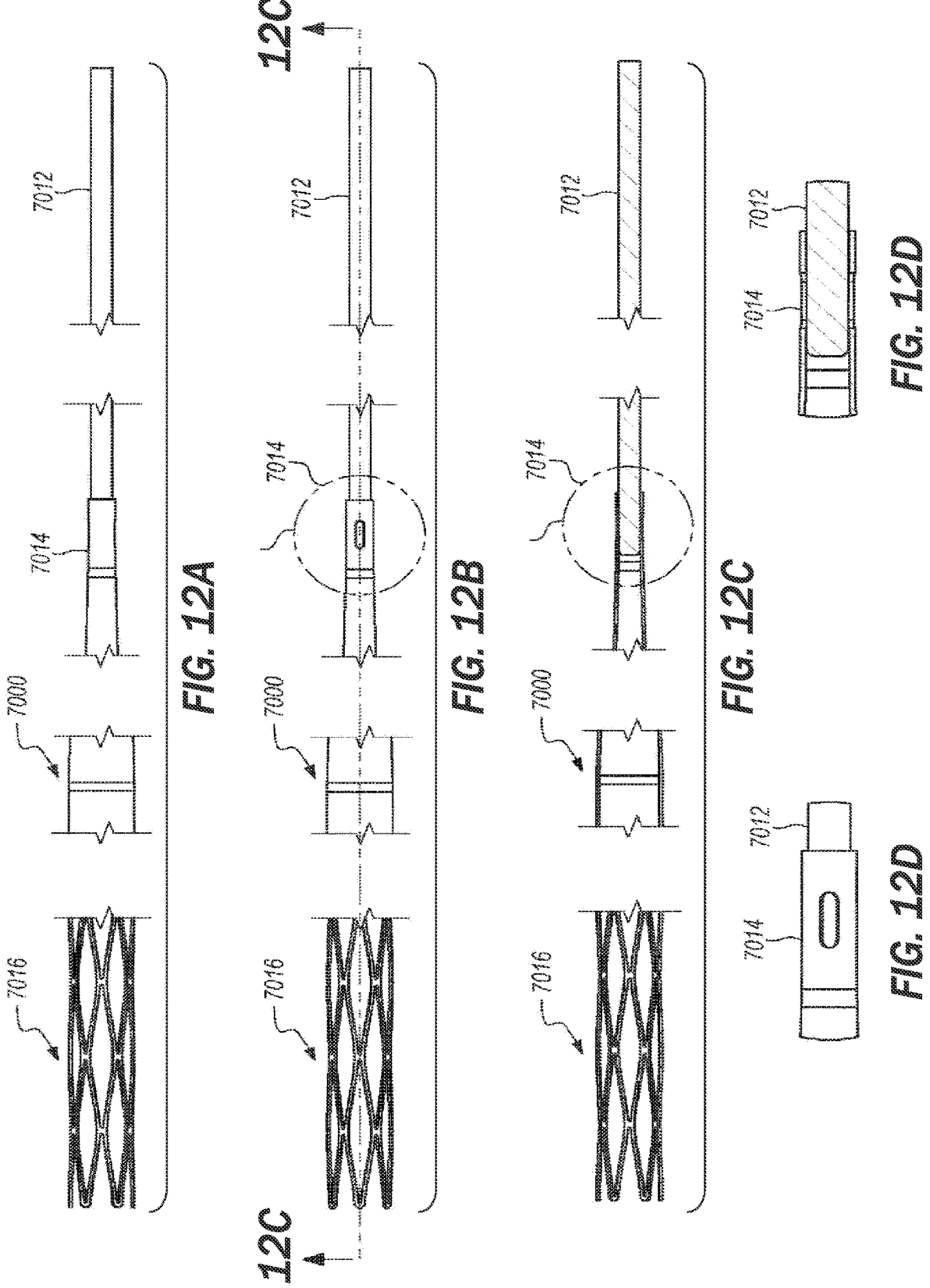

The distal portion 2203a of shunt body 2203 is secured within the distal anchoring mechanism 2229. As shown in FIGS. 8C-D, distal portion 2203a of shunt body 2203 is compressed between the outer surface of retaining element 2203 and inner surface of the proximal portion 2229e of distal anchoring mechanism 2229. For example, distal portion 2229e of distal anchoring mechanism 2229 can be compressed (e.g., crimped, swaged) over the distal portion 2203a of the shunt body and retaining element 2230. Further, retaining element 2230 can include retaining features 2266 (e.g., circumferential threads as shown in FIGS. 10C-D, barbs, tines, hooks, or the like) to secure the distal portion 2203a of shunt body 2203 over retaining element 2230 and within the proximal portion 2229e of distal anchoring mechanism 2229.

FIG. 8E shows proximal portion 2204 of shunt 2200. Proximal portion 2204 includes a one-way valve 2209. Valve 2209 comprises a slit valve configuration with a single slit 2241 aligned with the longitudinal axis of shunt body 2203. This alignment can advantageously resist thrombus formation when implanted as it is also aligned generally with the direction of blood flow through the jugular vein and minimizes blood turbulence across the surface of proximal portion 2204 of the shunt. Proximal portion 2204 further includes a radiopaque marker 2227c, the marker may be disposed between a proximal plug 2207c and the valve 2209, or the plug 2207c may include radiopaque materials. The radiopaque marker 2227c is configured to assist shunt visualization in a patient during follow up clinical visits. The proximal plug 2207c is configured to close the proximal opening of the lumen 2207 of the shunt 2200.

Embodiments of valve 2209 can include one slit 2241 (e.g., as shown in FIG. 8E) or multiple slits 2241 located around the circumference of shunt body 2203 to achieve a desired opening or cracking pressure for the valve and/or target CSF flow rate at a nominal differential between ICP and venous blood pressure (e.g., any of the opening or cracking pressures described herein, any of the CSF flow rates described herein). The slit 2241 can be orthogonal to the surface of shunt body 2203 (e.g., as shown in FIG. 8E) or angled relative to such surface. Each slit 2241 can range from about 1 to 3 mm, or longer. Slit 2241 can be located in the proximal portion 2204 of shunt 2200 (e.g., as shown in FIG. 8E) or located more distally or proximally (e.g., extending to the proximal end of shunt 2200 and/or into plug 2207c described below). With a cylindrically configured shunt body 2203, the hoop strength of shunt body 2203 about slit 2241 prevents backflow of fluid (e.g., blood) through valve into CSF lumen 2207; for example, the valve remains closed and does not allow blood to leak into CSF lumen 2207 when venous blood pressures on the exterior of the shunt elevate above CSF pressure in the shunt lumen 2207 and intracranial compartment (e.g., CP angle cistern 138). Indeed, embodiments of valve 2209 have demonstrated backflow prevention with simulated venous blood pressures exceeding intracranial pressures by more than 175 mm Hg.

The proximal portion of CSF lumen 2007 can include a plug 2207c to close CSF lumen 2207 at its proximal end. Plug 2207c can comprise the same elastomeric material of shunt body 2203 or any of the other polymeric materials disclosed herein. Shunt 2200 can also include a radiopaque marker in the proximal portion of the shunt body 2203. Plug 2207c can be doped with a radiopaque material (e.g., barium sulfate, tantalum, or the like) or plug 2207c and/or proximal portion 2204 of the shunt can include a marker band comprising any of the radiopaque materials disclosed herein (e.g., a marker can be embedded in plug 2207c, shunt body 2203, or fixed thereto). The plug 2207c can have an atraumatic configuration (e.g., rounded end), as shown in FIG. 8E, or a more elongate tapering configuration, or be squared off with respect to the longitudinal axis of shunt body 2203.

FIGS. 9-13B illustrates an embodiment of a shunt delivery shuttle 7000 for translating and deploying a shunt 2200 (e.g., embodiments of shunt 2200 illustrated in FIGS. 8A-E) through the second lumen 3305 of a delivery catheter 3304 (e.g., any of the delivery catheter embodiments disclosed herein including the delivery catheter illustrated in FIG. 14A-E). The shunt delivery shuttle 7000 includes a distal shuttle portion 7016 (e.g., mesh, braid, shroud, stent-like, funnel-like, tubular body, or other configurations), coupled to an elongate proximal pusher 7012 (e.g., wire or elongated pushing member) via a junction 7014. The distal shuttle portion 7016 of the shunt delivery shuttle 7000 comprises a proximal portion 7016a and a distal portion 7016b, having a lumen 7018 extending therebetween. The distal shuttle portion 7016 of the shunt delivery shuttle 7000 is configured to receive, retain, push and/or shuttle the shunt 2200. As illustrated in FIGS. 9A, 11A, 12A-C and 13C, the proximal portion 7016a of the distal shuttle portion 7016 tapers toward junction 7014.

Figures 9, 9A:
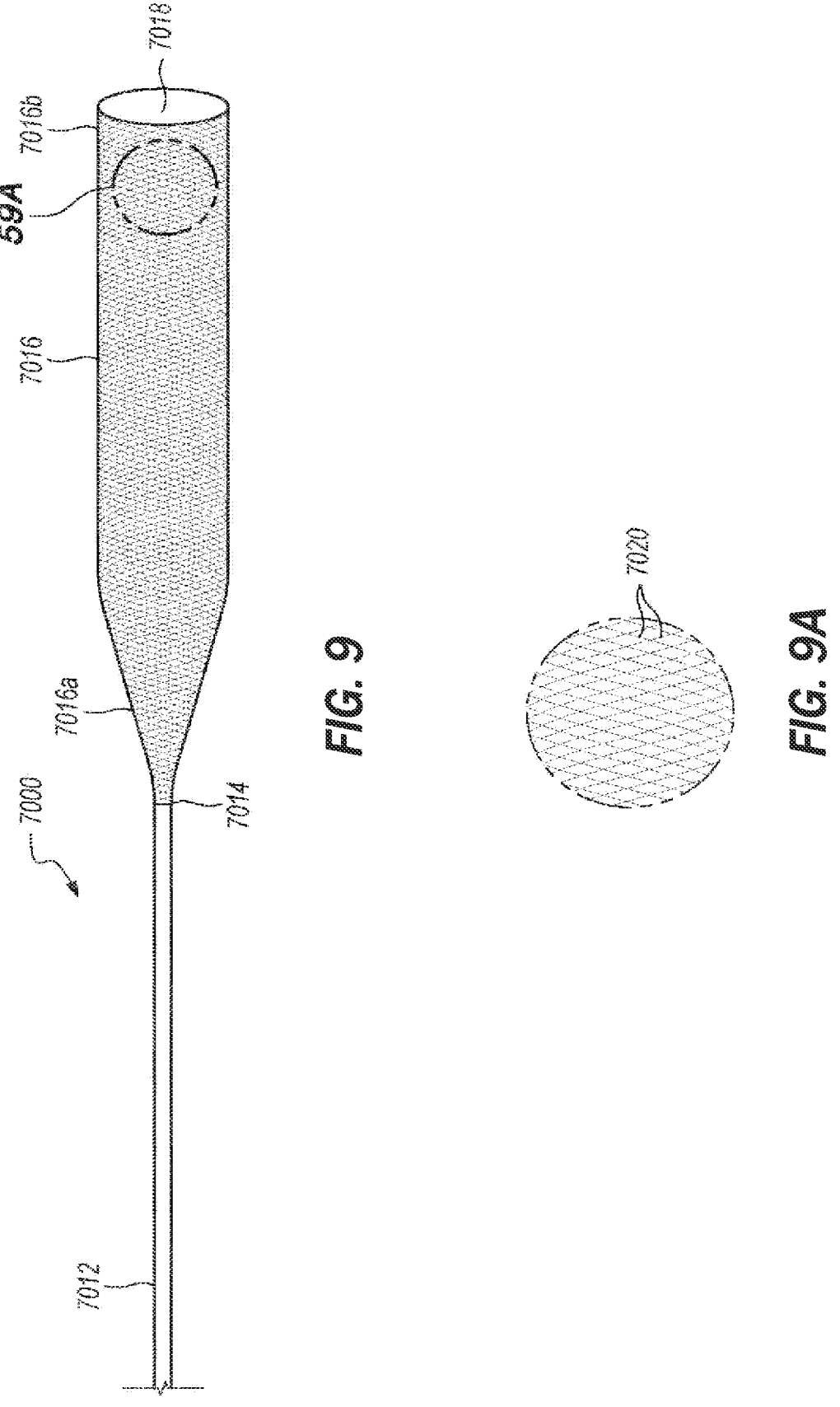

The distal shuttle portion 7016 of the shunt delivery shuttle 7000 can comprise a self-expanding braid, and is shown in an expanded configuration in FIG. 9. The distal shuttle portion 7016 is configured to receive shunt 2200 (e.g., within the lumen 7018) and is configured to compress and elongate (e.g., FIG. 13A-B) suitable for translation within the second lumen 3305 of the delivery catheter for translating the shunt 2000 through the catheter, into the implantation site of a patient. With a lined lumen (e.g., PTFE-lined second lumen of delivery catheter 3304), the distal shuttle portion 7016 of the shunt delivery shuttle 7000 facilitates smooth transition of an elastomeric shunt 2200 through the delivery catheter. The expanded or resting diameter of distal shuttle portion 7016 of the shunt delivery shuttle 7000 can range from about 0.5 mm to about 6 mm. The compressed length of the shunt delivery shuttle 7000 (e.g., when compressed in a delivery catheter lumen) can range from about 0.25" to 3.0" (6.35 mm 76.2 mm) or more.

The distal shuttle portion 7016 of the shunt delivery shuttle 7000 includes multiple filaments 7020 that are weaved to form the braid structure, as illustrated by the inset of FIG. 9A. Filaments can comprise Nitinol (e.g., heat-set), stainless steel, or a polymer (e.g., PTFE, HDPE, PET, PEEK, Kevlar). Embodiments of the distal shuttle portion 7016 of the shunt delivery shuttle 7000 can include 8 to 144 filaments. Filaments 7020 of the distal shuttle portion 7016 can have round or non-round cross-sections; round cross-section filaments can have a diameter from about 0.0002 inch to about 0.005 inch. Filaments 7020 can be cut in the distal portion 7016b of the distal shuttle portion 7016 (e.g., as illustrated in FIG. 9), rounded, or braided back proximally toward the distal shuttle portion 7016 midsection to create a more atraumatic profile for the distal portion 7016b of the distal shuttle portion 7016.

The elongate proximal pusher 7012 can have a round or non-round cross-sectional profile. Embodiments of elongate proximal pusher 7012 with a round cross section can have a diameter of about 0.0006 to about 0.030 inch. The elongate proximal pusher 7012 can be solid or include a lumen to accommodate other delivery assembly components. Nitinol, stainless steel, or other like materials can be used for elongate proximal pusher 7012, provided the overall design provides sufficient column strength to deliver a shunt 2200 in the shunt delivery shuttle 7000 through a delivery catheter lumen and into a target implant site. The distal portion of the elongate proximal pusher 7012 can include a tapered grind or other features (e.g., cuts, slots, kerfs or the like) to increase the flexibility of such distal portion, which can facilitate shunt translation through the delivery catheter when the catheter is being used in tortuous anatomy. Junction 7014 can be formed by gathering the proximal ends of the filaments 4320 of the distal shuttle portion 7016 of the shunt delivery shuttle 7000 over the distal portion of the elongate proximal pusher 7012 and using a heat shrink material over the filaments and wire, by using a direct connection (e.g., by adhesive or welding, e.g., gathering the filaments over the wire and under a radiopaque marker band), or using any of the shunt-tether interlock configurations disclosed herein.

Alternate embodiments of shunt delivery shuttle 7000 can include any of the anchor 700 configurations disclosed herein as a substitute for the distal shuttle portion 7016 of the shunt delivery shuttle 7000 for translating shunt 2200 through delivery catheter 3304. For example, as shown in FIGS. 10A-13C, the shunt delivery shuttle 7000 can be formed from a hypo tube with a wall thickness from about 0.0005 inch to about 0.004 inch. The strut width of the shunt delivery shuttle 7000 can range from about 0.0002 inch to about 0.003 inch; the strut width can vary along the length of the shunt delivery shuttle 7000 (e.g., creating a stiffer proximal portion of the shunt delivery shuttle 7000 to facilitate translation of the shunt through the delivery catheter lumen and a more flexible distal portion of the shunt delivery shuttle 7000 radially capture shunt 2200). FIGS.

12A-12E illustrate alternative junction 7014 between the distal shuttle portion 7016 of the shunt delivery shuttle 7000 and the elongate proximal pusher 7012, the junction 7014 uses any suitable coupling mechanism or technique.

Figure 13A:
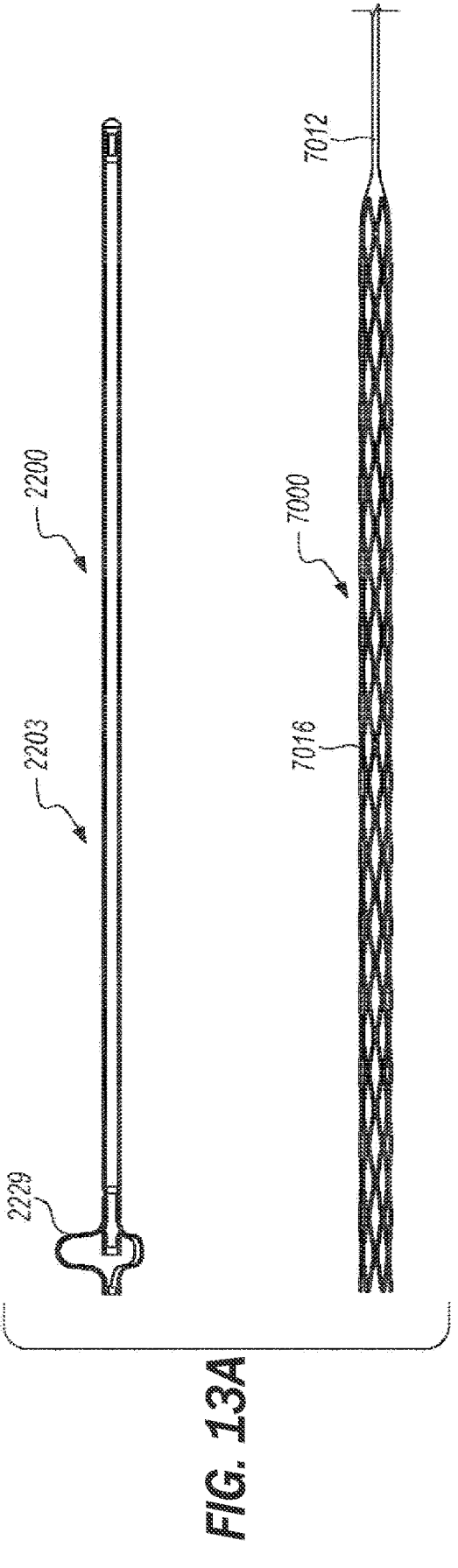
FIGS. 13A-C are perspective views of a shunt and a shunt delivery shuttle interface according to embodiments of the disclosed inventions.
Figures 13B, 13C:
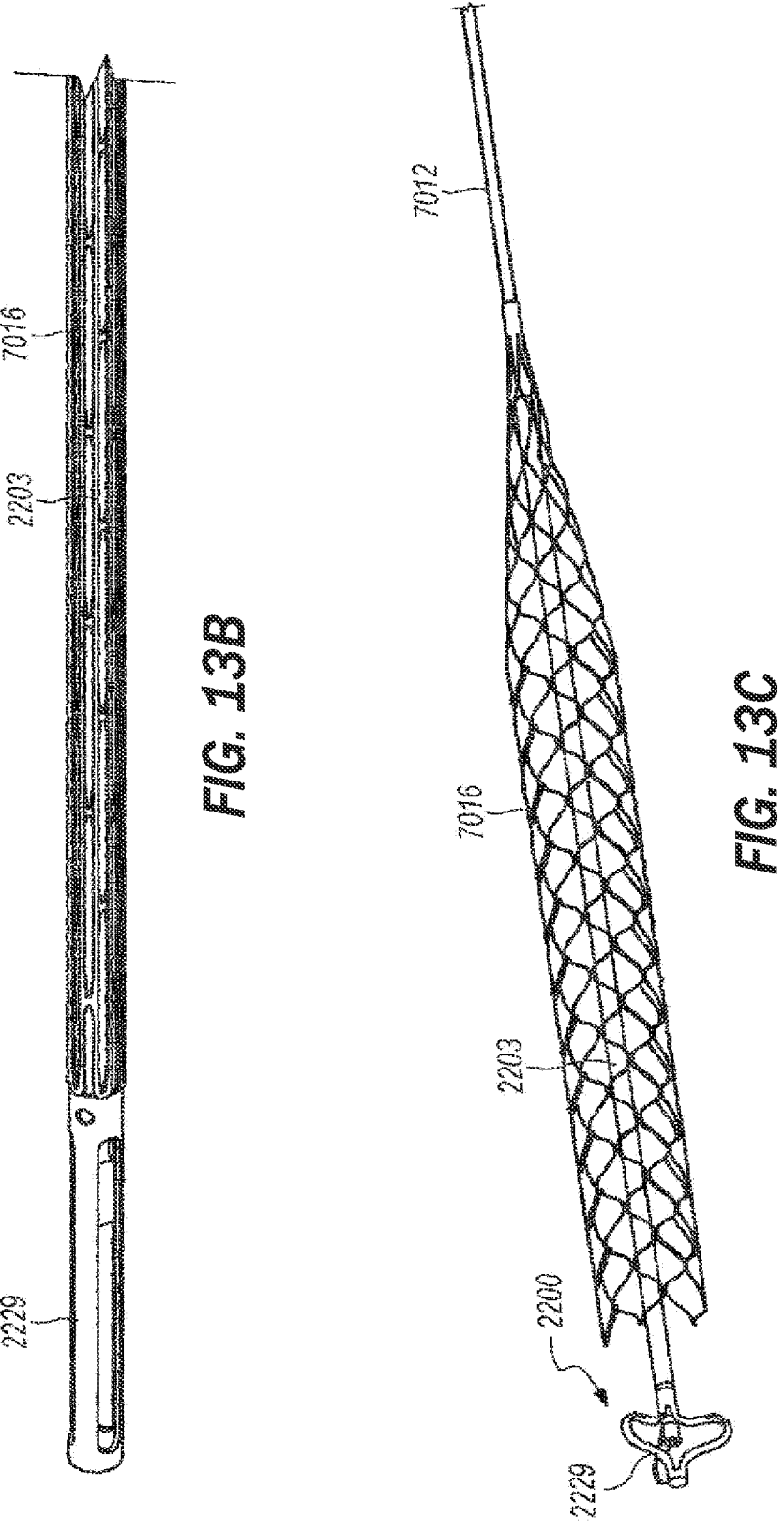

FIGS. 13A-C illustrate the shunt and the shunt delivery shuttle according to the embodiments of the invention. FIG. 13A shows the shunt 2200 and the shunt delivery shuttle 7000 separately, while FIGS. 13B and 13C show the interface between the shunt 2200 and the shunt delivery shuttle 7000. The shunt delivery shuttle 7000 is configured to be at least partially positioned within the lumen of, and movable relative to, the delivery catheter. The distal shuttle portion 7016 of the shunt delivery shuttle 7000 is configured to collapse around the elongate shunt body 2203 (FIG. 13B) to thereby transport the shunt body 2203 through the delivery catheter lumen, wherein the distal shuttle portion 7016 self-expands (FIG. 13C) to release the shunt body 2203 when the distal shuttle portion 7000 is advanced out of the delivery catheter lumen through the opening of the tissue penetrating element.

FIGS. 14A-E illustrate another embodiment of the delivery catheter 3304 embodiments described in connection with FIGS. 4A-I, 5, 6A-M. For ease in illustration and disclosure, the features, functions, and configurations of the delivery catheter that are the same as in the delivery catheter of the present disclosure (e.g., FIGS. 4A-I, 5, and 6A-M) are incorporated by reference herewith; the differences will be described in further detail below. The delivery catheter illustrated in FIGS. 14A-E has received an elongate guide member 780 through first lumen 3315 of the penetrating element guard or guard member 4000 and delivery catheter 3304. Penetrating element guard 4000 is disposed over penetrating element 3350 to guard against inadvertent punctures in the vasculature while tracking the delivery catheter to the target penetration site in IPS wall 114. As described in connection with FIGS. 5, and 6, the penetrating element guard 4000 can translate proximally over the distal portion of the delivery catheter to expose the penetrating element 3350 at the target penetration site in the IPS.

Figure 14A:
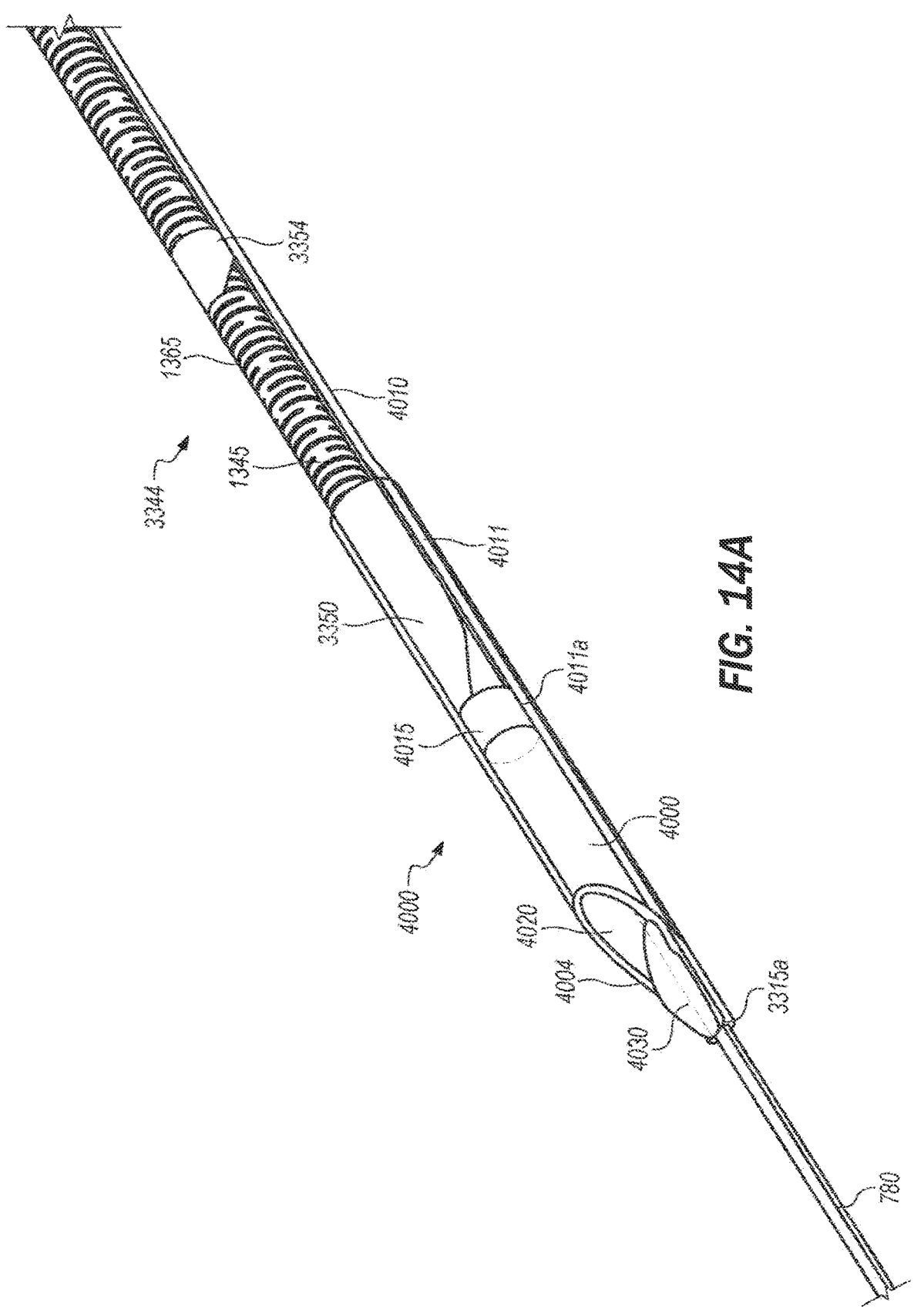
FIGS. 14A-E are perspective and cross-sectional views of a penetrating element guard constructed according to alternative embodiments of the disclosed inventions.
Figures 14B, 14C:
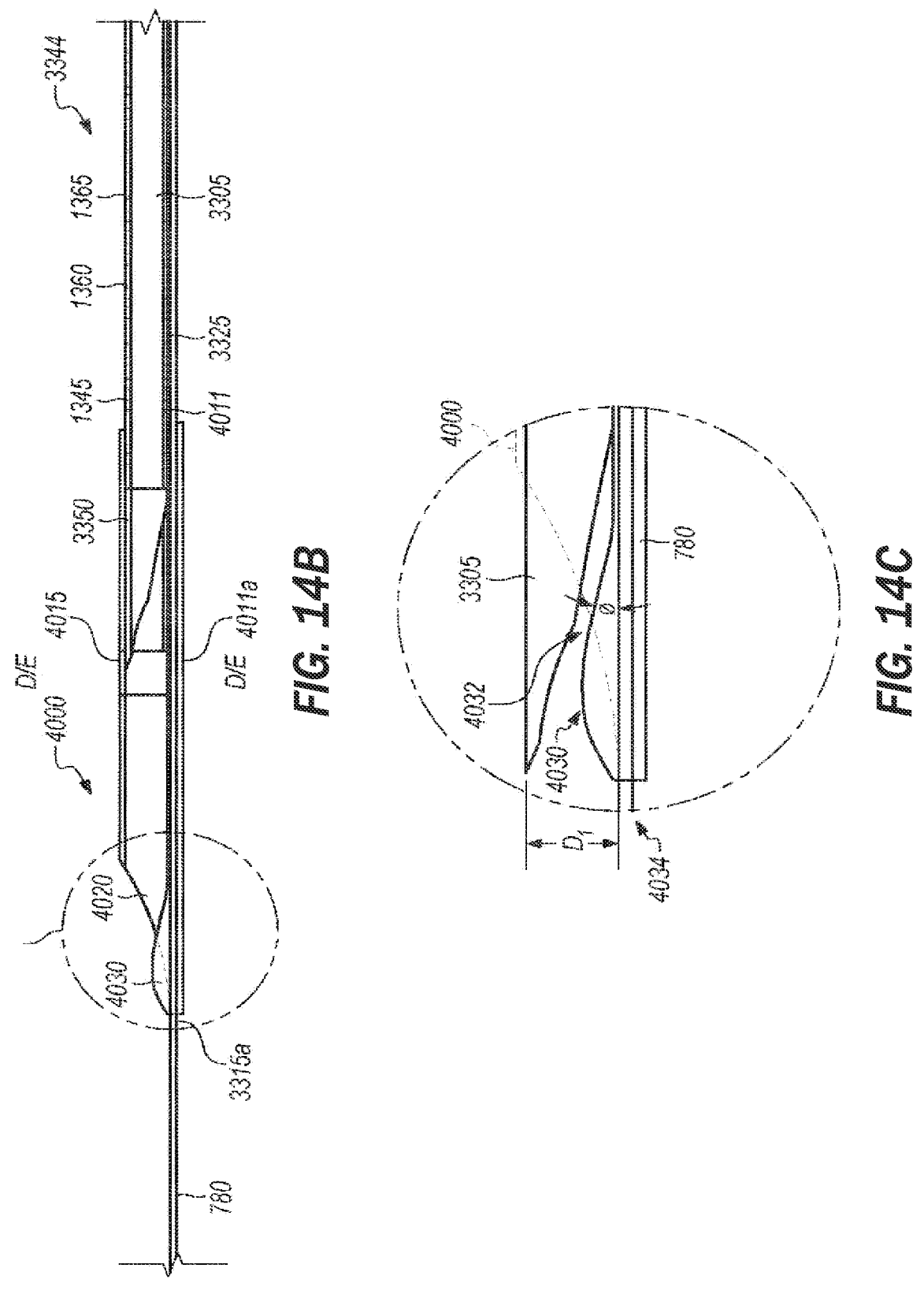

Penetrating element guard 4000 illustrated in FIGS. 14A-E includes a deflecting element 4030 to deflect penetrating element 3350 away from the elongate guide member 780 and towards a target penetration site in the patient's vasculature. FIG. 14B illustrates a cross-section of a distal portion of the delivery catheter including penetrating element guard 4000 and deflecting element 4030. FIG. 14C illustrates further details of the deflecting element 4030 illustrated in FIGS. 14A-B. Deflecting element 4030 includes proximal 4032 and distal 4034 portions. Distal portion 4034 can facilitate delivery catheter access into narrow or tortuous vasculature.

During a shunt deployment procedure, penetrating element guard 4000 is retracted proximally over the delivery catheter to expose penetrating element 3350 at the target penetration site; as the guard 4000 retracts proximally, the proximal portion 4032 of deflecting element 4032 contacts the bevel of penetrating element 3350. As the clinician further retracts penetrating element guard 4000 proximally, deflecting element 4030 (e.g., proximal portion 4032) deflects penetrating element away from elongate guide member 780. To achieve this deflection for penetrating element 3350, the angle of the proximal portion 4032 of deflecting element 4030 relative to the longitudinal axis of elongate guide member 780, as illustrated by angle "@" in FIG. 14C, can range from about five degrees to about 30 degrees, or more. Deflecting element 4030, by increasing the angle of the penetrating element relative to the plane of the elongate guide member 780, increases the distance or separation between the penetrating element tip and guide member 780 (e.g., illustrated as D1 in FIG. 14C). Deflecting element 4030 facilitates tissue puncture in challenging patient anatomies, e.g., in a portion of the IPS 102 or CS 104 that runs relatively parallel to CP angle cistern 138. For example, if the patient has a significant petrous bone overhang that prevents penetration through IPS wall 114 at the first turn 102A of IPS 102 (see FIGS. 2A-B), the clinician can use a delivery catheter and shuttle embodiment as illustrated in FIGS. 14A-E to penetrate IPS wall 114 beyond the petrous bone overhang, for example, between the first 102A and second 102B turns of IPS 102.

Deflecting element 4030 can be added to penetrating element guard 4000 using an ultraviolet light-cured adhesive or epoxy material. Alternatively, penetrating element guard 4000 and deflecting element 4030 can be molded as a single part. Materials for molded embodiments of the penetrating element guard and deflecting element can include Nylon, Pebax, polyurethane, or any other polymeric material disclosed herein for use with guard 4000 or delivery catheter 3304.

Figures 14D, 14E:
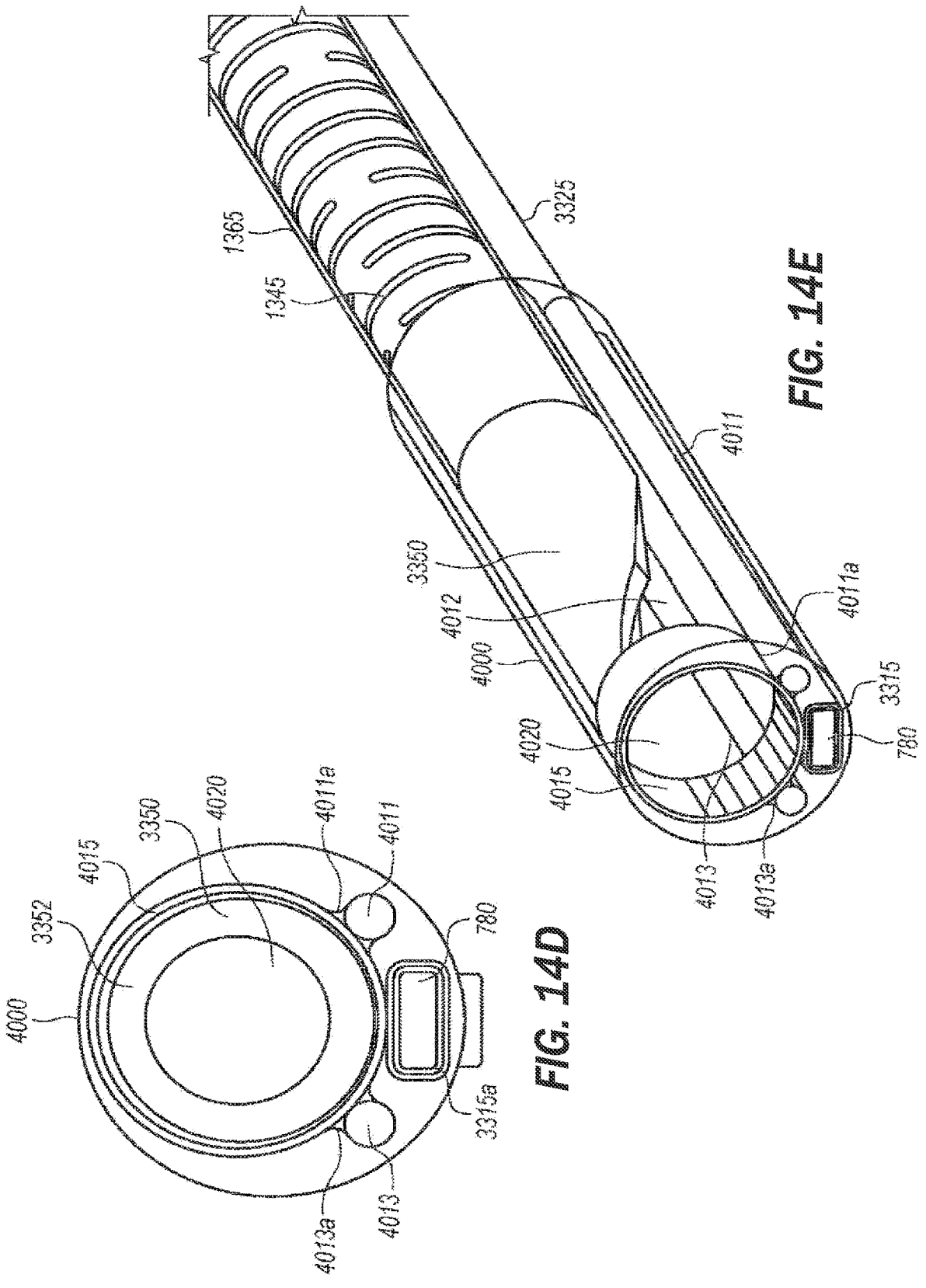

FIGS. 14D-E illustrate cross-section views of the delivery catheter 3304 shown in FIGS. 14A-C at reference line "D/E" of FIG. 14B (e.g., through marker band 4015 embedded in guard 4000). As shown in FIGS. 14D-E, delivery catheter 3304 includes a second shuttle pull wire 4012. Pull wire 4012 includes a distal portion 4013 and connection point 4013a, which are illustrated in FIGS. 14D-E. Delivery catheter 3304 includes a fourth lumen 3335 (not shown) configured to receive the second pull wire 4012. A dual pull wire configuration of delivery catheter 3304 can provide smoother penetrating element guard 4000 retraction proximally over penetrating element and provide smoother distal retraction of guard 4000 to re-cover penetrating element 3350 compared to single pull wire embodiments.

In some embodiments, it can be desirable to deploy a shunt via a delivery system, including, e.g., by employing any of the shunt and/or delivery system embodiments described herein or the like, into regions of the brain beyond the CSF-filled subarachnoid space adjacent target penetration site 500. A procedure to deploy a shunt and/or delivery system into remote regions around the brain, including, e.g., the third ventricle, foramen of Monro, lateral ventricle, and the like, can permit treatment of obstructive hydrocephalus from a transvenous endovascular route, that allows for CSF communication between those remote regions and other subarachnoid spaces and/or a patient's venous system. Those embodiments can allow for simultaneous treatment of both obstructive and communicating hydrocephalus.

Figure 18:
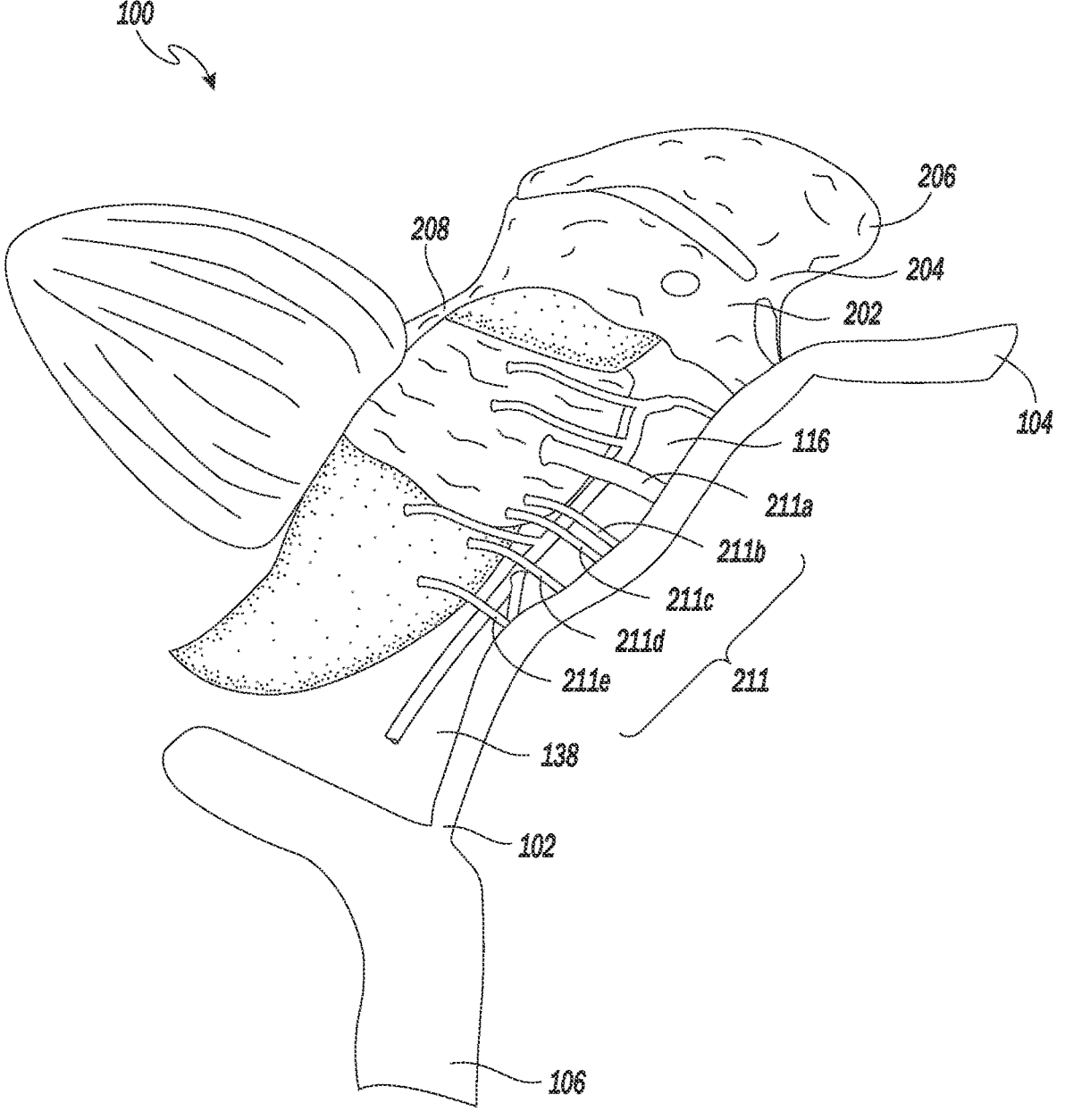
FIG. 18 schematically illustrates the anatomy inside a head of a human patient in the region circumferentially around the base of the patient's skull.

Existing methods and devices for access to the third and lateral ventricles involve invasive surgery through a patient's skull. Referring to FIG. 18, the endovascular methods described herein can provide less invasive and safer, access to, e.g., the third ventricle 202, foramen of Monro 204, lateral ventricle 206, cerebral aqueduct 208, and the like (each space also referred to generally as an intracranial subarachnoid space (ISAS)), than the existing methods and devices.

FIG. 18 illustrates the anatomy inside a patient's head 100 in the region circumferentially around the base of the patient's skull. As further described herein above, inferior petrosal sinus 102 (IPS 102, see also FIGS. 1 and 2A-D) connects cavernous sinus 104 (CS 104) to an internal jugular vein 106 (jugular vein 106) and/or a jugular bulb 108 (not shown in FIG. 118, but see FIGS. 1 and 2A). The IPS 102 is separated from CSF-filled subarachnoid space 116 by the IPS wall 114 and the arachnoid mater 115 (also referred to as arachnoid layer 115), as better shown in FIGS. 2A-B). The CSF-filled arachnoid space 116 includes, e.g., CP angle cistern 138 (see also FIGS. 2A-B) and the like.

The CSF-filled arachnoid space 116 can also include various cranial nerves 211 (e.g., CN V 211a, CN VI 211b, CN VII 211c, CN VIII 211d, CN X 201e) and associated blood vessels. A patient workup can be performed prior to implementing any method or procedure for deploying a delivery system and/or shunt described herein, in order to avoid damage to cranial nerves 210 and blood vessels in and around the IPS 102 and subarachnoid space 116, which can include, e.g., a combination of CT (computed tomography, or coherence tomography) and MRI imaging data and the like, as described herein.

Figure 70:
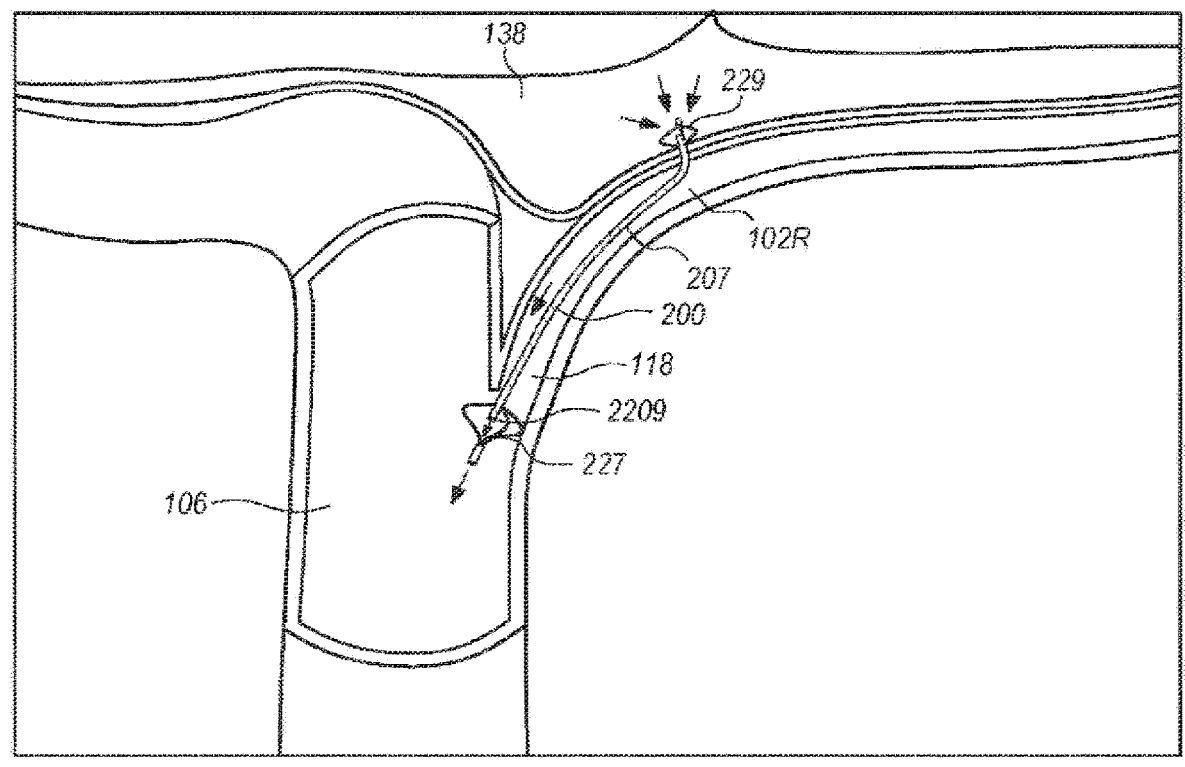

A clinician can make use of any of the devices and/or methods described herein to initially access a patient's subarachnoid space 116. For example, FIGS. 19-26 illustrate an intracranial intervention system 201 and methods of using the same for endovascular navigation of intracranial subarachnoid spaces (ISAS's) within a human head 100, and/or for performing various diagnostic and/or therapeutic procedures within the ISAS's, such as delivering and implanting a shunt, administering a therapy in an ISAS, performing a biopsy of tissue within an ISAS, or other suitable intracranial procedure. The intracranial intervention system 201 comprises a catheter 222. The catheter 222 may comprise any of the delivery catheter 3304, delivery assembly 3304, and/or guide catheter or 3307, and/or components thereof, as described herein, including with respect to FIGS. 7A-70. In other words, the catheter 222 may be a delivery catheter 222 or a guide catheter 222. For instance, the catheter 222 may be a delivery catheter used with or without a guide catheter, similar to delivery catheters 304 and 3304, or it may be a guide catheter similar to guide catheters 307 and 3307 which is used to guide a delivery catheter disposed within lumen of the delivery catheter. The catheter 222 may also include one or more imaging sensors 223, which may be any suitable imaging sensor, such as ultrasound sensors and/or optical coherence tomography sensors, for mapping critical anatomical structures and assisting in navigation of the catheter 222.

Figure 19:
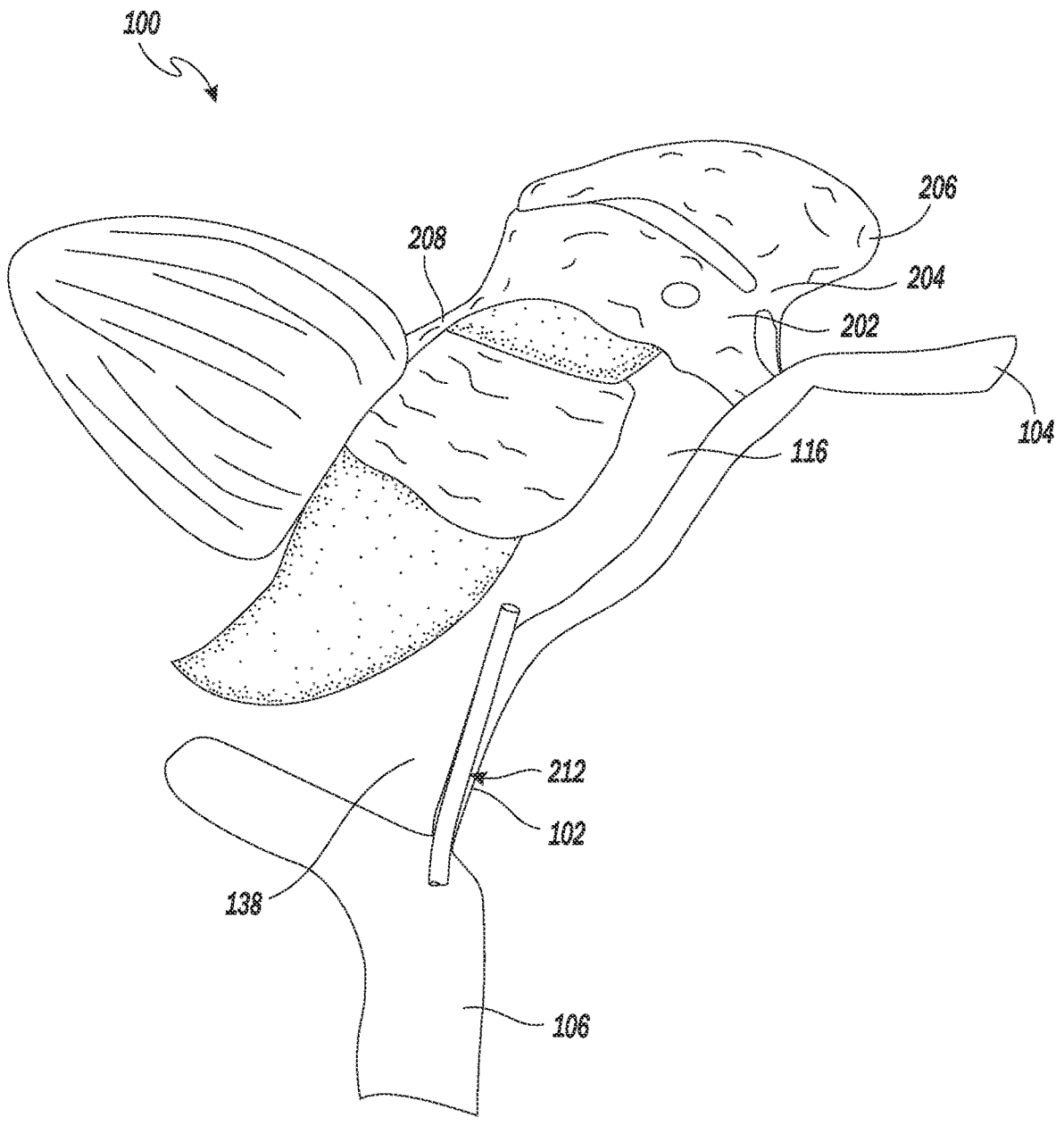
FIGS. 19-22 illustrate an intracranial interventions system and method of use for accessing and deploying a shunt in a third ventricle (a second intracranial subarachnoid space) via a dural venus sinus and a subarachnoid space a first intracranial subarachnoid space).

When catheter 222 is used as a guide catheter, a clinician can utilize the intracranial intervention system 201 and apply force to a proximal end of the catheter 222 to advance a distal end of the catheter 222 through a patient's jugular vein 106. Once the catheter 222 reaches a region proximate the junction 118 (see FIGS. 2A-C) between the patient's jugular bulb 108 and IPS 102 (or CS 104), the clinician can advance a delivery microcatheter, such as delivery catheter 304, 3304 containing a shunt 220, and/or a delivery system such as delivery system 300 through the distal end of the catheter 222 and into a patient's IPS 102 or CS 104. The clinician can guide the delivery microcatheter to a desired deployment location along the IPS wall 114, generally along a curved region of the IPS 102. A penetrating element (e.g., penetrating elements 3350, 1350, and other penetrating elements described herein, such as in description of FIGS. 7A-70, hereafter "penetrating element 3350 etc.") associated with the distal end of the delivery microcatheter 304 etc., 307 etc. or shunt 220 etc. can puncture the IPS wall 114 to access the CSF-filled subarachnoid space 116. In some embodiments, the desired deployment location that is pierced by the penetrating element 3350 etc. can be on IPS wall 114 to access the CP angle cistern 138 of the CSF-filled subarachnoid space 116. In some embodiments, the desired deployment location that is pierced by the penetrating element 3350 etc. can be a venous sinus or other intracranial vessel adjacent a region of CSF-filled subarachnoid space 116, e.g. closer to a patient's ventricle sought to be accessed. In some embodiments, a deployment location immediately proximate a patient's ventricle, e.g., the third ventricle 202, the lateral ventricle 206, or the like, can be selected to avoid passing the delivery microcatheter 3307, 304 through certain regions of the head 100 that could be especially sensitive or could present a likelihood for complications. In this manner, a working port 212 (described below, also referred to as "IPS port 212" can be deployed that permits access between the IPS 102 and the CSF-filled subarachnoid space 116, as illustrated in FIG. 19. In some embodiments, an anchor, in the manner of anchor 700 or any other suitable anchor disclosed herein, can be deployed in the IPS 102 to facilitate the delivery process, as described herein.

The catheter 222 may further comprise a guard, such as the guard 4000 as described herein. The guard 4000 is disposed over and translatable relative to the penetrating element 3350 etc. The catheter 222 includes a working lumen that extends from an opening in a proximal portion of the catheter 222, through a body of the catheter 222, to a distal end opening in the penetrating element 3350 etc. Delivery catheter 304 etc. or guide catheter 307 etc. may also have a one-way valve in, or coupled to, the distal end of the opening of the penetrating element 3350 etc. which is configured to resist and/or prevent CSF leaking from an ISAS into the catheter working lumen. Accordingly, the intracranial intervention system 201 embodies a system for endovascular navigation of ISAS's within a human head 100, and/or performing various diagnostic and/or therapeutic procedures within the ISAS's, such as delivering and implanting a shunt 220 as depicted in FIGS. 19-26 and described herein, administering a therapy in an ISAS, performing a biopsy of tissue within an ISAS, or other suitable procedure.

More specifically, FIGS. 19-26 illustrate an exemplary intracranial intervention system 201 and methods of using the system 201 for accessing and treating the third and lateral ventricles of a human head 100. The intracranial intervention system 201 may include any suitable features and aspects of the shunt delivery assembly 300 described herein. In the example illustrated in FIGS. 74-81, the intracranial intervention system 201 includes the delivery catheter 222, a working port 212, a shunt 220, and/or an optional seeker wire 224.

Figure 20:
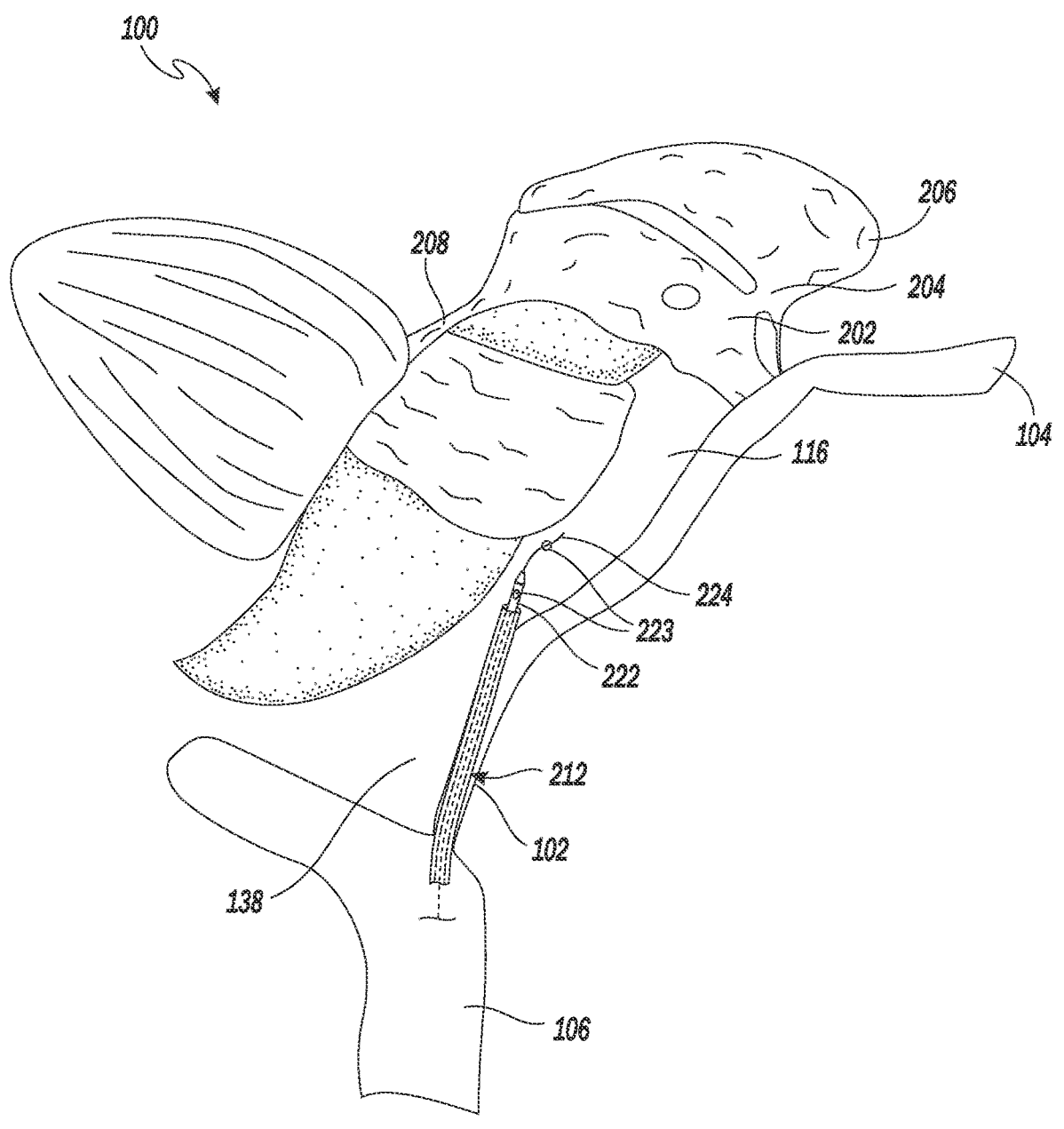

As shown in FIG. 20, the working port 212 is a tubular member having a length to extend from proximal the IPS 102, such as within the jugular vein 106, along a portion of the IPS 102, through the IPS wall 114, and into the CSF-filled subarachnoid space 116. The working port 212 is first deployed between the IPS 102 and the CSF-filled subarachnoid space 116. The working port can include a one-way valve in, or coupled to, the tubular member, which is configured to resist and/or prevent CSF leaking from an ISAS through the port, while allowing endovascular devices (e.g., seeker wire 224, delivery microcatheter 3307 or 304) to access the ISAS through the port.

As depicted in FIG. 20, to minimize intrusion upon or damage to the various structures (e.g., the cranial nerves 211, and blood vessels and the like), the clinician may advance the navigable seeker wire 224 through the working port 212 and out of the distal end of the working port 212 into the CSF-filled subarachnoid space 116. The seeker wire 212 may be a suitable guidewire, such as the guidewire 302 described herein. The seeker wire 212 may also include one or more imaging sensors 223, which may be any suitable imaging sensor, such as ultrasound sensors and/or optical coherence tomography sensors, for mapping critical anatomical structures and assisting in navigation of the seeker wire 212. The clinician may use the seeker wire 212 to identify a suitable path through the CSF-filled subarachnoid space 116 to the third ventricle 206. The seeker wire 224 may have one or more ultrasound or optical computed/coherence tomography sensors for mapping critical anatomical structures as it is advanced through the anatomical structures. For example, the clinician can use imaging data, e.g., a combination of CT and MRI data and the like, to determine an appropriate path for the seeker wire 212 and/or the catheter 222 through the CSF-filled subarachnoid space 116. A suitable path includes one that does not intrude upon cranial nerves and blood vessels in the CSF-filled subarachnoid space, and proceeds between the IPS and other cranial structures, e.g., the brain stem and the like. In some alternative methods of using the delivery system 230, the seeker wire 224 and/or delivery catheter 222 can pass through the IPS wall 114 without the use of an IPS port 212 or working port 212. In other alternative methods, the seeker wire 224 can be advanced from delivery catheter 222 or 304 or guide catheter 307 after the respective catheter has accessed the ISAS.

As also shown in FIG. 20, the catheter 222 (also referred to as a second microcatheter 222) is advanced through the working port 212 along the seeker wire 224. The shunt 220 may be contained in the catheter 222 as it is advanced along the seeker wire 224, or alternatively, the shunt 220 may be inserted into and advanced through the catheter 222 after placement of the catheter 222 at the shunt delivery site.

The distal end of the catheter 222 and seeker wire 212 are advanced through the CSF-filled subarachnoid space 116 toward the floor of the third ventricle 202 in this manner by a clinician pushing on a proximal end of the catheter 222 and seeker wire 212.

Figure 21:
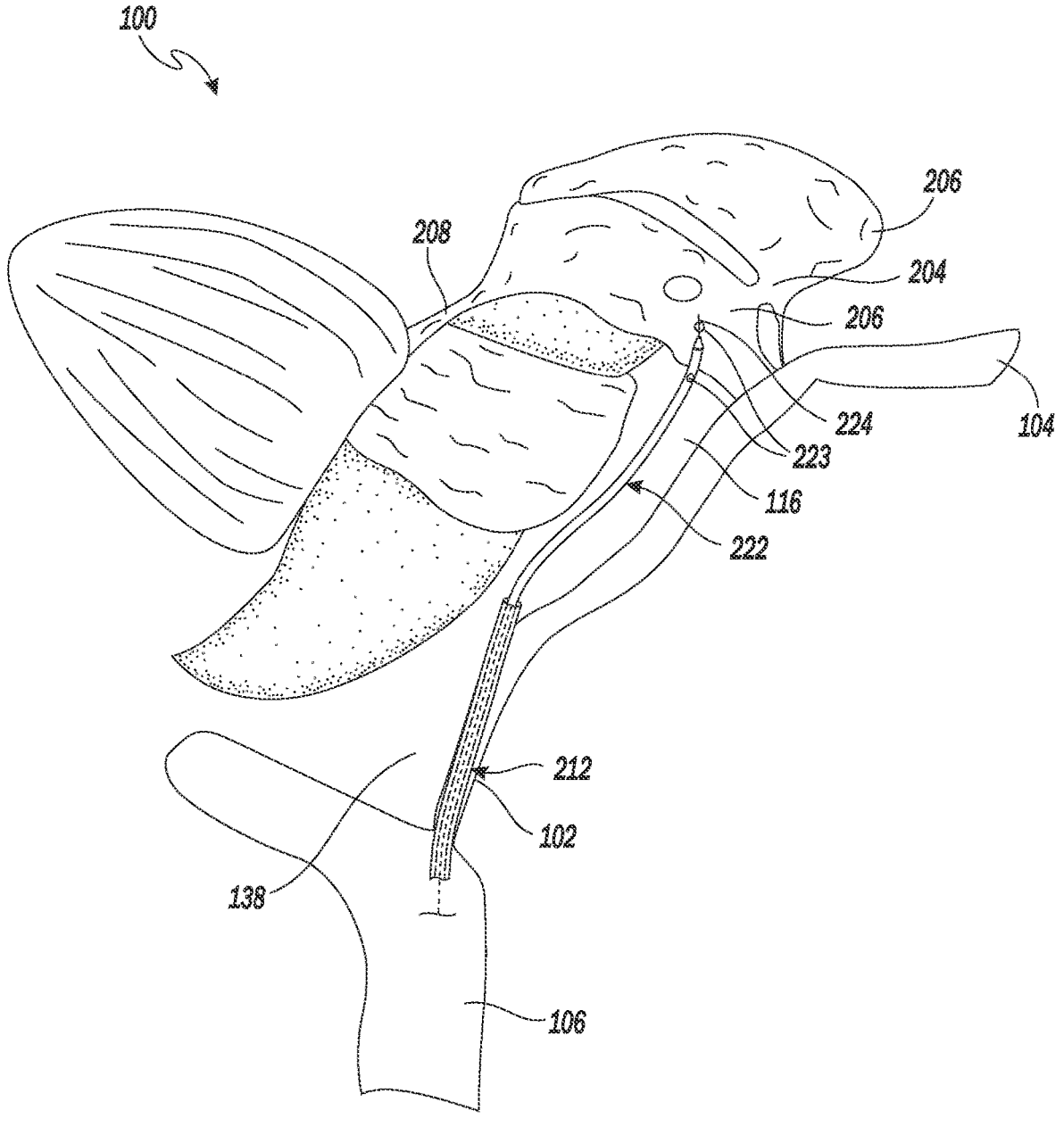

As illustrated in FIG. 21, once reaching the floor of the third ventricle 202, catheter 222, and optionally the seeker wire 212, are advanced through the floor and into the third ventricle 202 itself. The penetrating element 3350 etc. disposed on the distal end of the catheter 222 or the shunt 220 may be utilized to penetrate through the floor of the third ventricle 202 such that the catheter 222 and/or shunt 220 can be advanced through the microcatheter at the desired delivery site along the floor of the third ventricle 202. A physician can select a desired delivery site by repositioning the catheter 222 and/or seeker wire 212, including by retracting the catheter 222 and/or seeker wire 212 slightly and applying a torque to reposition the catheter 222 and/or seeker wire 212, as further described herein, before pushing or advancing it back toward the floor of the third ventricle 202.

Figure 22:
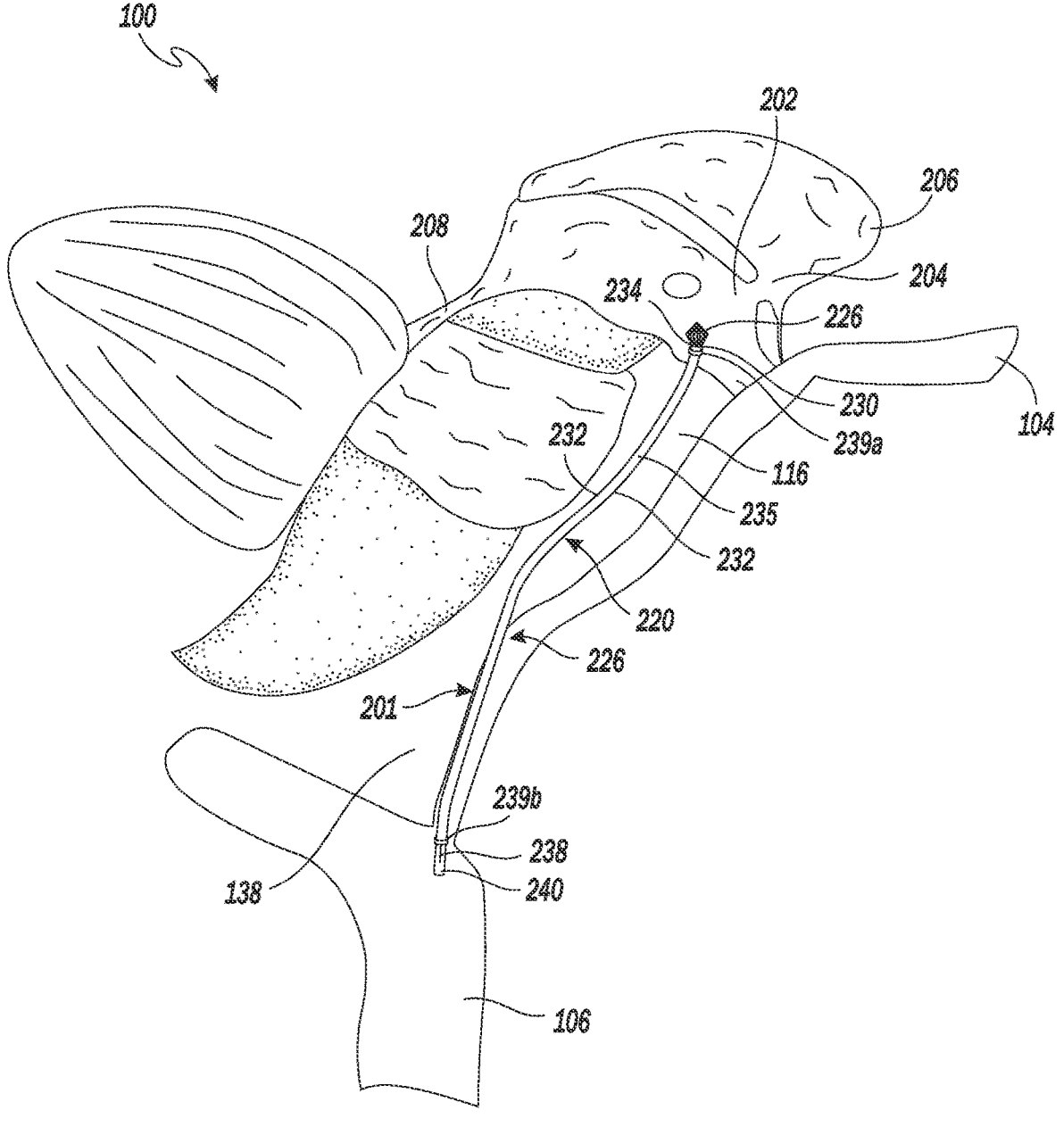

As described above, the catheter 222 may be a delivery catheter or a guide catheter used in conjunction with a delivery microcatheter. In the case that the catheter 222 is a guide catheter 222, the guide catheter 222 is advanced and positioned as described herein, and then the delivery microcatheter, same or similar delivery catheters 304 and 3304, is advanced through the guide catheter 222 until the distal end of the catheter 222 is positioned proximate the distal end of the guide catheter 222. The delivery microcatheter may then be used to deliver a shunt 220, or perform any other diagnostic or therapeutic procedure, as described herein for the catheter 222 when utilized as a delivery catheter. After confirming that the penetrating element has penetrated the floor of the third ventricle 202 between the CSF-filled subarachnoid space 116 and the third ventricle 202 such that a distal portion 230 of the catheter 222 has accessed the third ventricle 202, the clinician advances the shunt 220 by pushing it through the catheter 222 until the distal portion 230 of the shunt 220 is positioned within the third ventricle 202, as illustrated in FIG. 22. The shunt 220 may include a distal anchoring mechanism 226 disposed on the distal end of the shunt 220, such as the self-expanding distal anchoring mechanism 229 described herein or other suitable distal anchoring mechanism described herein. The distal anchoring mechanism 226 deploys once the distal end and distal anchoring mechanism 226 of the shunt 220 have been advanced into the third ventricle 202. The distal anchoring mechanism 226 of the shunt 220 may operate substantially as described herein. As illustrated in FIG. 22, the shunt 220 deployed to the third ventricle 202 is generally longer than a shunt deployed only as far as the CSF-filled subarachnoid space 116, in order to permit drainage of CSF in the third ventricle 202 through the shunt 220 to the patient's internal jugular vein 106 or elsewhere in the patient's venous system.

Accordingly, the shunt 220 has a distal portion 230 configured to be introduced within a first ISAS, for example, the third ventricle 202, foramen of Monro 204, lateral ventricle 206, cerebral aqueduct 208, and the like, via a dural venus sinus (DVS; e.g., the IPS 102 or CS 104) and a second ISAS (e.g., CP angle cistern 138). The first ISAS and second ISAS contain CSF. The shunt distal portion 230 has one or more distal intake openings 234 for receiving CSF from the first ISAS. The shunt 220 also has a main body portion 232 which extends proximally from the distal portion 230 and is configured to extend within a dural venous sinus and a second ISAS, such as the CSF-filled subarachnoid space 116. The main body portion has a shunt lumen 235 which is in fluid communication with distal intake openings 234. The main body portion 230 may also have one or more body intake openings 236 (see FIG. 24) for allowing CSF in the second ISAS to flow into the shunt lumen 235. The shunt 220 has a proximal portion 238 having an outflow opening 240 in fluid communication with the shunt lumen 235. The outflow opening 240 is configured and positioned on the shunt 220 such that when the shunt 220 is deployed in the DVS with the distal portion 230 disposed within the first ISAS and the main body portion 232 is disposed within the DVS and second ISAS, CSF flows from the first ISAS and second ISAS through the respective intake openings 234, 236, through the shunt lumen, out through the outflow opening 240, and, into the venous system of the patient (e.g., the jugular vein 106). The distal anchoring mechanism 226 may also act to position the distal portion 230 of the deployed shunt 220 to maintain the distal intake openings 234 away from the arachnoid layer of the first ISAS. The distal anchoring mechanism 226 may also act to position the distal portion 230 of the deployed shunt 220 to maintain the distal intake openings 234 away from the choroid plexus in the first ISAS. This helps prevent the distal intake openings 234 from being blocked and/or damaging the arachnoid layer and/or choroid plexus. The shunt 220 also has a one-way valve 238 disposed at the proximal end of the shunt 220 for allowing outflow of CSF from the shunt lumen 235 into the venous system, and preventing inflow of venous blood into the shunt lumen 235. The one-way valve 238 may be any suitable one-way valve such as the valve 2209 shown in FIG. 29, which may be a slit valve, duckbill valve, ball-in-cone valve, or any other suitable valve configured to regulate fluid flow through the valve in one direction and stop, check, or resist fluid flow through the valve in the opposite direction. The one-way valve 238 may be located within the shunt lumen 235, or coupled to the proximal portion of the shunt. The shunt 220 may also include one or more radiopaque markers 239 for allowing visualization of the position of the shunt 220 during deployment. For instance, the shunt 220 may have a distal end marker 239*a* on the distal end of the shunt 220, and a valve marker 239*b* located adjacent the one-way valve 238.

In some embodiments, the working port 212 or IPS port 212 between the CSF-filled subarachnoid space 116 and the IPS 102 or CS 104 can be replaced by an anchor mechanism 226 once delivery of the shunt 220 is complete, as illustrated in FIG. 22. The anchor mechanism 228 is configured to provide a permanent opening between the CSF-filled subarachnoid space 116 and the IPS 102 or CS 104, and can further prevent the deployed shunt 220 from unwanted intracranial movement. The anchor mechanism 228 may be any suitable tube, stent, or element and may optionally have an anchoring mechanism same or similar to the anchoring mechanism 229, or other suitable anchoring mechanism, as described herein.

Figure 23:
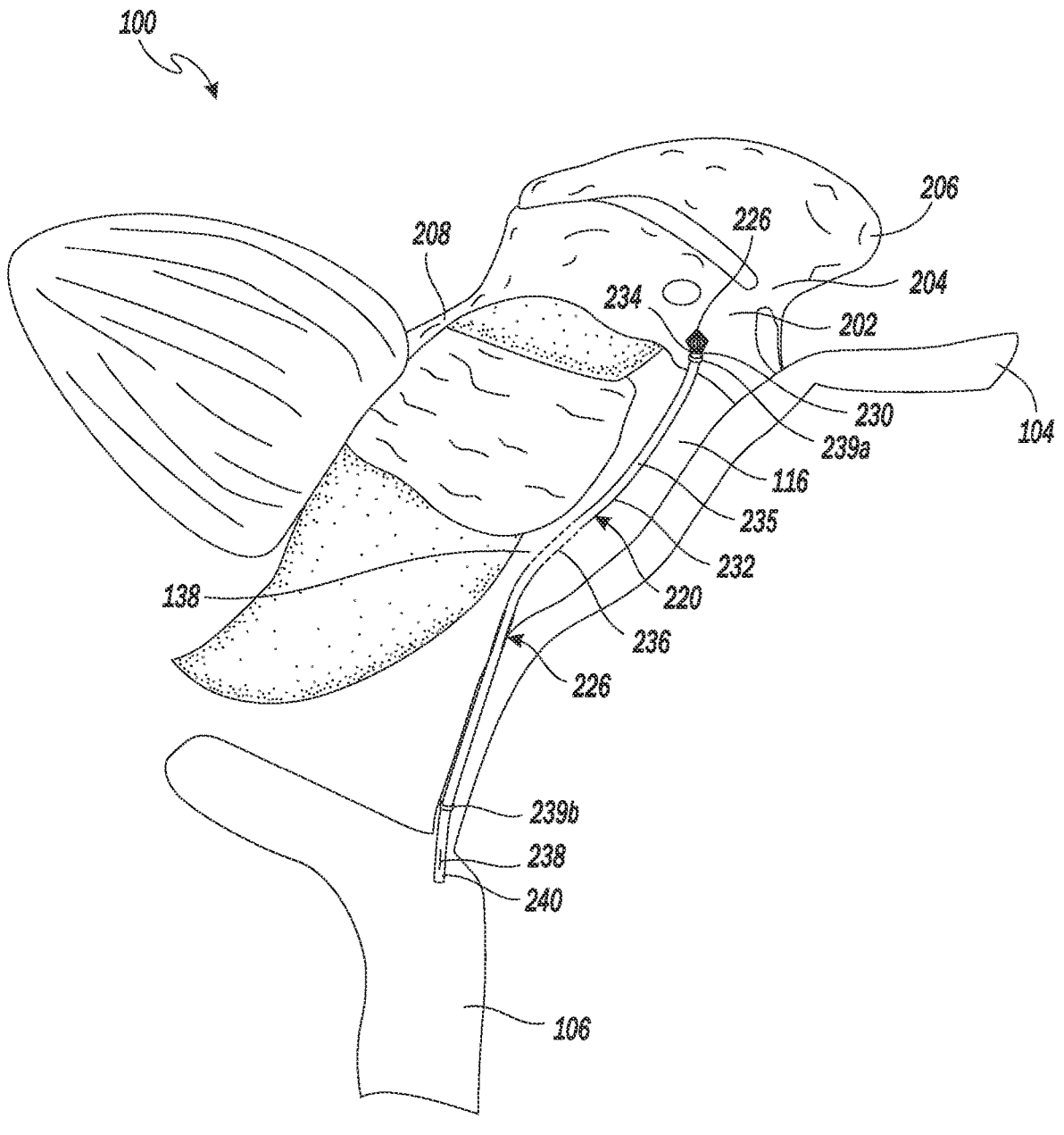
FIG. 23 illustrates an intracranial intervention system and method similar to the system of FIGS. 19-22, in which the catheter has body intake openings to drain CSF from the first intracranial subarachnoid space.

As illustrated in FIG. 23, in some embodiments, the shunt 220 is deployed within the third ventricle 202 and extends through the CP angle cistern 138 of the CSF-filled subarachnoid space 116 such that the body intake openings 236 of the shunt 220 are positioned within the CP angle cistern 138 and function as cisternal drainage holes. Thus, the cisternal drainage holes 236 can permit communication between the shunt lumen 235 and the CSF-filled subarachnoid space 116, such that in-flow and out-flow of fluid is permitted in both the CSF-filled subarachnoid space 116 as well as the third ventricle 202, while out-flow remains possible at the one-way valve 238 located proximate the patient's jugular vein 106 or elsewhere in the patient's venous system. In this manner, obstructive hydrocephalus can be treated by the shunt 220 by permitting fluid from the third ventricle 202 to communicate with the CSF-filled subarachnoid space 116, while continuing to treat communicating hydrocephalus by permitting fluid from the CSF-filled subarachnoid space 116 to communicate with the internal jugular vein 106.

Figure 24:
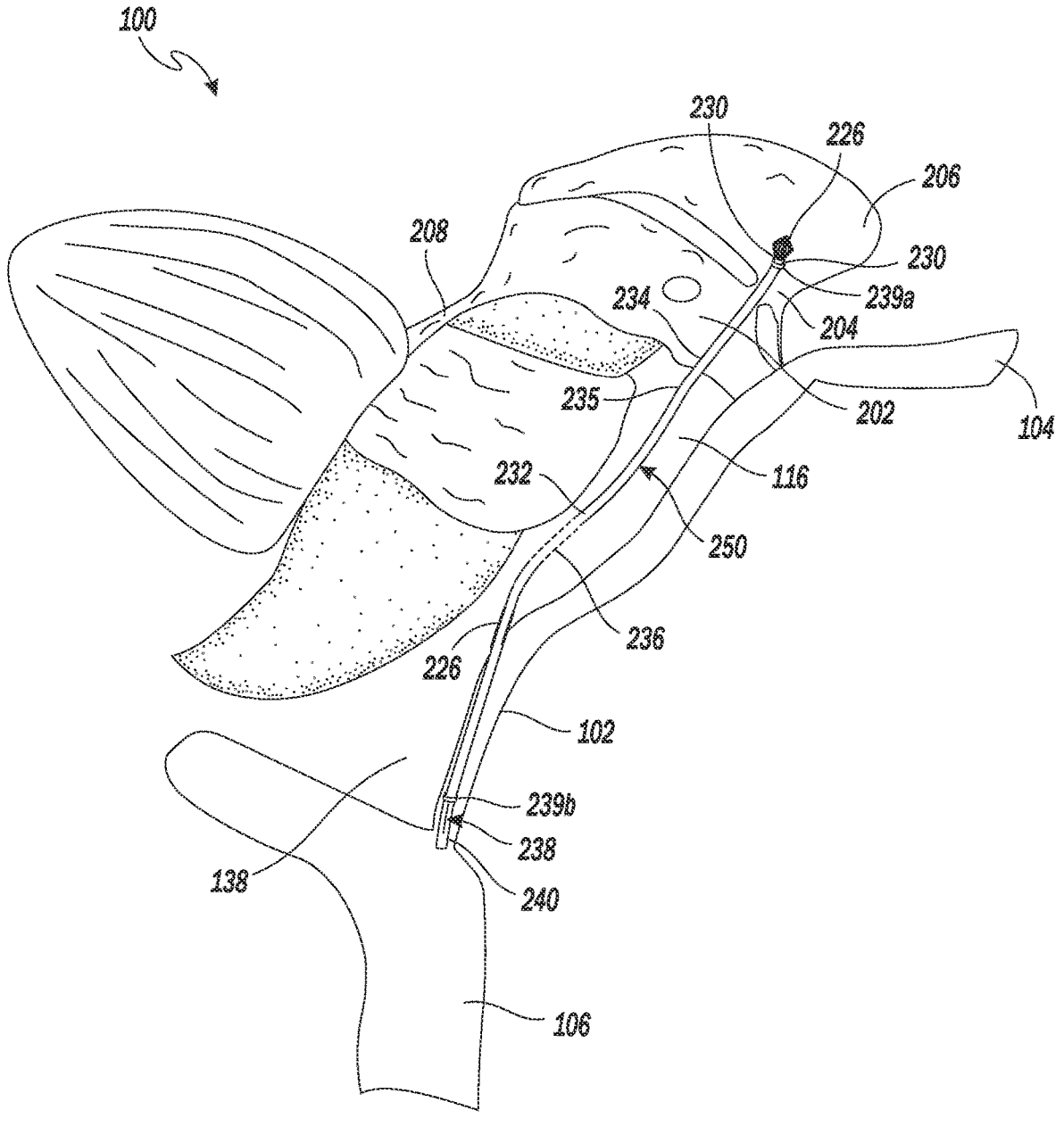
FIG. 24 illustrates an intracranial intervention system and method similar to FIGS. 19-23, in which the shunt extends beyond the third ventricle, through the foramen of Monro, and into a lateral ventricle.

FIG. 24 illustrates an embodiment in which a shunt 250 is configured to extend beyond the third ventricle 202, through the foramen of Monro 204, and into the patient's lateral ventricle 206. The shunt 220 in FIG. 24 is slightly longer than the shunt 250, but otherwise may be the same or similar to the shunt 220, as described herein. The method of deploying the shunt 250 is similar to the method of deploying the shunt 220, except that, after piercing the floor of the third ventricle 202 in any of the manners described above, the physician continues navigation through the ISAS pushing the seeking wire 212 (and/or guide catheter 222) through the third ventricle 202 until it makes contact with the foramen of Monro 204, and extends the seeking wire 212 through the foramen of Monro 204 into the lateral ventricle 206, with the catheter 222 following the path of the seeker wire 212 thereafter. The distal anchoring mechanism 226 deployed to secure the distal portion 230 of the shunt 220 in place within the lateral ventricle 206 after the clinician has navigated the shunt 220 to the shunt delivery site. Once deployed, the distal intake openings of the shunt 220 proximate to the distal anchoring mechanism 226 are located in the lateral ventricle 206, and permit fluid communication between the lateral ventricle 206 and the patient's internal jugular vein 106, via the shunt lumen 235 that extends through the foramen of Monro 204, the third ventricle 202, the CSF-filled subarachnoid space 116, and the IPS 102 or CS 104.

In some embodiments, the shunt 250 that permits fluid communication between the lateral ventricle 206 and the patient's jugular vein 106, as illustrated in FIG. 24, can optionally include body intake openings 236 (i.e., cisternal drainage holes 236) located along the main body portion 232 of the shunt 250 which is disposed within the CSF-filled subarachnoid space 116. In this way, the shunt 250 can permit treatment of obstructive hydrocephalus and/or can provide for equalization of pressure between the lateral ventricle 206 and the CSF-filled subarachnoid space 116.

Figure 25:
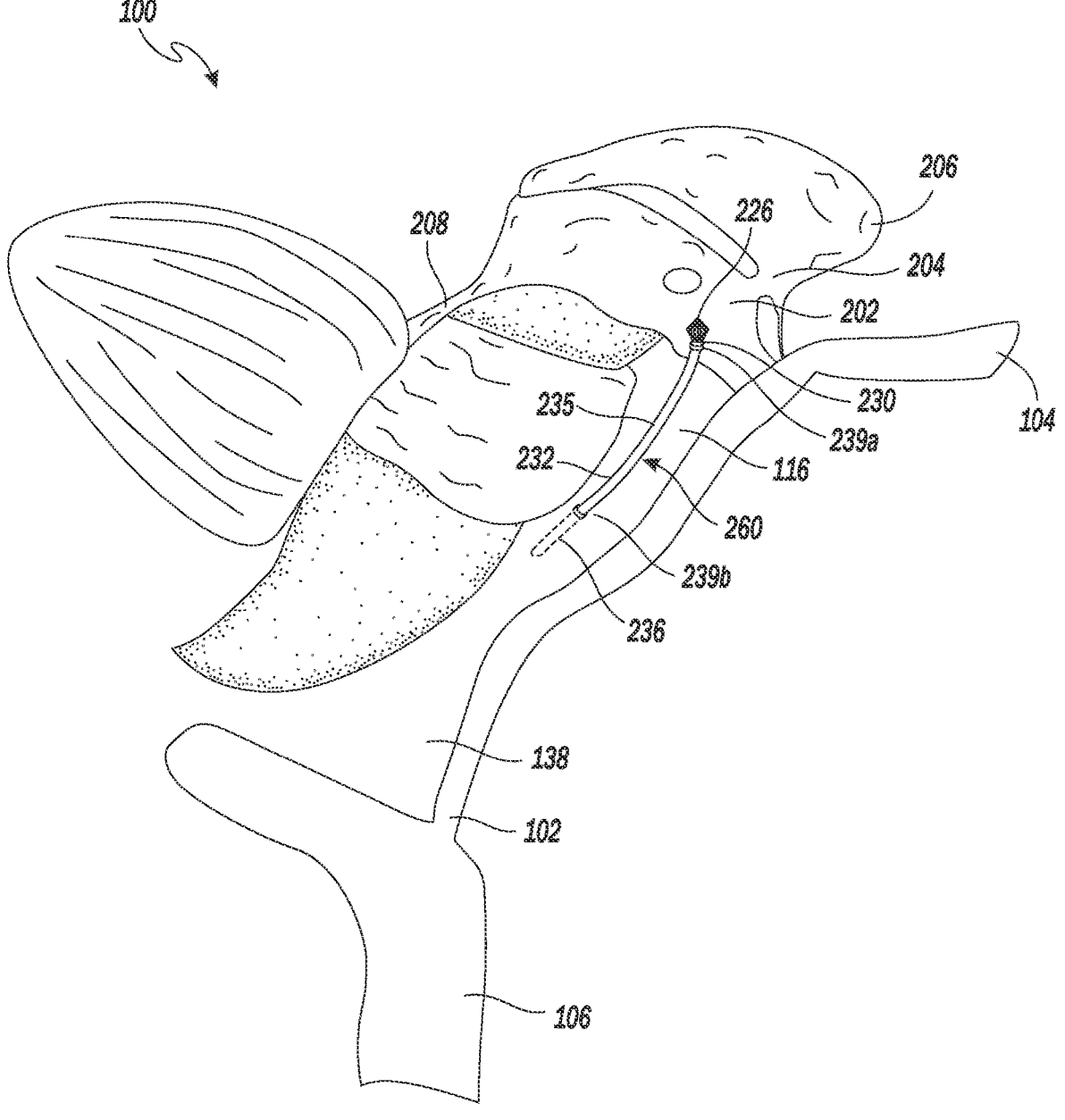
FIGS. 25 and 26 illustrate intracranial interventions system and methods for treating obstructive hydrocephalus by deploying the shunt to permit fluid communication between a patient's ventricles and the CSF-filled subarachnoid space.
Figure 26:
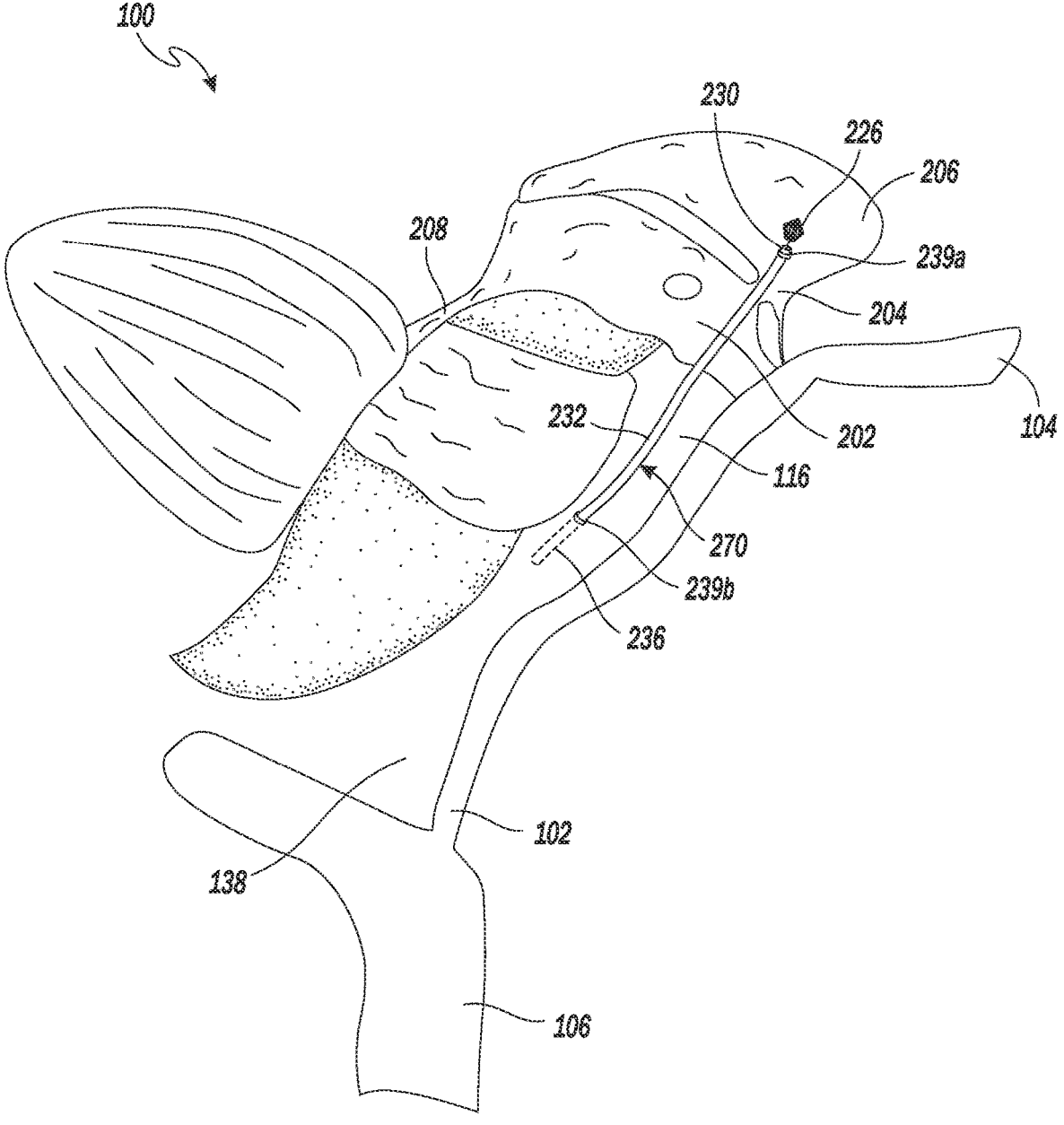

FIGS. 25 and 26 illustrate embodiments of shunts 260, 270, respectively, for treating obstructive hydrocephalus by deploying a shunt that permits communication between a patient's ventricles (e.g., third ventricle 202 and lateral ventricle 206) and the CSF-filled subarachnoid space 116. The shunts 260, 270 are similar to the shunt 220, except that the shunts 260, 270 are shorter and when deployed do not extend proximally to the venous system, such as the jugular vein 106, as with the shunt 220. Accordingly, obstructive hydrocephalus can be treated with the shunts 250, 260 without requiring fluid communication between a patient's ventricles and the patient's venous system, e.g., the internal jugular vein 106 or the like. Rather, in some embodiments, obstructive hydrocephalus can be treated with the shunts 250, 260 by permitting fluid communication between a patient's ventricles and the CSF-filled subarachnoid space 116, without requiring further drainage or communication to the patient's venous system, e.g., the internal jugular vein 106 or the like.

A clinician can deploy the shunts 260, 270 by way of, e.g., advancing a seeker wire 212 and catheter 222 through a patient's venous system, into the IPS 102 or CS 104, piercing through the IPS wall 114 into the CSF-filled subarachnoid space 116, piercing through the floor of the third ventricle 202, in substantially the same manner as described above for the method of deploying the shunt 220. In some embodiments, the clinician can further advance the seeker wire 212 and/or catheter 222 through the foramen of Monro 204 and into the lateral ventricle 206.

Once the distal portion 230 of the shunt 260, 270 is delivered to the patient's ventricle (e.g., the third ventricle 202, the lateral ventricle 206, or the like) and secured by a distal anchoring mechanism 226, the catheter 222 and related hardware can be removed from the patient's head 100 by the clinician. Remaining after removal of the delivery hardware is a shunt 260, 270 with its distal portion 230 disposed in the patient's ventricle and its proximal end disposed in the patient's CSF-filled subarachnoid space 116, permitting fluid communication between the patient's ventricle and the CSF-filled subarachnoid space 116. As shown in FIG. 25, in some embodiments, the distal portion 230 of the shunt 260 can be located in a patient's third ventricle 202, while the proximal portion 230 is located in the patient's CSF-filled subarachnoid space 116 (e.g., CP angle cistern 138). As shown in FIG. 26, in other embodiments, the distal portion 230 of the shunt 270 is located in a patient's lateral ventricle 206, while the shunt lumen 235 extends through brain tissue, e.g., the foramen of Monro 204, the third ventricle 202, and the like, and the proximal end is located in the patient's CSF-filled subarachnoid space 116 (e.g., CP angle cistern 138).

In the embodiments illustrated in FIGS. 25 and 26, there is no fluid communication between the CSF-filled subarachnoid space 116 (or the patient's ventricles) and the IPS 102, CS 104, or the patient's venous system via shunt 260, 270. Once the catheter 222*r* and other associated delivery hardware is removed from the patient's head 100, the opening formed in the IPS wall 114 closes to restrict any fluid communication between the CSF-filled subarachnoid space 116 and the IPS 102, CS 104, or venous system. In some embodiments, the opening clots and closes on its own, quickly enough to avoid substantial unintended fluid communication between the two regions. In some embodiments, it can be possible to embolize the opening and optionally the region adjacent the opening, in order to prevent unintended fluid communication between the CSF-filled subarachnoid space 116 and the IPS 102, CS 104, or venous system.

The intracranial intervention system 201 may also be utilized for endovascular navigation and access of an ISAS (including a second ISAS) for administering a therapy in the ISAS. The ISAS is accessed using the intracranial intervention system 201, as described herein. Then, the therapy is administered in the ISAS via the catheter 222. For example, administering a therapy may comprise aspirating blood or other tissue from the ISAS through the catheter 222, or removing a tumor located in the parenchyma. A method of therapy may also include administering a therapeutic agent into the parenchyma. For instance, the method of using the intracranial intervention system 201 may include dissecting into a location in the brain parenchyma with the seeker wire 224. Then, the catheter 222 is advanced into the dissection in the parenchyma and a therapeutic agent is administered via the catheter 222 into the parenchyma. The therapeutic agent may comprise a composition intended to have a therapeutic effective on all or a portion(s) of a central nervous system of the patient. For example, the therapeutic agent may comprise one or more of the following: anti-sense RNA; anti-sense oligonucleotides; anti-bodies; antibiotics; anti-vasospasm agents; biosimilars; chemotherapy agents; GABA receptor agonists; an agent for treatment of neuro-degenerative diseases including Alzheimer's disease Parkinson's disease and Huntington's disease; and tissue plasminogen activator. In another method, the therapy may include administering laser interstitial therapy.

There also exists a need in the art for a versatile set of tools that expand upon currently available transvenous approaches to low-profile tissue or tumor biopsy and resections, including without limitation, navigation through intracranial space, and biopsy and resections of brain tissue. Currently available catheter systems for tumor biopsy and resection suffer from a number of shortcomings, including, e.g., suboptimal ability to navigate to the site of a tumor, and difficulty in maneuvering during that navigation. Minimally-invasive surgery techniques (and tools for carrying out those techniques) are preferred because they minimize risk of damage to important bodily systems and can lead to decreased recovery time for a patient following surgery. Current surgical tools for access to and resection of tumors can include grabbers, morselizers, or can include cutting through or around a target area, none of which are suitable for traveling through or access to compact areas of the body. The currently-available surgical tools also do not adequately retrieve or resect the tumors or other tissues to which they are directed, leaving undesired portions behind or requiring the use of more invasive surgical techniques to adequately address the issue ailing the patient.

In some aspects, the systems and methods described with respect to FIGS. 27-50 relate to providing a set of endovascular tools and catheters that enable navigation into the brain parenchyma (e.g., from the ISAS's) for the retrieval of tissue for biopsy and compression. The systems and methods described herein can result in better purchase and stability during tumor resection. For example, the systems and methods described herein can be used for biopsy and retrieval of a tumor or tissue from various regions of the body, including, e.g., within the brain parenchyma. The systems and methods described herein can more generally be used to navigate through the venous system to access tissue located proximate any suitable vein including tissue within the ISAS's. Accordingly, the tools, systems and methods described with respect to FIGS. 27-50 may be used in conjunction with the intracranial intervention system 201 and methods of using the system 201 described herein.

In some aspects, the systems and methods described herein are endovascular access systems and methods for burrowing into tumor tissue which can be used for endovascular access to tumor tissue or selected areas in the brain parenchyma. A catheter system, such as the intracranial intervention system 201, can be navigated through a patient's vasculature to a target location (e.g., as described below with respect to FIGS. 27-33, in order to burrow into or through tumor tissue).

Figure 27:
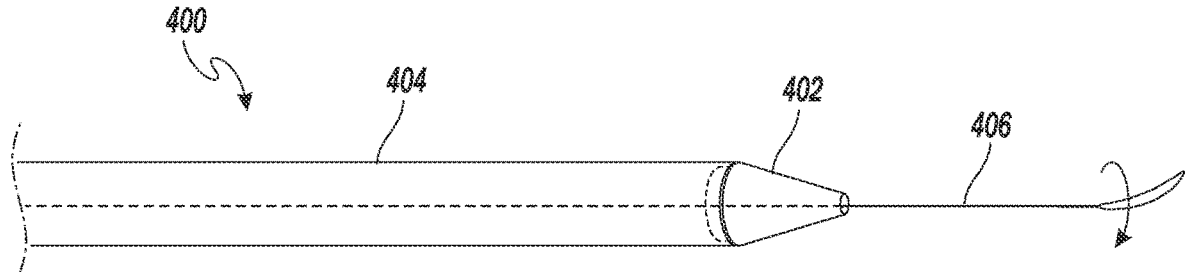
FIG. 27 is a side, perspective view of an endovascular access system having a removable nose-cone insert, according to one example.

FIG. 27 depicts one embodiment of an endovascular access system 400 that includes a removable nose-cone insert 402 attached to a microcatheter 404, all of which can be navigated through a patient's vasculature and/or through tissue to a target location over a guidewire 406. For instance, the catheter 404 may be catheter 222 within the intracranial interventions system 201. The removable nose cone insert 402 permits navigation through tissue of varying density and viscoelasticity. During surgery, the physician can manipulate the guidewire 406 through a patient's tissue toward a target location. The catheter 404 can be advanced over the guidewire 406 toward the target location. Such advancement is facilitated by the removable nose-cone insert 402, which can temporarily displace tissue in the way of the catheter 404, in effect burrowing and advancing the catheter 404 through the patient until the tissue of interest is reached. In other words, the removable nose-cone insert 402 can act as a sort of wedge to create a sufficient opening in intermediate tissue such that the diameter of the catheter can be advanced through intermediate tissue to a target location. In some embodiments, the nose-cone insert 404 can be optionally removed backward out through the catheter 404 (e.g., by pulling the removable nose-cone insert 402 out by a wire or smaller-diameter catheter attached to the removable nose-cone insert 404), once the target tissue is reached such that other tools can be inserted through the catheter 404 to access the target tissue to be worked.

In some embodiments, the removable nose-cone insert 402 can be an active nose cone, which can include elastic elements that permit the nose cone 402 to expand when it is not disposed within a catheter 404. The removable nose-cone insert 402 can include multiple stent-like elements that open and close (e.g., automatically or by a physician manipulating a connected wire) as the device is being burrowed through intermediate tissue toward target tissue. Various imaging or sensor methods can be implemented such that the physician can follow the progress of the wire 406 and catheter 404 through intermediate tissue and ensure that the device is being appropriately advanced toward target tissue, for example through the use of radiopaque markers or x-ray.

Figure 28:
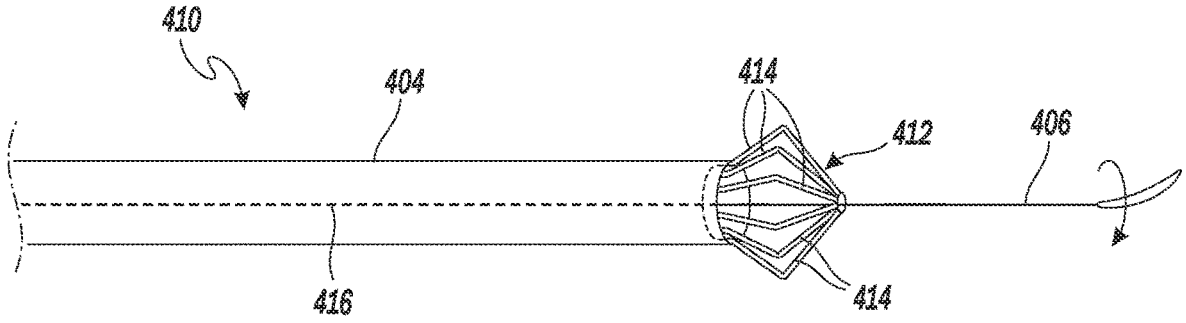
FIG. 28 is a side, perspective view of an endovascular access system having an expandable nose-cone insert, according to one example.

FIG. 28 depicts an embodiment of an endovascular access system 410 that includes an expandable nose-cone insert 412 connected to or formed proximate to a microcatheter 404. The expandable nose-cone insert 412 can include stent-like elements 414 that expand upon being unsheathed from the catheter 404. The set of elements or struts 414 that make up the expandable nose-cone insert 412 can be expanded or retracted by a physician as the catheter 404 is advanced over the wire 406 toward target tissue. The set of elements or struts 414 can be expanded or retracted by a physician pushing or pulling on an actuation wire 416 connected to the expandable nose-cone insert 412 that extends through the catheter 404 and out of the patient's body to where the physician is working.

In some embodiments, the set of elements or struts 414 making up the expandable nose-cone insert 412 can be covered by a membrane (not shown). The membrane can permit transient expansion to enable burrowing deeper into tissue, e.g., by preventing intermediate tissue from becoming caught in or damaged by the set of elements or struts 414 making up the expandable nose-cone insert 412. In some embodiments, the expandable nose-cone insert 412 can be a fluid-filled balloon, instead of a set of multiple struts, which can have the same effect of pushing intermediate tissue out of the way to permit movement of the catheter 404 through the body. The expandable nose-cone insert 412 can also be used to anchor the catheter 404 in place once the device 410 has been advanced through the body and proximate to the target tissue.

Figure 29:
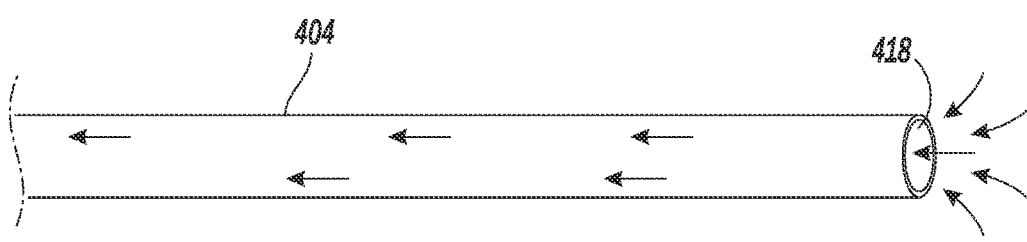
FIG. 29 illustrates a method in which the removable nose-cone inserts and/or expandable nose-cone insert of FIGS. 27 and 28 may be retracted such that the catheter may be used as a tumor suction port.

In some embodiments, the expandable nose-cone insert 410 or the retractable nose-cone insert 400 can be withdrawn backward through and out of the catheter 404, as depicted in FIG. 29. Once withdrawn, the end of the catheter 404 proximate to the target tissue can serve as a tumor suction port 418 for resection of a tumor.

Figure 30:
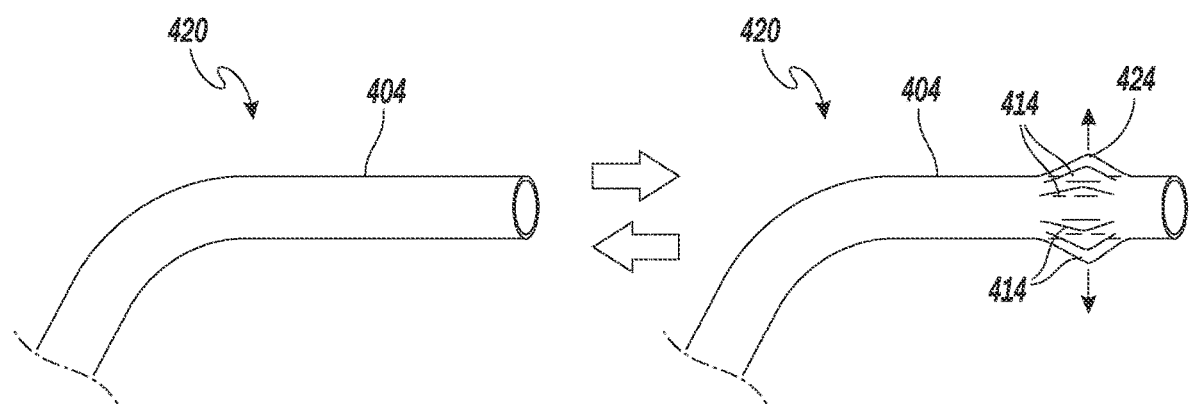
FIGS. 30 and 31 are side, perspective views of endovascular access systems in which the expandable/retractable element is located at a distance proximal to the distal end of the catheter.
Figure 31:
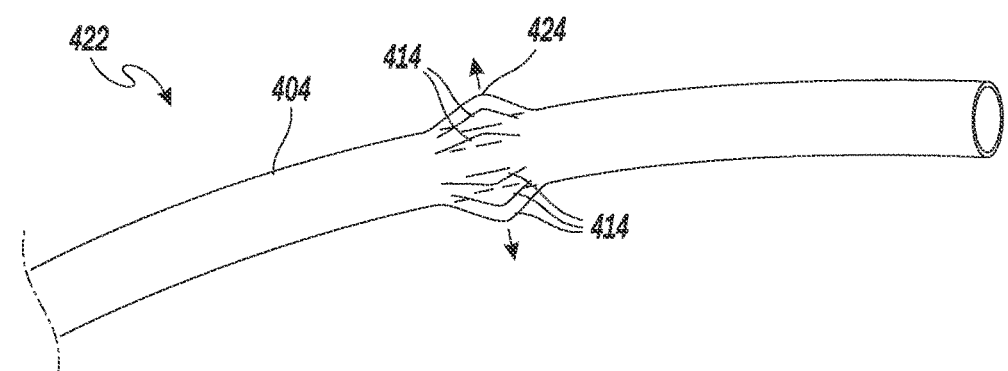

FIGS. 30 and 31 depict an embodiment of respective endovascular access systems 420 and 422 wherein an expandable/retractable element 424 can be located at a distance from the distal end of the catheter 404. The expandable/retractable element 424 can be built and can function similarly to the retractable nose-cone 402 or the expandable nose-cone 412 as described above with respect to FIGS. 27-29.

As depicted in FIG. 30, the expandable/retractable element 424 can be retained in the retracted state, such that the sides of the catheter 404 are substantially smooth and free of protrusions that would impede the catheter's 404 advancement, while the catheter 404 is advanced through intermediate tissue and/or ISAS's of a patient's body. The element 424 can be retracted by actuation of an actuation wire or other suitable control by a physician from outside the patient's body. Once the target tissue is reached, the physician can actuate the expandable/retractable element 424 to cause, e.g., multiple elements or struts 414 to 'pop out' from the exterior surface of the catheter 404. The expandable/retractable element 424 can extend from the exterior surface of the catheter 404 a sufficient distance that the expandable/retractable element 424 engages with a patient's tissue to hold the catheter 404 in place without it slipping further inward, out of, or laterally within the patient's body, to permit the physician to perform the desired work on target tissue. In this manner, forces experienced by or applied to the tip of the catheter 404 proximate the target tissue, e.g., forces from manipulating or resecting a tumor, can be overcome and the catheter 404 can be held stably in position.

In some embodiments, e.g., as depicted in FIG. 31, the expandable/retractable element 424 can be located a further distance away from the distal tip of the catheter 404 such that it can engage with intermediate tissue that is a distance away from the target tissue. For example, the expandable/retractable element 424 can be located at a position along the catheter 404 that coincides with a position within a patient's body that has sufficiently sturdy tissue structure to hold the catheter 404 in place, including without causing damage to the tissue being engaged by the expandable/retractable element. In some embodiments, multiple expandable/retractable elements 424 can be deployed at various positions along the length of the catheter 404, for example to increase the probability that the catheter 404 will be held in place and will not be inadvertently jostled during operation. Implementing multiple expandable/retractable elements 424 can also permit individual expandable/retractable elements 424 to be deployed at various times during an operation, e.g., to ensure that an expandable/retractable element 424 is located in the correct position (e.g., a position at which it can gain sufficient purchase with tissue without damaging it) for access to a particular target location.

Figure 32:
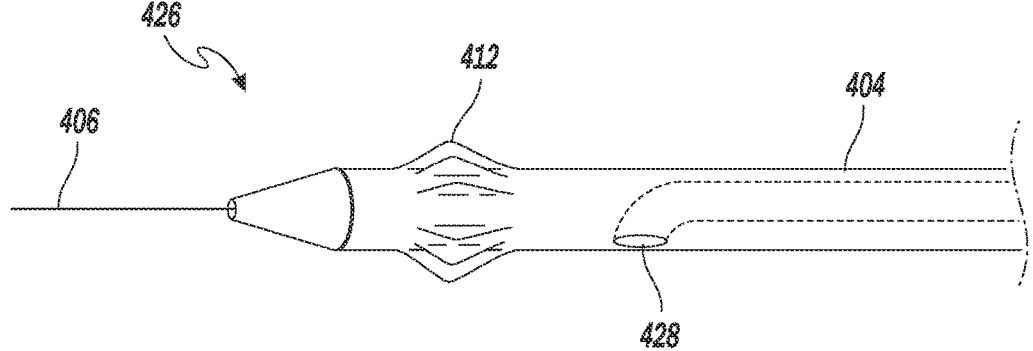

FIGS. 32 and 33A-B depict an embodiment of an endovascular access system 426 including a working side-port 428, an expandable tip 412, and a guidewire 406. As described above with respect to the removable nose-cone 402, expandable nose-cone 406, and the expandable/retractable elements 424 shown in FIGS. 27-31, an expandable tip can be attached to or proximate to, or included as part of the catheter 404 to facilitate advancement of the catheter 404 along the guidewire 406 through a patient's vasculature or tissue. FIG. 33A depicts the endovascular access system 426 in the unexpanded state, i.e., when the expandable tip 412 is retracted such that the catheter 404 can be advanced over the wire 406 through a patient, and FIG. 33B depicts the expanded state, i.e., when the expandable tip 412 is expanded and the catheter 404 is held in place while the physician works on the patient. In some embodiments, the expandable tip 412 can be a balloon that performs the same retention functions as described with respect to the described expandable/retractable elements 414 and the like. The use of an expandable tip 412 can permit catheters 404 with larger diameters than previously possible in prior art systems and methods to be advanced to target locations not previously possible in those prior art methods. For example, repeated actuation of the expandable tip 412 can move tissues, e.g., web-like structures, out of the way of the advancing catheter 404, whereas in prior art systems the catheter itself could be stopped from advancing by those tissues.

The endovascular access system 426 depicted in FIGS. 32-33 can include a working sideport 428 disposed in the side of the catheter 404. When working on a patient, e.g., resecting a tumor, or otherwise accessing tissue of interest, the catheter 404 can be advanced over the guidewire 406 such that the working side-port 428 can be proximate to the tumor or tissue of interest. The working side-port 428 thus enables tools to be able to access regions of tissue laterally, rather than through the end of the catheter 404, which can permit for less invasive surgery and transvenous/endovascular access to regions of the body that were previously accessible only through invasive external, open, surgery.

FIGS. 34A-36B depict various endovascular systems and methods for resecting and removing tumor tissue using a variable inflow zone catheter 430. A variable inflow zone catheter 430 can be used to break and macerate tumor tissue such that it can be suctioned through a flexible catheter 404. As shown in FIG. 34A-B, the variable inflow zone catheter 430 has a variable inflow zone 432 at its distal end (the end located proximate a target site, e.g., tumor tissue) that can expand to a larger cross section, in order to facilitate efficient removal of tumor tissue. In some embodiments, the variable nozzle 432 of the variable inflow zone catheter 430 can be made of a mesh or a hermetic membrane seal, to permit it to expand when disposed proximate a target location. FIG. 34A shows the variable inflow zone 432 in a retracted state and FIG. 34B shows the variable inflow zone 432 in an expanded state.

Figure 35:
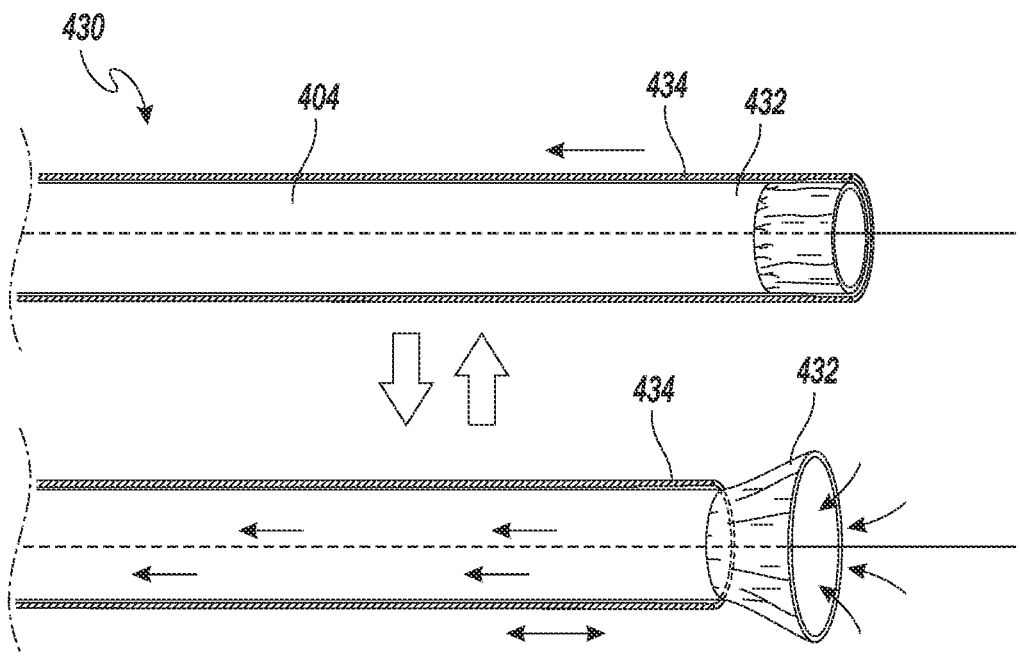

As depicted in FIG. 35, in some embodiments the variable nozzle 432 can be retained in the retracted state by means of a sheath 434 that is disposed over the variable inflow zone catheter 430 while it is being navigated to a target location. In some embodiments, the sheath 434 can be a catheter of larger diameter than the variable inflow zone catheter 430. The sheath's diameter should be sufficiently small (e.g., smaller than the variable nozzle 432 in the expanded state) such that the device can be easily navigated through a patient to a target location while realizing the benefits of a small profile. Upon withdrawal of the sheath 434, the variable nozzle 432 can be permitted to expand to the expanded state. In some embodiments, the variable nozzle 432 can be made up of a number of Nitinol (or the like) tines connected by a membrane or hermetic mesh, which are exposed and expand upon withdrawal or partial withdrawal of the sheath. In some embodiments, the outer sheath 432 can be a guide catheter.

Figure 36A:
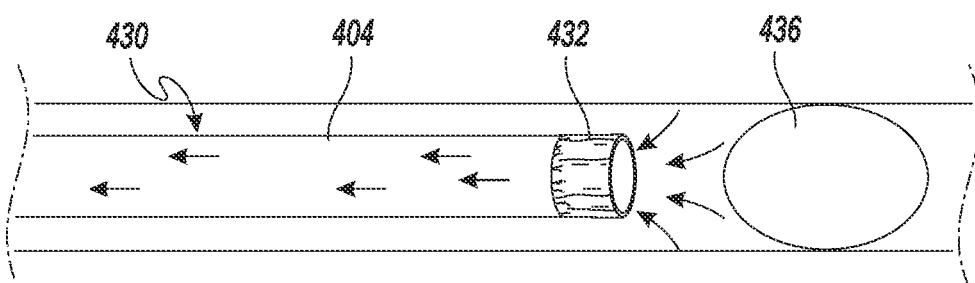
Figure 36B:
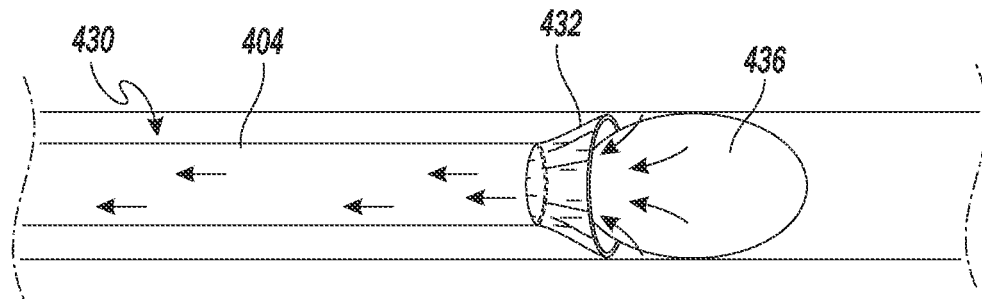

FIGS. 36A-B depict the variable inflow zone catheter 430 coming into contact with a tumor 436. Once the variable inflow zone catheter 430 is navigated to the desired target location proximate or adjacent to a target location, the variable nozzle 432 can be permitted to expand to the expanded state. The variable nozzle 432 has a larger cross-sectional area in the expanded state, which can permit increased suction to resect or remove all or parts of the tumor 436 that is adjacent to the end of the variable inflow zone catheter 430. In some embodiments, the variable inflow zone catheter 430 can be used to enable efficient suction by permitting the variable nozzle 432 to expand to a sufficient cross-sectional area to maintain a tight seal on a target tumor 436.

Figure 37:
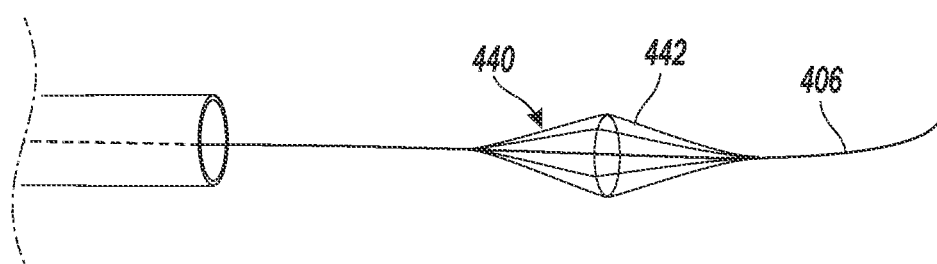
FIGS. 37-40 are side, perspective views of several examples of tumor scoops for tumor retrieval and/or resection, which may also be used with the other endovascular access systems.
Figure 38:
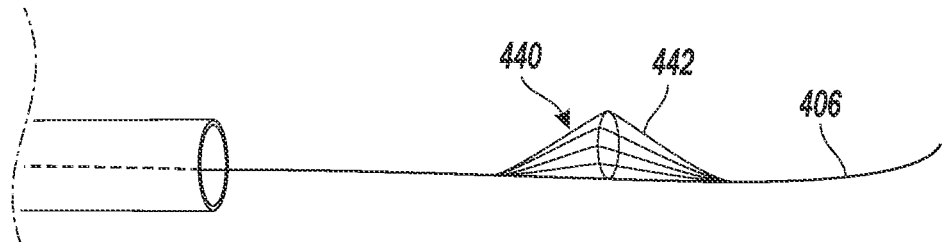

FIGS. 37-40 depict tumor scoop embodiments that can be used for tumor retrieval and/or resection. Tumor scoops can be deployed in concert with suction or other systems and methods described herein to enable more efficient and effective retrieval of tumors, by grabbing on to all or a portion of the target and dragging or guiding it back toward a catheter for removal. FIG. 37 depicts a wire-based scoop 440 that is centered along a guidewire 406, while FIG. 38 depicts a similar embodiment wherein the wire-based scoop 440 is disposed off-center from the guidewire 406. In either embodiment, a membrane can be attached to a multi-strut self-expanding structure 442 that can capture all or a portion of a target tumor. For example, the guidewire 406 can be advanced to, past, or into a tumor, and can subsequently be withdrawn such that the scoop captures all or part of a tumor and brings it toward a working catheter, through which suction can optionally be provided.

The various embodiments of tumor scoop 440 can facilitate advancement of the wire 406 and collapsed scoop 440 into and through a tumor with a low profile and then expanding and retrieving tissue into a catheter 404, through which suction can also optionally be applied.

Figure 39:
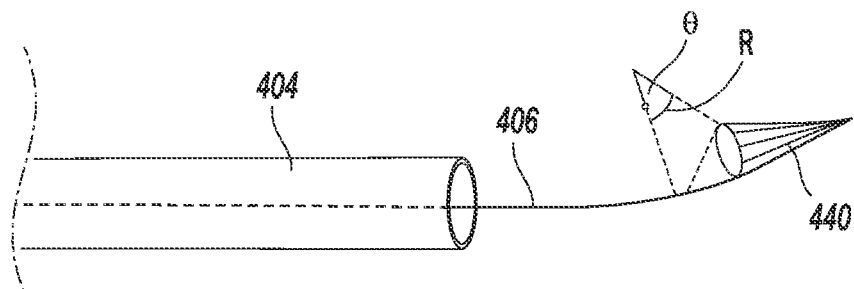
Figure 40:
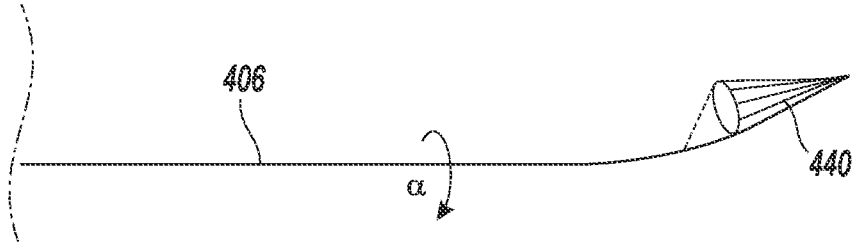

FIGS. 39-40 depict angled embodiments of a tumor scoop 440, which can advance through a microcatheter 404. In some embodiments, the endovascular scoop 440 can be configured to be employed in different anatomical needs, wherein, e.g., the length or width of the scoop can be varied, or the angle of the scoop 440 with respect to the guidewire 406 and/or catheter 404 can be varied to reach a targeted anatomical region. In some embodiments, the wire 406 and scoop 440 can be fashioned using Nitinol shape memory material to allow the scoop 440 to deploy at an angle theta and radius R with respect to the guidewire 406 and/or catheter 404, substantially as depicted in FIGS. 39-40. The scoop 440 and wire 406 can also be configured to be rotatable through an angle alpha before or during retrieval of a target tissue.

Figure 41:
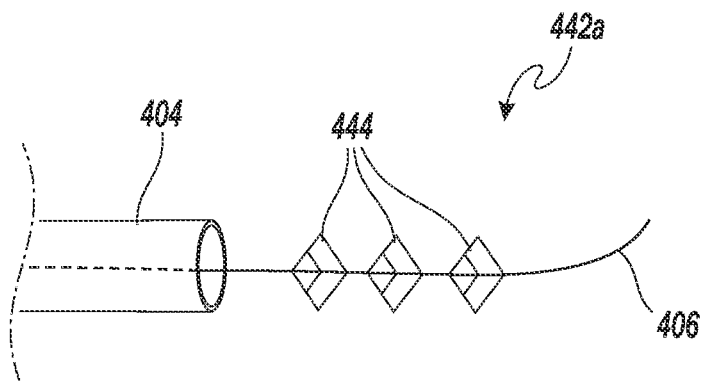
FIGS. 41-46 are side, perspective views of several examples of endovascular macerator devices for tumor resection and retrieval, which may also be used with the other endovascular access systems.
Figure 42:
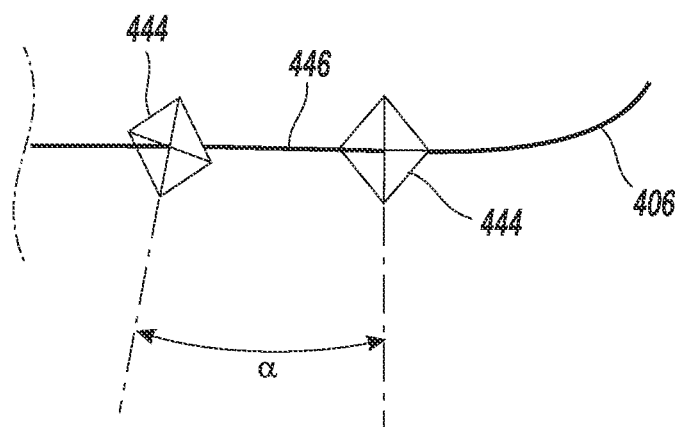

FIGS. 41-46 depict various embodiments of an endovascular macerator device 442 that can be used for tumor resection and retrieval. As depicted in FIG. 41, malecots 444 can be provided along a guidewire 406 to create an endovascular macerator 442a capable of breaking up target tissue. In some embodiments, the wire 446 and catheter 404 can be advanced through tissue (including optionally with the use of any of the devices or methods described herein to facilitate navigation through a patient's vasculature or tissue systems) to a target, e.g., a tumor or other tissue. Once in place, the physician can push the portion of the wire 446 that includes one or more malecots 444 into the target to break up the tissue, which upon pulling the wire back and pull the broken-up tissue back into the catheter. In some embodiments, suction is optionally provided through the catheter 404 to capture the tissue that is macerated upon operation of the malecot wire 446. The wire can be pushed and pulled to cause the malecots 444 to perform a sawing motion and function on the target tissue. As depicted in FIG. 42, the various malecots 444 can be mounted at differing angles (denoted by alpha) from one another, to present a variable cross-section during deployment and withdrawal. The use of differing angles can facilitate better maceration of the target tissue than where all malecots 444 are mounted in the same angular orientation, an orientation which can itself be more beneficial for more targeted, accurate, maceration of target tissue where such a function is required.

Figure 43:
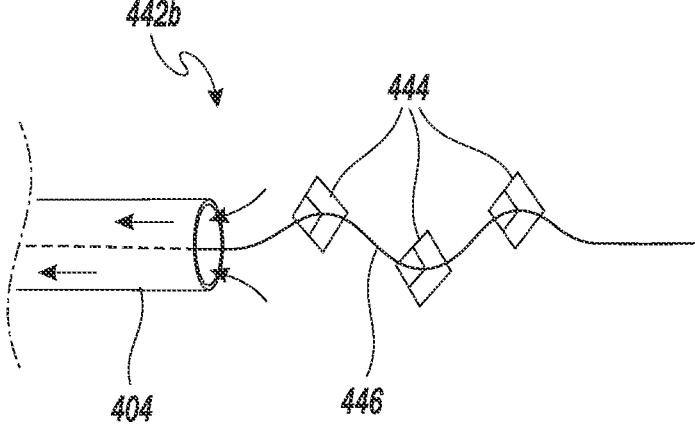

FIG. 43 illustrates another embodiment of an endovascular macerator 442b. The wire 406 upon which the malecots 444 are mounted is curved to present the malecots 444 out of alignment from one another when being pushed into or toward a tumor or tissue. In some embodiments, the curvature of the wire 446 can follow a sinusoidal curve, while in other embodiments the wire 446 curvature can follow a random pattern. In some embodiments, the wire 446 can be curved only along one dimension, e.g., the y-dimension or the z-dimension where the x-dimension is defined by an axis extending straight from the end of the catheter. In some embodiments, the wire 446 can be curved along both the y-dimension and the z-dimension, which can further improve the reach of the maceration action beyond curvature in only one of the dimensions.

Figure 44:
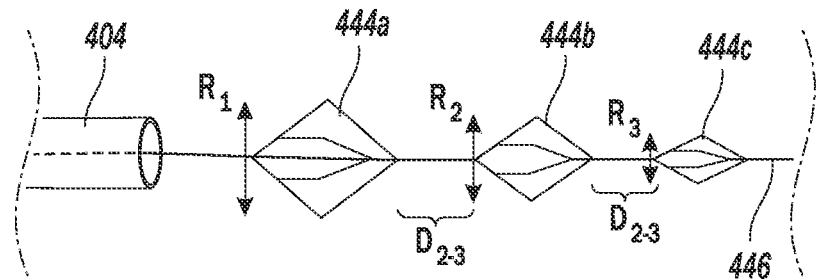
Figure 45:
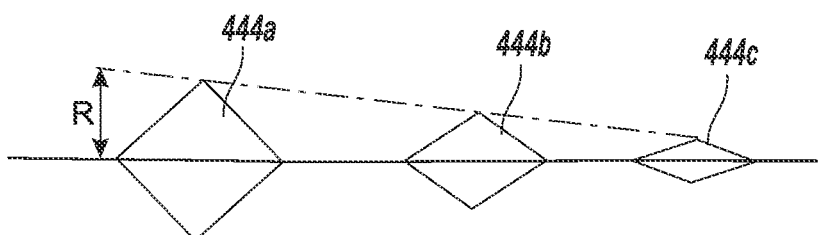

In some embodiments, including the endovascular macerator 442c, as shown in FIGS. 44 and 45, the individual malecots 444 can have varying sizes along the length of the wire 446. As depicted in FIGS. 44 and 45, malecots 444a, 444b, and 44c have decreasing radii (defined by the distance between the two points of the malecot 444 most distant from the wire 446) from the end closest to the catheter 404 to the free end of the guidewire 446. In this manner, the size profile of the malecots 444 can be defined so as to enable progressive conical channel formation in tissue and/or tumor coring.

Figure 46:
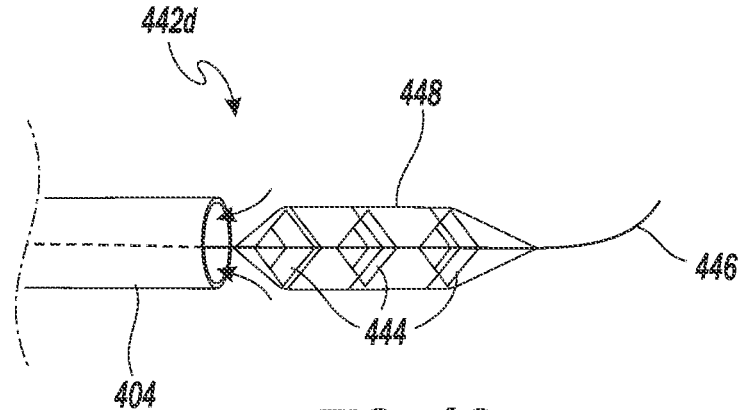

FIG. 46 depicts an embodiment of an endovascular macerator 442d that further includes a stent sheath 448 over the malecots 444, which can be provided as described herein with respect to FIGS. 41-45. A closed-cell stent sheath 448 can enclose and form a contour over the malecots 444 to improve smoothness of delivery of the malecots 444 to a desired location. Embodiments including a stent sheath 448 can be advantageous in situations where the tumor tissue is not malleable.

Figure 47:
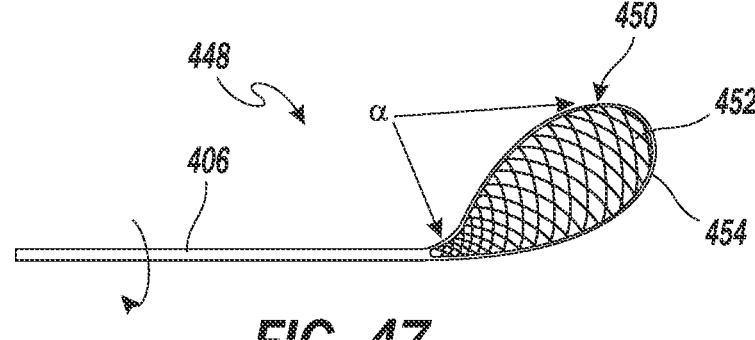
FIGS. 47-48 are side, perspective view of an example of a curette device for tumor or tissue retrieval and/or resection, which may also be used with the other endovascular access systems.
Figure 48:
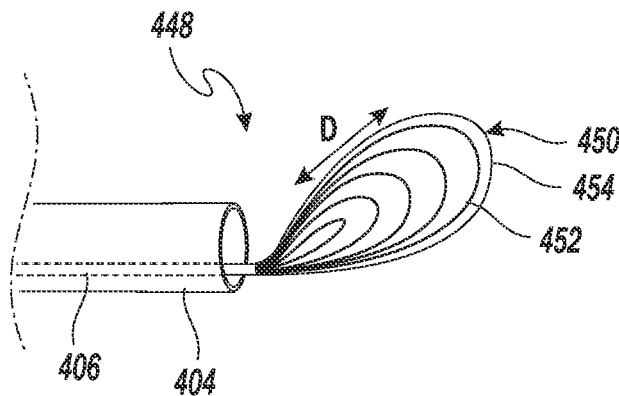

FIGS. 47 and 48 depict an endovascular curette device 448 that can be used for tumor or tissue retrieval and/or resection. A curette-shaped apparatus 450 is provided at the end of a guidewire 406, which can be deployed through a microcatheter 404 at a target location. In some embodiments, including as depicted in FIG. 47, the curette 450 can be formed with a wire substructure 452 covered with a membrane 454 which can capture or hold onto targeted tissue. In some embodiments, the curette 450 can extend from the wire 406 at a predetermined angle alpha (e.g., through the use of Nitinol memory material) and can extend a depth D away from the guidewire 406. As depicted in FIG. 48, the curette 450 can be made of a number of shape memory (e.g., Nitinol or a like material) wires 452 that combine to form the curette shape. In some embodiments, the curette device 450 can be combined and pushed through a rotatable working port, similar to working port 428 which can be rotated by rotating the catheter 404, which can enable directional shaving or scooping of malleable or soft tumors or other target tissue.

Figure 49:
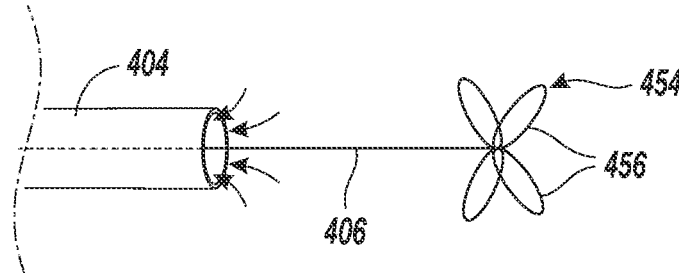
FIG. 49 is a side, perspective view of an example of a petal wire scoop device for tumor or tissue retrieval and/or resection, which may also be used with the other endovascular access systems.

FIG. 49 depicts a petal wire scoop device 454 for retrieval and/or resection of tumors and other tissue. The petal wire scoop 454 can be provided at the end of a guidewire 406. Substantially as described herein, a catheter 404 can be navigated through a patient's vasculature or tissue to a desired target location, and can optionally be secured in place such that the end of the catheter remains in that location. The petal wire scoop 454 can be pushed through the catheter 404 toward the target location, and once the end of the petal wire scoop 454 is pushed free of the catheter 404, multiple membrane-covered or free petal wire loops 456 can deploy outwardly from the wire 404, as shown in FIG. 49. The petal wire loops 456 can be in a collapsed configuration when in the catheter 404. The petal wire loops 456 can be rigid enough to scoop and retrieve tissue, but malleable enough to be permitted to retracted back into the catheter 404 for removal in a controlled fashion. The angle of the various petal wire loops 456 (e.g., 2 loops, 3 loops, 4 loops, 5 loops, 6 loops, or 7 or more loops) can be varied according to the application, to ensure that only the target tissue is impacted and to improve the resection and retrieval capabilities of the device.

Figure 50:
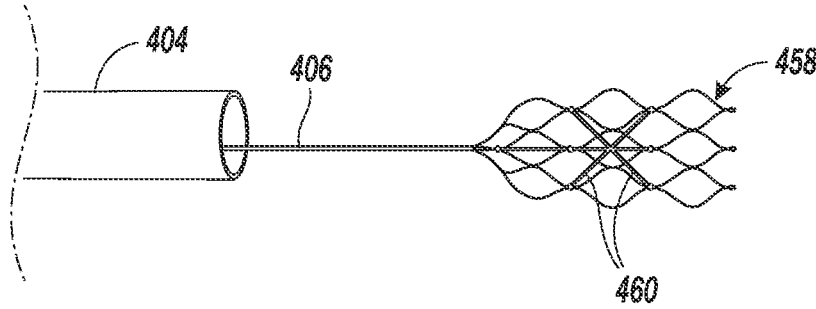
FIG. 50 is a side, perspective view of an example of a stent anchor device for tumor retrieval and/or resection, which may also be used with the other endovascular access systems.

FIG. 50 depicts a stent anchor device 458 that includes internal struts 460 to retrieve or resect all or portions of a tumor. The stent anchor 458 can include one or more internal struts 460 extending across the inner diameter of the stent anchor 458. The stent anchor 458 can be navigated through a catheter 404 in a compressed form until it reaches a target location, e.g., a tumor or other tissue. The stent anchor 458 can then be extended through the end of the catheter 404 can be deployed inside or adjacent to a tumor or other tissue. In the case of a sufficiently soft or malleable tumor, parts of the tumor can extend into the stent anchor 458 when in the expanded, deployed condition, and can catch on the internal struts 460. The internal struts 460 can facilitate dragging or moving the tumor toward a suction catheter 404 for removal, and/or can be formed with sharp edges to break up portions of the tumor or other tissue.

In any of the systems or devices described herein with respect to FIGS. 27-49, segments of the system or devices can be current-carrying, to aid in tumor detachment and coagulation. For example, the outer surfaces of a stent anchor 458 device as described with respect to FIG. 50 can be shielded to protect nerve and vascular structures during navigation and deployment, while the internal struts 460 can be current carrying to coagulate internally-contained tumor tissue when in operation. For another example, the stent sheath 448 described with respect to FIG. 46 can be shielded to protect nerve and vascular structures, while the malecots 444 disposed therein can be current carrying in order to facilitate improved coagulation and tumor detachment functions. As mentioned above, the tools, systems and methods described with respect to FIGS. 27-50 may be used in conjunction with the intracranial intervention system 201 and methods of using the system 201 described herein. For instance, the nose-cone insert 402, expandable nose-cone insert 412, expandable/retractable element 424, endovascular access system 426, variable inflow zone catheter 430, tumor scoops 440, endovascular macerator devices 442, curette devices 448, petal wire scop 454, and stent anchor device 458, may be used in conjunction with, or in place of, the catheter 222 of the intracranial intervention system 201 in order to dissect tissue while advancing the catheter through the intracranial anatomy to a target location (e.g., from an intravascular location to a target deployment site or target therapy intra- or extravascular location), and/or to resect and/or retrieve a tissue sample (e.g., a tumor sample), and/or to image the target location, and/or to perform any other suitable diagnostic or therapeutic procedure.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. A method for performing an endovascular third ventriculostomy, comprising:
    navigating a delivery catheter through a vasculature of a patient until a distal end portion of the delivery catheter is disposed in a dural venous sinus (DVS) of the patient;
    penetrating a wall between the DVS and a cerebrospinal fluid-filled intracranial subarachnoid space (ISAS) of the patient with the distal end portion of the delivery catheter, so that the distal end portion of the delivery catheter is disposed within the ISAS;
    navigating a tool through a lumen of the delivery catheter until a distal end portion of the tool extends out an opening in the distal end portion of the delivery catheter within the ISAS, and toward a cerebrospinal fluid-filled third ventricle:
    navigating the distal end portion of the tool through the ISAS toward a floor of a cerebrospinal fluid-filled third ventricle that separates the ISAS from the third ventricle; and
    penetrating the floor of the third ventricle with the distal end portion of the tool to thereby create an opening in the floor that allows cerebrospinal fluid to flow from the third ventricle into the ISAS.

2. The method of claim 1 wherein the tool comprises a guidewire with an expandable dissector tip on a distal end of the guidewire, and wherein penetrating the floor of the third ventricle with the distal end portion of the tool comprises dissecting a hole through an arachnoid layer separating the third ventricle from the ISAS.

3. The method of claim 2, further comprising expanding a circumference of the hole through the arachnoid layer.

4. The method of claim 1, wherein penetrating the floor of the third ventricle with the distal end portion of the tool comprises making a hole through an arachnoid layer separating the third ventricle from the ISAS.

* * * * *